US010117906B2

(12) United States Patent
Dana et al.

(10) Patent No.: US 10,117,906 B2
(45) **Date of Patent: *Nov. 6, 2018**

(54) METHODS FOR REDUCING CORNEAL NERVES DAMAGE, CORNEAL LYMPHANGIOGENESIS OR IMMUNITY TO CORNEAL ANTIGENS IN DRY-EYE ASSOCIATED OCULAR SURFACE DISEASES BY IL-1RA

(75) Inventors: Reza Dana, Newton, MA (US); Mohammad Dastjerdi, Prairie Village, KS (US); Sunil Chauhan, Somerville, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 1084 days.

This patent is subject to a terminal disclaimer.

(21) Appl. No.: 12/685,510

(22) Filed: Jan. 11, 2010

(65) Prior Publication Data

US 2010/0183587 A1 Jul. 22, 2010

Related U.S. Application Data

(60) Provisional application No. 61/143,561, filed on Jan. 9, 2009.

(51) Int. Cl.

| | |
|---|---|
| ***A61K 38/00*** | (2006.01) |
| ***A61K 49/00*** | (2006.01) |
| ***A61B 5/00*** | (2006.01) |
| ***A61K 38/19*** | (2006.01) |
| ***A61K 38/20*** | (2006.01) |
| ***A61K 38/17*** | (2006.01) |
| ***A61K 9/00*** | (2006.01) |
| ***C12N 15/113*** | (2010.01) |

(52) U.S. Cl.

CPC ........ *A61K 38/1709* (2013.01); *A61K 9/0048* (2013.01); *A61K 38/1793* (2013.01); *A61K 38/2006* (2013.01); *C12N 15/1136* (2013.01); *C12N 2310/14* (2013.01)

(58) Field of Classification Search

CPC ................ A61K 2300/00; A61K 38/13; A61K 38/1709; A61K 9/0048; A61K 45/06; A61K 9/0051; A61K 38/2006; A61K 38/1793; A61K 38/20; C07K 14/705; C07K 14/545; C07K 2317/76; C07K 16/245; C07K 14/525; C07K 14/54; C12N 15/1136; C12N 15/1138; A61L 2300/252; A61L 2300/41

See application file for complete search history.

(56) References Cited

U.S. PATENT DOCUMENTS

| | | | |
|---|---|---|---|
| 6,090,775 A | 7/2000 | Rothwell et al. | |
| 6,337,072 B1 | 1/2002 | Ford et al. | |
| 6,623,736 B2 | 9/2003 | Tobinick | |
| 6,927,044 B2 | 8/2005 | Stahl et al. | |
| 6,974,682 B1 | 12/2005 | Bednarik et al. | |
| 7,683,165 B2 | 3/2010 | McSwiggen et al. | |
| 7,923,549 B2 | 4/2011 | McSwiggen et al. | |
| 9,011,861 B2 * | 4/2015 | Dana | C07K 16/22 424/130.1 |
| 2001/0041792 A1 | 11/2001 | Donde et al. | |
| 2001/0042304 A1 | 11/2001 | Sato | |
| 2003/0026806 A1 | 2/2003 | Witte et al. | |
| 2003/0083301 A1 | 5/2003 | Perez-Polo et al. | |
| 2003/0104041 A1 | 6/2003 | Hsu et al. | |
| 2004/0022718 A1 | 2/2004 | Stupp et al. | |
| 2004/0208874 A1 * | 10/2004 | Khare | 424/145.1 |
| 2005/0143333 A1 | 6/2005 | Richards et al. | |
| 2005/0171337 A1 | 8/2005 | Bednarik et al. | |
| 2006/0094663 A1 | 5/2006 | Chemtob et al. | |
| 2006/0110429 A1 * | 5/2006 | Reiff et al. | 424/427 |
| 2006/0275801 A1 | 12/2006 | Henkin | |
| 2008/0026485 A1 * | 1/2008 | Hueber et al. | 436/507 |
| 2008/0199460 A1 * | 8/2008 | Cua et al. | 424/133.1 |
| 2008/0242634 A1 | 10/2008 | Perez-Polo | |
| 2009/0012123 A1 | 1/2009 | Seike et al. | |
| 2009/0136445 A1 | 5/2009 | Wong et al. | |
| 2009/0136453 A1 | 5/2009 | Watkins | |
| 2009/0143324 A1 | 6/2009 | McSwiggen et al. | |
| 2009/0214619 A1 * | 8/2009 | Reiff et al. | 424/427 |
| 2009/0234005 A1 | 9/2009 | Ishida et al. | |
| 2010/0028328 A1 * | 2/2010 | Reiff et al. | 424/130.1 |
| 2010/0047204 A1 | 2/2010 | Yoo et al. | |
| 2010/0184824 A1 | 7/2010 | McSwiggen et al. | |
| 2010/0203103 A1 * | 8/2010 | Dana et al. | 424/429 |
| 2011/0104236 A1 * | 5/2011 | Dana et al. | 424/429 |
| 2012/0014970 A1 * | 1/2012 | Dana et al. | 424/158.1 |

(Continued)

FOREIGN PATENT DOCUMENTS

| | | |
|---|---|---|
| CA | 2398900 A1 | 8/2001 |
| JP | 2006200504 A | 8/2006 |

(Continued)

OTHER PUBLICATIONS

Watari et al. Biochem. Biophys. Res. Commun. 2008; 377: 826-831.*

(Continued)

*Primary Examiner* — Chang-Yu Wang

(74) *Attorney, Agent, or Firm* — Mintz, Levin, Cohn, Ferris, Glovsky and Popeo, P.C.; Ingrid A. Beattie

(57) ABSTRACT

The invention provides methods and compositions for minimizing, preventing, or treating damage to corneal nerves by administering to a subject with such damage or at risk of exposure to such damage a composition which blocks an activity of an IL-1 cytokine and/or an IL-17 cytokine.

15 Claims, 13 Drawing Sheets

Specification includes a Sequence Listing.

(56) References Cited

U.S. PATENT DOCUMENTS

| | | | | |
|---|---|---|---|---|
| 2013/0045927 A1* | 2/2013 | Dana | C07K 16/22 514/20.8 |
| 2015/0246966 A1* | 9/2015 | Dana | C07K 16/22 424/85.2 |

FOREIGN PATENT DOCUMENTS

| | | | |
|---|---|---|---|
| JP | 2007526292 | A | 9/2007 |
| JP | 2008534680 | A | 8/2008 |
| WO | WO-9822130 | A1 | 5/1998 |
| WO | WO-0156606 | A1 | 8/2001 |
| WO | WO-03022213 | A2 | 3/2003 |
| WO | WO-2007027761 | A2 | 3/2007 |
| WO | WO-2007120828 | A1 | 10/2007 |
| WO | WO-07145618 | A1 | 12/2007 |
| WO | WO-2008118930 | A1 | 10/2008 |
| WO | WO-2009025763 | A2 | 2/2009 |
| WO | WO-2009089036 | A2 | 7/2009 |

OTHER PUBLICATIONS

Barrett et al., "Combined antibiotic and IL-1 receptor antagonist treatment decreases stromal inflammation after *P. aeruginosa* induced keratitis", *IOVS*, 42(4):S252, 1361-B674 (Abstract Only), Mar. 15, 2001.

Biswas et al., "Counteracting corneal immunoinflammatory lesion with interleukin-1 receptor antagonist protein", *J. Leukocyte Biol.*, 76:868-875 (2004).

Jie et al., "Interleukin-1 receptor antagonist eye drops promoting high-risk corneal allografts survival in rats", *Ch. Med. J.*, 117(5):711-716 (2004).

Abe et al., "Proinflammatory Cytokines Stimulate the Expression of Nerve Growth Factor by Human Intervertebral Disc Cells", *Spine*, 32(6):635-642 (2007).

Akuzawa et al., "Interleukin-1 receptor antagonist attenuates the severity of spinal cord ischemic injury in rabbits", *J. Vasular Surg.*, 48(3): 694-700 (2008).

Antin et al., "Recombinant Human Interleukin-1 Receptor Antagonist in the Treatment of Steroid-Resistant Graft-Versus-Host Disease", *Blood*, 84(4):1342-1348 (1994).

Arend, W. P., "Interleukin-1 Receptor Antagonist", *Adv. Immunol.*, 54:167-227(1993).

Battat et al., "Effects of Laser In Situ Keratomileusis on Tear Production, Clearance, and the Ocular Surface", *Opthalmol.*, 108:1230-1235 (2001).

Benoist et al., "In vivo sequence requirements of the SV40 early promoter region", *Nature*, 290:304-310 (1981).

Bresnihan et al., "Interleukin-1 Receptor Antagonist", *Rheum Dis Clin North Am.*, 24(3): 615-628 (1998).

Brinster et al., "Regulation of metallothionein-thymidine kinase fusion plasmids injected into mouse eggs", *Nature*, 296:39-42 (1988).

Caron et al., "Chondroprotective Effect of Intraarticular Injections of Interleukin-1 Receptor Antagonist in Experimental Osteoarthritis", *Arthritis Rheum.*, 39(9):1535-1544 (1996).

Cavanagh et al., "The molecular basis or neurotrophic keratitis", *Acta Opthamol.*, 67(Suppl. 192):115-134 (1989).

Dartt D. A., "Dysfuntional Neural Regulation of Lacrimal Gland Secretion and its Role in the Pathogenesis of Dry Eye Syndromes", *Ocul Surf.*, 2(2):76-91 (2004).

Dayer et al., "Anti-interleukin-1 therapy in rheumatic diseases", *Curr. Opin. Rheumatol.*, 13:170-176 (2001).

DeKosky et al., "Interleukin-1 Receptor Antagonist Suppresses Neurotrophin Response in Injured Rat Brain", *Ann. Neurol.* 39:123-127 (1996).

Dinarello, C..A., "Biologic Basis for Interleukin-1 in Disease", *Blood*, 87(6):2095-2147 (1996).

Edwards, C. K., "Combination Cytokine Therapy in Rheumatoid Arthritis: The Next Generation", *J. Clin. Rheumatol.*, 7(3):S17-S24 (2001).

Fisher et al., "Recombinant Human Interleukin 1 Receptor Antagonist in the Treatment of Patients with Sepsis Syndrome", *JAMA*, 271(23)1836-1843 (1994).

Foulks et al., "Meibomian Gland Dysfunction: A Clinical Scheme for Description, Diagnosis, Classification, and Grading", *Occul Surf.*, 1(3):107-126 (2003).

Freund et al., "Upregulation of nerve growth factor expression by human airway smooth muscle cells in inflammatory conditions", *Eur. Respir. J.*, 20:458-463 (2002).

Gabay et al., "Mouse IL-1 receptor antagonist isoforms: complementary DNA cloning and protein expression of intracellular isoform and tissue distribution of secreted and intracellular IL-1 receptor antagonist in vivo", *J. Immunol.*, 159 (12): 5905-5913 (1997).

GenBank Accession No. AF057168, dated Apr. 14, 1998.

GenBank Accession No. AF305200, dated Jan. 9, 2001.

GenBank Accession No. BTD00060, dated Jun. 13, 2005.

GenBank Accession No. M55646, dated Jan. 6, 1995.

GenBank Accession No. NM_000575, dated Apr. 12, 2009.

GenBank Accession No. NM_000576, dated Jan. 3, 2010.

GenBank Accession No. NM_000577, dated Apr. 19, 2009.

GenBank Accession No. NM_000877, dated Apr. 12, 2009.

GenBank Accession No. NM_001025242, dated Apr. 5, 2010.

GenBank Accession No. NM_001025243, dated Apr. 5, 2010.

GenBank Accession No. NM_001080973; replaced by NM_017563, dated Mar. 5, 2010.

GenBank Accession No. NM_001569, dated Apr. 5, 2010.

GenBank Accession No. NM_002182, dated Mar. 5, 2010.

GenBank Accession No. NM_002190, dated Feb. 21, 2010.

GenBank Accession No. NM_004633, dated Mar. 16, 2010.

GenBank Accession No. NM_013278, dated Mar. 12, 2010.

GenBank Accession No. NM_014339, dated Mar. 16, 2010.

GenBank Accession No. NM_014443, dated Dec. 6, 2009.

GenBank Accession No. NM_017563, dated Mar. 5, 2010.

GenBank Accession No. NM_018725, dated Mar. 16, 2010.

GenBank Accession No. NM_032732, dated Mar. 16, 2010.

GenBank Accession No. NM_052872, dated Mar. 16, 2010.

GenBank Accession No. NM_134470, dated Mar. 5, 2010.

GenBank Accession No. NM_138284, dated Jan. 31, 2010.

GenBank Accession No. NM_153460, dated Mar. 16, 2010.

GenBank Accession No. NM_153461, dated Mar. 16, 2010.

GenBank Accession No. NM_153480, dated Mar. 5, 2010.

GenBank Accession No. NM_153481, dated Mar. 4, 2010.

GenBank Accession No. NM_153483, dated Mar. 5, 2010.

GenBank Accession No. NM_173343, dated Mar. 16, 2010.

GenBank Accession No. NM_173841, dated Apr. 19, 2009.

GenBank Accession No. NM_173842, dated Apr. 19, 2009.

GenBank Accession No. NM_173843, dated Apr. 12, 2009.

Guenard et al., "Peripheral Nerve Regeneration Is Impeded by Interleukin-1 Receptor Antagonist Released From a Polymeric Guidance Channel", *J. Neurosci. Res.*, 29:396-400 (1991).

Hynninen et al., "Interleukin 1 Receptor Antagonist and E-Selectin Concentrations: A Comparison in Patients With Severe Acute Pancreatitis and Severe Sepsis", *J. Crit. Care*, 14(2):63-68 (1999).

Jiang, et al., "A Multicenter, Double-Blind, Dose-Ranging, Randomized, Placebo-Controlled Study of Recombinant Human Interleukin-1 Receptor Antagonist in Patients With Rheumatoid Arthritis", *Arthritis Rheum.*, 43(5):1001-1009 (2000).

Keane-Myers et al., "Prevention of Allergic Eye Disease by Treatment with IL-1 Receptor Antagonist", *Invest Opthalmol Vis. Sci.*, 40(12):3041-3046 (1999).

Larsen et al., "Interleukin-1-Receptor Antagonist in Type 2 Diabetes Mellitus", *N. Engl. J. Med.*, 356:1517-1526 (2007).

McDevitt et al., "Interleukin-1 Genetic Association With Periodontitis in Clinical Practice", *J. Periodontol.*, 71(2):156-163 (2000).

Müller et al., "Corneal nerves: structure, contents and function", *Exp. Eye Res.*, 76:521-542 (2003).

Müller et al., "Ultrastructural Organization of Human Corneal Nerves", *Invest. Opthalmol Vis Sci.*, 37(4):476-488 (1996).

(56) References Cited

OTHER PUBLICATIONS

O'Neill et al., "Signal transduction pathways activated by the IL-1 receptor family: ancient signaling machinery in mammals, insects, and plants", *J. Leukocyte Biol.* 63:650-657 (1998).
Okusawa et al., "Interleukin 1 Induces a Shock-like State in Rabbits", *J. Clin. Invest.*, 81:1162-1172 (1988).
Patel et al., "Interleukin-1 in the Brain. Mechanisms of Action in Acute Neurodegeneration", *Ann. N.Y. Acad. Sci.*, 992:39-47 (2003).
Reiff et al., "The Use of Anakinra in Juvenile Arthritis", *Curr. Rheumatol. Rep.*, 7:434-440 (2005).
Rozsa et al., "Density and Organization of Free Nerve Endings in the Corneal Epithelium of the Rabbit", *Pain*, 14:105-120 (1982).
Ryoke et al., "A Conditioning Lesion Promotes in Vivo Nerve Regeneration in the Contralateral Sciatic Nerve of Rats", *Biochem. Biophys. Res. Comm.*, 267(3):715-718 (2000).
Temporin et al., "Interleukin-1 beta promotes sensory nerve regeneration after sciatic nerve injury", *Neurosci Lett.*, 440(2):130-133 (2008).
Teoh et al., "Tailoring biological treatment:anakinra treatment of posterior uveitis associated with the CINCA syndrome", *Br. J Opthalmol.*, 91:263-264(2007).
Wagner et al., "Nucleotide sequence of the thymidine kinase gene of herpes simplex virus type 1", *Proc. Natl. Acad. Sci. U;S.A.*, 78(3):1441-1445 (1981).
Xu et al., "Decrease in Corneal Sensitivity and Change in Tear Function in Dry Eye", *Cornea.* 15(3):235-239 (1996).
Yamada et al., "Interleukin-1 Receptor Antagonist Therapy and Induction of Anterior Chamber-Associated Immune Deviation-Type Tolerance after Corneal Transplantation", *Invest. Opthalmol. Vis Sci.*, 41:4203-4208 (2000).
Yamada et al., "Local suppression of IL-1 by receptor antagonist in the rat model of corneal alkali injury", *Exp Eye Res.*, 76:161-167 (2003).
Yamamoto et al., "Identification of a Functional Promoter in the Long Terminal Repeat of Rous Sarcoma Virus", *Cell*, 22 787-797 (1980).
Yamasaki et al., "Interleukin-1 as a Pathogenetic Mediator of Ischemic Brain Damage in Rats", *Stroke*, 26:676-681 (1995).
Corneal Transplant Surgery—A Guide for Patients from University of Michigan Kellogg Eye Center, retrieved from the website, www.kellogg.umich.edu/patientcare/downloads/Understand-Corneal-Transplant-Surgery.pdf on Feb. 23, 2014.
Loddick et al., Endogenous interleukin-1 receptor antagonist is neuroprotective. Biochem Biophys Res Commun. May 8, 1997;234(1):211-5.
Maertzdorf et al., IL-17 expression in human herpetic stromal keratitis: modulatory effects on chemokine production by corneal fibroblasts. J Immunol. Nov. 15, 2002;169(10):5897-903.
Uveitis facts and symptoms, retrieved from the NEI website, www.nei.nih.gov/health/uveitis/uveitis.asg#top on Feb. 23, 2014.

* cited by examiner

FIGURE 2
Before Treatment
After Treatment

SEQUENCE LISTING

```
<160> NUMBER OF SEQ ID NOS: 45

<210> SEQ ID NO 1
<211> LENGTH: 2943
<212> TYPE: DNA
<213> ORGANISM: Homo sapiens

<400> SEQUENCE: 1

accaggcaac accattgaag gctcatatgt aaaaatccat gccttccttt ctcccaatct     60

ccattcccaa acttagccac tggcttctgg ctgaggcctt acgcatacct cccggggctt    120

gcacacacct tcttctacag aagacacacc ttgggcatat cctacagaag accaggcttc    180

tctctggtcc ttggtagagg gctactttac tgtaacaggg ccagggtgga gagttctctc    240

ctgaagctcc atcccctcta taggaaatgt gttgacaata ttcagaagag taagaggatc    300

aagacttctt tgtgctcaaa taccactgtt ctcttctcta ccctgcccta accaggagct    360

tgtcacccca aactctgagg tgatttatgc cttaatcaag caaacttccc tcttcagaaa    420

agatggctca ttttccctca aaagttgcca ggagctgcca agtattctgc caattcaccc    480

tggagcacaa tcaacaaatt cagccagaac acaactacag ctactattag aactattatt    540

attaataaat tcctctccaa atctagcccc ttgacttcgg atttcacgat ttctcccttc    600

ctcctagaaa cttgataagt ttcccgcgct tccctttttc taagactaca tgtttgtcat    660

cttataaagc aaaggggtga ataaatgaac caaatcaata acttctggaa tatctgcaaa    720

caacaataat atcagctatg ccatctttca ctattttagc cagtatcgag ttgaatgaac    780

atagaaaaat acaaaactga attcttccct gtaaattccc cgttttgacg acgcacttgt    840

agccacgtag ccacgcctac ttaagacaat tacaaaaggc gaagaagact gactcaggct    900

taagctgcca gccagagagg gagtcatttc attggcgttt gagtcagcaa agaagtcaag    960

atggccaaag ttccagacat gtttgaagac ctgaagaact gttacagtga aaatgaagaa   1020

gacagttcct ccattgatca tctgtctctg aatcagaaat ccttctatca tgtaagctat   1080

ggcccactcc atgaaggctg catggatcaa tctgtgtctc tgagtatctc tgaaacctct   1140
```

```
aaaacatcca agcttacctt caaggagagc atggtggtag tagcaaccaa cgggaaggtt   1200

ctgaagaaga gacggttgag tttaagccaa tccatcactg atgatgacct ggaggccatc   1260

gccaatgact cagaggaaga aatcatcaag cctaggtcag caccttttag cttcctgagc   1320

aatgtgaaat acaactttat gaggatcatc aaatacgaat tcatcctgaa tgacgccctc   1380

aatcaaagta taattcgagc caatgatcag tacctcacgg ctgctgcatt acataatctg   1440

gatgaagcag tgaaatttga catgggtgct tataagtcat caaaggatga tgctaaaatt   1500

accgtgattc taagaatctc aaaaactcaa ttgtatgtga ctgcccaaga tgaagaccaa   1560

ccagtgctgc tgaaggagat gcctgagata cccaaaacca tcacaggtag tgagaccaac   1620

ctcctcttct tctgggaaac tcacggcact aagaactatt tcacatcagt tgcccatcca   1680

aacttgttta ttgccacaaa gcaagactac tgggtgtgct tggcaggggg gccaccctct   1740

atcactgact ttcagatact ggaaaaccag gcgtaggtct ggagtctcac ttgtctcact   1800

tgtgcagtgt tgacagttca tatgtaccat gtacatgaag aagctaaatc ctttactgtt   1860

agtcatttgc tgagcatgta ctgagccttg taattctaaa tgaatgttta cactctttgt   1920

aagagtggaa ccaacactaa catataatgt tgttatttaa agaacaccct atattttgca   1980

tagtaccaat cattttaatt attattcttc ataacaattt taggaggacc agagctactg   2040

actatggcta ccaaaaagac tctacccata ttacagatgg gcaaattaag gcataagaaa   2100

actaagaaat atgcacaata gcagttgaaa caagaagcca cagacctagg atttcatgat   2160

ttcatttcaa ctgtttgcct tctactttta agttgctgat gaactcttaa tcaaatagca   2220

taagtttctg ggacctcagt tttatcattt tcaaaatgga gggaataata cctaagcctt   2280

cctgccgcaa cagtttttta tgctaatcag ggaggtcatt ttggtaaaat acttcttgaa   2340

gccgagcctc aagatgaagg caaagcacga aatgttattt tttaattatt atttatatat   2400

gtatttataa atatatttaa gataattata atatactata tttatgggaa ccccttcatc   2460

ctctgagtgt gaccaggcat cctccacaat agcagacagt gttttctggg ataagtaagt   2520

ttgatttcat taatacaggg cattttggtc caagttgtgc ttatcccata gccaggaaac   2580

tctgcattct agtacttggg agacctgtaa tcatataata aatgtacatt aattaccttg   2640

agccagtaat tggtccgatc tttgactctt ttgccattaa acttacctgg gcattcttgt   2700

ttcaattcca cctgcaatca agtcctacaa gctaaaatta gatgaactca actttgacaa   2760

ccatgagacc actgttatca aaactttctt ttctggaatg taatcaatgt ttcttctagg   2820

ttctaaaaat tgtgatcaga ccataatgtt acattattat caacaatagt gattgataga   2880

gtgttatcag tcataactaa ataaagcttg caacaaaatt ctctgacaaa aaaaaaaaaa   2940

aaa                                                                 2943
```

<210> SEQ ID NO 2
<211> LENGTH: 213
<212> TYPE: PRT
<213> ORGANISM: Homo sapiens

<400> SEQUENCE: 2

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Asp Ser Glu Glu
        35                  40                  45
```

-continued

Glu Ile Ile Lys Pro Arg Ser Ala Pro Phe Ser Phe Leu Ser Asn Val
50 55 60

Lys Tyr Asn Phe Met Arg Ile Ile Lys Tyr Glu Phe Ile Leu Asn Asp
65 70 75 80

Ala Leu Asn Gln Ser Ile Ile Arg Ala Asn Asp Gln Tyr Leu Thr Ala
85 90 95

Ala Ala Leu His Asn Leu Asp Glu Ala Val Lys Phe Asp Met Gly Ala
100 105 110

Tyr Lys Ser Ser Lys Asp Asp Ala Lys Ile Thr Val Ile Leu Arg Ile
115 120 125

Ser Lys Thr Gln Leu Tyr Val Thr Ala Gln Asp Glu Asp Gln Pro Val
130 135 140

Leu Leu Lys Glu Met Pro Glu Ile Pro Lys Thr Ile Thr Gly Ser Glu
145 150 155 160

Thr Asn Leu Leu Phe Phe Trp Glu Thr His Gly Thr Lys Asn Tyr Phe
165 170 175

Thr Ser Val Ala His Pro Asn Leu Phe Ile Ala Thr Lys Gln Asp Tyr
180 185 190

Trp Val Cys Leu Ala Gly Gly Pro Pro Ser Ile Thr Asp Phe Gln Ile
195 200 205

Leu Glu Asn Gln Ala
210

<210> SEQ ID NO 3
<211> LENGTH: 1498
<212> TYPE: DNA
<213> ORGANISM: Homo sapiens

<400> SEQUENCE: 3
accaaacctc ttcgaggcac aaggcacaac aggctgctct gggattctct tcagccaatc 60
ttcattgctc aagtgtctga agcagccatg gcagaagtac ctgagctcgc cagtgaaatg 120
atggcttatt acagtggcaa tgaggatgac ttgttctttg aagctgatgg ccctaaacag 180
atgaagtgct ccttccagga cctggacctc tgccctctgg atggcggcat ccagctacga 240
atctccgacc accactacag caagggcttc aggcaggccg cgtcagttgt tgtggccatg 300
gacaagctga ggaagatgct ggttccctgc ccacagacct tccaggagaa tgacctgagc 360
accttctttc ccttcatctt tgaagaagaa cctatcttct tcgacacatg ggataacgag 420
gcttatgtgc acgatgcacc tgtacgatca ctgaactgca cgctccggga ctcacagcaa 480
aaaagcttgg tgatgtctgg tccatatgaa ctgaaagctc tccacctcca gggacaggat 540
atggagcaac aagtggtgtt ctccatgtcc tttgtacaag gagaagaaag taatgacaaa 600
atacctgtgg ccttgggcct caaggaaaag aatctgtacc tgtcctgcgt gttgaaagat 660
gataagccca ctctacagct ggagagtgta gatcccaaaa attacccaaa gaagaagatg 720
gaaaagcgat ttgtcttcaa caagatagaa atcaataaca agctggaatt tgagtctgcc 780
cagttcccca actggtacat cagcacctct caagcagaaa acatgcccgt cttcctggga 840
gggaccaaag gcggccagga tataactgac ttcaccatgc aatttgtgtc ttcctaaaga 900
gagctgtacc cagagagtcc tgtgctgaat gtggactcaa tccctagggc tggcagaaag 960
ggaacagaaa ggtttttgag tacggctata gcctggactt tcctgttgtc tacaccaatg 1020
cccaactgcc tgccttaggg tagtgctaag aggatctcct gtccatcagc caggacagtc 1080
agctctctcc tttcagggcc aatccccagc ccttttgttg agccaggcct ctctcacctc 1140
tcctactcac ttaaagcccg cctgacagaa accacggcca catttggttc taagaaaccc 1200
tctgtcattc gctcccacat tctgatgagc aaccgcttcc ctatttattt atttatttgt 1260
ttgtttgttt tattcattgg tctaatttat tcaaaggggg caagaagtag cagtgtctgt 1320
aaaagagcct agtttttaat agctatggaa tcaattcaat ttggactggt gtgctctctt 1380
taaatcaagt cctttaatta agactgaaaa tatataagct cagattattt aaatgggaat 1440
atttataaat gagcaaatat catactgttc aatggttctg aaataaactt cactgaag 1498

<210> SEQ ID NO 4
<211> LENGTH: 269
<212> TYPE: PRT
<213> ORGANISM: Homo sapiens

<400> SEQUENCE: 4

Met Ala Glu Val Pro Glu Leu Ala Ser Glu Met Met Ala Tyr Tyr Ser
1 5 10 15

Gly Asn Glu Asp Asp Leu Phe Phe Glu Ala Asp Gly Pro Lys Gln Met
20 25 30

Lys Cys Ser Phe Gln Asp Leu Asp Leu Cys Pro Leu Asp Gly Gly Ile
35 40 45

Gln Leu Arg Ile Ser Asp His His Tyr Ser Lys Gly Phe Arg Gln Ala
50 55 60

Ala Ser Val Val Val Ala Met Asp Lys Leu Arg Lys Met Leu Val Pro
65 70 75 80

Cys Pro Gln Thr Phe Gln Glu Asn Asp Leu Ser Thr Phe Phe Pro Phe
85 90 95

Ile Phe Glu Glu Glu Pro Ile Phe Phe Asp Thr Trp Asp Asn Glu Ala
100 105 110

Tyr Val His Asp Ala Pro Val Arg Ser Leu Asn Cys Thr Leu Arg Asp
115 120 125

Ser Gln Gln Lys Ser Leu Val Met Ser Gly Pro Tyr Glu Leu Lys Ala
130 135 140

Leu His Leu Gln Gly Gln Asp Met Glu Gln Gln Val Val Phe Ser Met
145 150 155 160

Ser Phe Val Gln Gly Glu Glu Ser Asn Asp Lys Ile Pro Val Ala Leu
165 170 175

Gly Leu Lys Glu Lys Asn Leu Tyr Leu Ser Cys Val Leu Lys Asp Asp
180 185 190

Lys Pro Thr Leu Gln Leu Glu Ser Val Asp Pro Lys Asn Tyr Pro Lys
195 200 205

Lys Lys Met Glu Lys Arg Phe Val Phe Asn Lys Ile Glu Ile Asn Asn
210 215 220

Lys Leu Glu Phe Glu Ser Ala Gln Phe Pro Asn Trp Tyr Ile Ser Thr
225 230 235 240

Ser Gln Ala Glu Asn Met Pro Val Phe Leu Gly Gly Thr Lys Gly Gly
245 250 255

Gln Asp Ile Thr Asp Phe Thr Met Gln Phe Val Ser Ser
260 265

<210> SEQ ID NO 5
<211> LENGTH: 1760
<212> TYPE: DNA
<213> ORGANISM: Homo sapiens

<400> SEQUENCE: 5

-continued

```
atttctttat aaaccacaac tctgggcccg caatggcagt ccactgcctt gctgcagtca      60
cagaatggaa atctgcagag gcctccgcag tcacctaatc actctcctcc tcttcctgtt     120
ccattcagag acgatctgcc gaccctctgg gagaaaatcc agcaagatgc aagccttcag     180
aatctgggat gttaaccaga agaccttcta tctgaggaac aaccaactag ttgctggata     240
cttgcaagga ccaaatgtca atttagaaga aaagatagat gtggtaccca ttgagcctca     300
tgctctgttc ttgggaatcc atggagggaa gatgtgcctg tcctgtgtca agtctggtga     360
tgagaccaga ctccagctgg aggcagttaa catcactgac ctgagcgaga acagaaagca     420
ggacaagcgc ttcgccttca tccgctcaga cagcggcccc accaccagtt ttgagtctgc     480
cgcctgcccc ggttggttcc tctgcacagc gatggaagct gaccagcccg tcagcctcac     540
caatatgcct gacgaaggcg tcatggtcac caaattctac ttccaggagg acgagtagta     600
ctgcccaggc ctgcctgttc ccattcttgc atggcaagga ctgcagggac tgccagtccc     660
cctgccccag ggctcccggc tatgggggca ctgaggacca gccattgagg ggtggaccct     720
cagaaggcgt cacaagaacc tggtcacagg actctgcctc ctcttcaact gaccagcctc     780
catgctgcct ccagaatggt ctttctaatg tgtgaatcag agcacagcag cccctgcaca     840
aagcccttcc atgtcgcctc tgcattcagg atcaaacccc gaccacctgc ccaacctgct     900
ctcctcttgc cactgcctct tcctccctca ttccaccttc ccatgccctg gatccatcag     960
gccacttgat gacccccaac caagtggctc ccacaccctg ttttacaaaa aagaaaagac    1020
cagtccatga gggaggtttt taagggtttg tggaaaatga aaattaggat ttcatgattt    1080
tttttttca gtccccgtga aggagagccc ttcatttgga gattatgttc tttcggggag    1140
aggctgagga cttaaaatat tcctgcattt gtgaaatgat ggtgaaagta agtggtagct    1200
tttcccttct ttttcttctt tttttgtgat gtcccaactt gtaaaaatta aaagttatgg    1260
tactatgtta gccccataat tttttttttc cttttaaaac acttccataa tctggactcc    1320
tctgtccagg cactgctgcc cagcctccaa gctccatctc cactccagat tttttacagc    1380
tgcctgcagt actttacctc ctatcagaag tttctcagct cccaaggctc tgagcaaatg    1440
tggctcctgg gggttctttc ttcctctgct gaaggaataa attgctcctt gacattgtag    1500
agcttctggc acttggagac ttgtatgaaa gatggctgtg cctctgcctg tctcccccac    1560
cgggctggga gctctgcaga gcaggaaaca tgactcgtat atgtctcagg tccctgcagg    1620
gccaagcacc tagcctcgct cttggcaggt actcagcgaa tgaatgctgt atatgttggg    1680
tgcaaagttc cctacttcct gtgacttcag ctctgtttta caataaaatc ttgaaaatgc    1740
ctaaaaaaaa aaaaaaaaaa                                                1760
```

<210> SEQ ID NO 6
<211> LENGTH: 177
<212> TYPE: PRT
<213> ORGANISM: Homo sapiens

<400> SEQUENCE: 6

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
```

-continued

```
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu


<210> SEQ ID NO 7
<211> LENGTH: 1865
<212> TYPE: DNA
<213> ORGANISM: Homo sapiens

<400> SEQUENCE: 7

gggcagctcc accctgggag ggactgtggc ccaggtactg cccgggtgct actttatggg      60

cagcagctca gttgagttag agtctggaag acctcagaag acctcctgtc ctatgaggcc     120

ctccccatgg ctttagctga cttgtatgaa gaaggaggtg gaggaggagg agaaggtgaa     180

gacaatgctg actcaaagga gacgatctgc cgaccctctg ggagaaaatc cagcaagatg     240

caagccttca gaatctggga tgttaaccag aagaccttct atctgaggaa caaccaacta     300

gttgctggat acttgcaagg accaaatgtc aatttagaag aaaagataga tgtggtaccc     360

attgagcctc atgctctgtt cttgggaatc catggaggga agatgtgcct gtcctgtgtc     420

aagtctggtg atgagaccag actccagctg gaggcagtta acatcactga cctgagcgag     480

aacagaaagc aggacaagcg cttcgccttc atccgctcag acagcggccc caccaccagt     540

tttgagtctg ccgcctgccc cggttggttc ctctgcacag cgatggaagc tgaccagccc     600

gtcagcctca ccaatatgcc tgacgaaggc gtcatggtca ccaaattcta cttccaggag     660

gacgagtagt actgcccagg cctgcctgtt cccattcttg catggcaagg actgcaggga     720

ctgccagtcc ccctgcccca gggctcccgg ctatgggggc actgaggacc agccattgag     780

gggtggaccc tcagaaggcg tcacaagaac ctggtcacag gactctgcct cctcttcaac     840

tgaccagcct ccatgctgcc tccagaatgg tctttctaat gtgtgaatca gagcacagca     900

gcccctgcac aaagcccttc catgtcgcct ctgcattcag gatcaaaccc cgaccacctg     960

cccaacctgc tctcctcttg ccactgcctc ttcctccctc attccacctt cccatgccct    1020

ggatccatca ggccacttga tgacccccaa ccaagtggct cccacaccct gttttacaaa    1080

aaagaaaaga ccagtccatg agggaggttt ttaagggttt gtggaaaatg aaaattagga    1140

tttcatgatt tttttttttc agtccccgtg aaggagagcc cttcatttgg agattatgtt    1200

ctttcgggga gaggctgagg acttaaaata ttcctgcatt tgtgaaatga tggtgaaagt    1260

aagtggtagc ttttcccttc tttttcttct ttttttgtga tgtcccaact tgtaaaaatt    1320

aaaagttatg gtactatgtt agccccataa tttttttttt ccttttaaaa cacttccata    1380
```

atctggactc ctctgtccag gcactgctgc ccagcctcca agctccatct ccactccaga 1440 tttttacag ctgcctgcag tactttacct cctatcagaa gtttctcagc tcccaaggct 1500
ctgagcaaat gtggctcctg gggttcttt cttcctctgc tgaaggaata aattgctcct 1560
tgacattgta gagcttctgg cacttggaga cttgtatgaa agatggctgt gcctctgcct 1620
gtctccccca ccgggctggg agctctgcag agcaggaaac atgactcgta tatgtctcag 1680
gtccctgcag ggccaagcac ctagcctcgc tcttggcagg tactcagcga atgaatgctg 1740
tatatgttgg gtgcaaagtt ccctacttcc tgtgacttca gctctgtttt acaataaaat 1800
cttgaaaatg cctaaaaaaa aaaaaaaaaa aaaaaaaaaa aaaaaaaaaa aaaaaaaaaa 1860
aaaaa 1865

<210> SEQ ID NO 8
<211> LENGTH: 180
<212> TYPE: PRT
<213> ORGANISM: Homo sapiens

<400> SEQUENCE: 8

Met Ala Leu Ala Asp Leu Tyr Glu Glu Gly Gly Gly Gly Gly Gly Glu
1 5 10 15

Gly Glu Asp Asn Ala Asp Ser Lys Glu Thr Ile Cys Arg Pro Ser Gly
20 25 30

Arg Lys Ser Ser Lys Met Gln Ala Phe Arg Ile Trp Asp Val Asn Gln
35 40 45

Lys Thr Phe Tyr Leu Arg Asn Asn Gln Leu Val Ala Gly Tyr Leu Gln
50 55 60

Gly Pro Asn Val Asn Leu Glu Glu Lys Ile Asp Val Val Pro Ile Glu
65 70 75 80

Pro His Ala Leu Phe Leu Gly Ile His Gly Gly Lys Met Cys Leu Ser
85 90 95

Cys Val Lys Ser Gly Asp Glu Thr Arg Leu Gln Leu Glu Ala Val Asn
100 105 110

Ile Thr Asp Leu Ser Glu Asn Arg Lys Gln Asp Lys Arg Phe Ala Phe
115 120 125

Ile Arg Ser Asp Ser Gly Pro Thr Thr Ser Phe Glu Ser Ala Ala Cys
130 135 140

Pro Gly Trp Phe Leu Cys Thr Ala Met Glu Ala Asp Gln Pro Val Ser
145 150 155 160

Leu Thr Asn Met Pro Asp Glu Gly Val Met Val Thr Lys Phe Tyr Phe
165 170 175

Gln Glu Asp Glu
180

<210> SEQ ID NO 9
<211> LENGTH: 1802
<212> TYPE: DNA
<213> ORGANISM: Homo sapiens

<400> SEQUENCE: 9
gggcagctcc accctgggag ggactgtggc ccaggtactg cccgggtgct actttatggg 60
cagcagctca gttgagttag agtctggaag acctcagaag acctcctgtc ctatgaggcc 120
ctccccatgg ctttagagac gatctgccga ccctctggga gaaaatccag caagatgcaa 180
gccttcagaa tctgggatgt taaccagaag accttctatc tgaggaacaa ccaactagtt 240
gctggatact tgcaaggacc aaatgtcaat ttagaagaaa agatagatgt ggtacccatt 300

```
gagcctcatg ctctgttctt gggaatccat ggagggaaga tgtgcctgtc ctgtgtcaag    360

tctggtgatg agaccagact ccagctggag gcagttaaca tcactgacct gagcgagaac    420

agaaagcagg acaagcgctt cgccttcatc cgctcagaca gcggccccac caccagtttt    480

gagtctgccg cctgccccgg ttggttcctc tgcacagcga tggaagctga ccagcccgtc    540

agcctcacca atatgcctga cgaaggcgtc atggtcacca aattctactt ccaggaggac    600

gagtagtact gcccaggcct gcctgttccc attcttgcat ggcaaggact gcagggactg    660

ccagtccccc tgccccaggg ctcccggcta tgggggcact gaggaccagc cattgagggg    720

tggaccctca gaaggcgtca caagaacctg gtcacaggac tctgcctcct cttcaactga    780

ccagcctcca tgctgcctcc agaatggtct ttctaatgtg tgaatcagag cacagcagcc    840

cctgcacaaa gcccttccat gtcgcctctg cattcaggat caaaccccga ccacctgccc    900

aacctgctct cctcttgcca ctgcctcttc ctccctcatt ccaccttccc atgccctgga    960

tccatcaggc cacttgatga cccccaacca agtggctccc acaccctgtt ttacaaaaaa   1020

gaaaagacca gtccatgagg gaggttttta agggtttgtg gaaaatgaaa attaggattt   1080

catgattttt tttttcagt ccccgtgaag gagagccctt catttggaga ttatgttctt   1140

tcggggagag gctgaggact taaaatattc ctgcatttgt gaaatgatgg tgaaagtaag   1200

tggtagcttt tcccttcttt ttcttctttt tttgtgatgt cccaacttgt aaaaattaaa   1260

agttatggta ctatgttagc cccataattt tttttttcct tttaaaacac ttccataatc   1320

tggactcctc tgtccaggca ctgctgccca gcctccaagc tccatctcca ctccagattt   1380

tttacagctg cctgcagtac tttacctcct atcagaagtt tctcagctcc caaggctctg   1440

agcaaatgtg gctcctgggg gttctttctt cctctgctga aggaataaat tgctccttga   1500

cattgtagag cttctggcac ttggagactt gtatgaaaga tggctgtgcc tctgcctgtc   1560

tcccccaccg ggctgggagc tctgcagagc aggaaacatg actcgtatat gtctcaggtc   1620

cctgcagggc caagcaccta gcctcgctct tggcaggtac tcagcgaatg aatgctgtat   1680

atgttgggtg caaagttccc tacttcctgt gacttcagct ctgttttaca ataaaatctt   1740

gaaaatgcct aaaaaaaaaa aaaaaaaaaa aaaaaaaaaa aaaaaaaaaa aaaaaaaaaa   1800

aa                                                                  1802
```

<210> SEQ ID NO 10
<211> LENGTH: 159
<212> TYPE: PRT
<213> ORGANISM: Homo sapiens

<400> SEQUENCE: 10

```
Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95
```

```
Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155


<210> SEQ ID NO 11
<211> LENGTH: 1973
<212> TYPE: DNA
<213> ORGANISM: Homo sapiens

<400> SEQUENCE: 11

gggcagctcc accctgggag ggactgtggc ccaggtactg cccgggtgct actttatggg     60

cagcagctca gttgagttag agtctggaag acctcagaag acctcctgtc ctatgaggcc    120

ctccccatgg ctttaggggg attataaaac taatcatcaa agccaagaag gcaagagcaa    180

gcatgtaccg ctgaaaacac aagataactg cataagtaat gactttcagt gcagattcat    240

agctaaccca taaactgctg gggcaaaaat catcttggaa ggctctgaac ctcagaaagg    300

attcacaaga cgatctgccg accctctggg agaaaatcca gcaagatgca agccttcaga    360

atctgggatg ttaaccagaa gaccttctat ctgaggaaca accaactagt tgctggatac    420

ttgcaaggac caaatgtcaa tttagaagaa aagatagatg tggtacccat tgagcctcat    480

gctctgttct tgggaatcca tggagggaag atgtgcctgt cctgtgtcaa gtctggtgat    540

gagaccagac tccagctgga ggcagttaac atcactgacc tgagcgagaa cagaaagcag    600

gacaagcgct tcgccttcat ccgctcagac agcggcccca ccaccagttt tgagtctgcc    660

gcctgccccg gttggttcct ctgcacagcg atggaagctg accagcccgt cagcctcacc    720

aatatgcctg acgaaggcgt catggtcacc aaattctact tccaggagga cgagtagtac    780

tgcccaggcc tgcctgttcc cattcttgca tggcaaggac tgcagggact gccagtcccc    840

ctgccccagg gctcccggct atgggggcac tgaggaccag ccattgaggg gtggaccctc    900

agaaggcgtc acaagaacct ggtcacagga ctctgcctcc tcttcaactg accagcctcc    960

atgctgcctc cagaatggtc tttctaatgt gtgaatcaga gcacagcagc ccctgcacaa   1020

agcccttcca tgtcgcctct gcattcagga tcaaaccccg accacctgcc caacctgctc   1080

tcctcttgcc actgcctctt cctccctcat tccaccttcc catgccctgg atccatcagg   1140

ccacttgatg acccccaacc aagtggctcc cacaccctgt tttacaaaaa agaaaagacc   1200

agtccatgag ggaggttttt aagggtttgt ggaaaatgaa aattaggatt tcatgatttt   1260

tttttttcag tccccgtgaa ggagagccct tcatttggag attatgttct ttcggggaga   1320

ggctgaggac ttaaaatatt cctgcatttg tgaaatgatg gtgaaagtaa gtggtagctt   1380

ttcccttctt tttcttcttt ttttgtgatg tcccaacttg taaaaattaa aagttatggt   1440

actatgttag ccccataatt tttttttcc ttttaaaaca cttccataat ctggactcct   1500

ctgtccaggc actgctgccc agcctccaag ctccatctcc actccagatt ttttacagct   1560

gcctgcagta ctttacctcc tatcagaagt ttctcagctc ccaaggctct gagcaaatgt   1620

ggctcctggg ggttctttct tcctctgctg aaggaataaa ttgctccttg acattgtaga   1680

gcttctggca cttggagact tgtatgaaag atggctgtgc ctctgcctgt ctccccccacc   1740

gggctgggag ctctgcagag caggaaacat gactcgtata tgtctcaggt ccctgcaggg   1800
```

ccaagcacct agcctcgctc ttggcaggta ctcagcgaat gaatgctgta tatgttgggt 1860
gcaaagttcc ctacttcctg tgacttcagc tctgttttac aataaaatct tgaaaatgcc 1920
taaaaaaaaa aaaaaaaaaa aaaaaaaaaa aaaaaaaaaa aaaaaaaaaa aaa 1973

<210> SEQ ID NO 12
<211> LENGTH: 143
<212> TYPE: PRT
<213> ORGANISM: Homo sapiens

<400> SEQUENCE: 12

Met Gln Ala Phe Arg Ile Trp Asp Val Asn Gln Lys Thr Phe Tyr Leu
1 5 10 15

Arg Asn Asn Gln Leu Val Ala Gly Tyr Leu Gln Gly Pro Asn Val Asn
20 25 30

Leu Glu Glu Lys Ile Asp Val Val Pro Ile Glu Pro His Ala Leu Phe
35 40 45

Leu Gly Ile His Gly Gly Lys Met Cys Leu Ser Cys Val Lys Ser Gly
50 55 60

Asp Glu Thr Arg Leu Gln Leu Glu Ala Val Asn Ile Thr Asp Leu Ser
65 70 75 80

Glu Asn Arg Lys Gln Asp Lys Arg Phe Ala Phe Ile Arg Ser Asp Ser
85 90 95

Gly Pro Thr Thr Ser Phe Glu Ser Ala Ala Cys Pro Gly Trp Phe Leu
100 105 110

Cys Thr Ala Met Glu Ala Asp Gln Pro Val Ser Leu Thr Asn Met Pro
115 120 125

Asp Glu Gly Val Met Val Thr Lys Phe Tyr Phe Gln Glu Asp Glu
130 135 140

<210> SEQ ID NO 13
<211> LENGTH: 602
<212> TYPE: DNA
<213> ORGANISM: Homo sapiens

<400> SEQUENCE: 13
agctccaccc tgggagggac tgtggcccag gtactgcccg ggtgctactt tatgggcagc 60
agctcagttg agttagagtc tggaagacct cagaagacct cctgtcctat gaggccctcc 120
ccatggcttt agagacgatc tgccgaccct ctgggagaaa atccagcaag atgcaagcct 180
tcagaatctg ggatgttaac cagaagacct tctatctgag gaacaaccaa ctagttgctg 240
gatacttgca aggaccaaat gtcaatttag aagaaaagat agatgtggta cccattgagc 300
ctcatgctct gttcttggga atccatggag ggaagatgtg cctgtcctgt gtcaagtctg 360
gtgatgagac cagactccag ctggaggcag ttaacatcac tgacctgagc gagaacagaa 420
agcaggacaa gcgcttcgcc ttcatccgct cagacagtgg ccccaccacc agttttgagt 480
ctgccgcctg ccccggttgg ttcctctgca cagcgatgga agctgaccag cccgtcagcc 540
tcaccaatat gcctgacgaa ggcgtcatgg tcaccaaatt ctacttccag gaggacgagt 600
ag 602

<210> SEQ ID NO 14
<211> LENGTH: 159
<212> TYPE: PRT
<213> ORGANISM: Homo sapiens

<400> SEQUENCE: 14

```
Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155


<210> SEQ ID NO 15
<211> LENGTH: 602
<212> TYPE: DNA
<213> ORGANISM: Homo sapiens

<400> SEQUENCE: 15

agctccaccc tgggagggac tgtggcccag gtactgcccg ggtgctactt tatgggcagc      60

agctcagttg agttagagtc tggaagacct cagaagacct cctgtcctat gaggccctcc     120

ccatggcttt agagacgatc tgccgaccct ctgggagaaa atccagcaag atgcaagcct     180

tcagaatctg ggatgttaac cagaagacct tctatctgag gaacaaccaa ctagttgctg     240

gatacttgca aggaccaaat gtcaatttag aagaaaagat agatgtggta cccattgagc     300

ctcatgctct gttcttggga atccatggag ggaagatgtg cctgtcctgt gtcaagtctg     360

gtgatgagac cagactccag ctggaggcag ttaacatcac tgacctgagc gagaacagaa     420

agcaggacaa gcgcttcgcc ttcatccgct cagacagtgg ccccaccacc agttttgagt     480

ctgccgcctg ccccggttgg ttcctctgca cagcgatgga agctgaccag cccgtcagcc     540

tcaccaatat gcctgacgaa ggcgtcatgg tcaccaaatt ctacttccag gaggacgagt     600

ag                                                                    602


<210> SEQ ID NO 16
<211> LENGTH: 153
<212> TYPE: PRT
<213> ORGANISM: Homo sapiens

<400> SEQUENCE: 16

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
```

-continued

```
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```

<210> SEQ ID NO 17
<211> LENGTH: 4909
<212> TYPE: DNA
<213> ORGANISM: Homo sapiens

<400> SEQUENCE: 17

```
tagacgcacc ctctgaagat ggtgactccc tcctgagaag ctggacccct tggtaaaaga     60
caaggccttc tccaagaaga atatgaaagt gttactcaga cttatttgtt tcatagctct    120
actgatttct tctctggagg ctgataaatg caaggaacgt gaagaaaaaa taattttagt    180
gtcatctgca aatgaaattg atgttcgtcc ctgtcctctt aacccaaatg aacacaaagg    240
cactataact tggtataaag atgacagcaa gacacctgta tctacagaac aagcctccag    300
gattcatcaa cacaaagaga aactttggtt tgttcctgct aaggtggagg attcaggaca    360
ttactattgc gtggtaagaa attcatctta ctgcctcaga attaaaataa gtgcaaaatt    420
tgtggagaat gagcctaact tatgttataa tgcacaagcc atatttaagc agaaactacc    480
cgttgcagga gacggaggac ttgtgtgccc ttatatggag ttttttaaaa atgaaaataa    540
tgagttacct aaattacagt ggtataagga ttgcaaacct ctacttcttg acaatataca    600
ctttagtgga gtcaaagata ggctcatcgt gatgaatgtg gctgaaaagc atagagggaa    660
ctatacttgt catgcatcct acacatactt gggcaagcaa tatcctatta cccgggtaat    720
agaatttatt actctagagg aaaacaaacc cacaaggcct gtgattgtga gcccagctaa    780
tgagacaatg gaagtagact tgggatccca gatacaattg atctgtaatg tcaccggcca    840
gttgagtgac attgcttact ggaagtggaa tgggtcagta attgatgaag atgacccagt    900
gctaggggaa gactattaca gtgtggaaaa tcctgcaaac aaaagaagga gtaccctcat    960
cacagtgctt aatatatcgg aaattgaaag tagattttat aaacatccat ttacctgttt   1020
tgccaagaat acacatggta tagatgcagc atatatccag ttaatatatc cagtcactaa   1080
tttccagaag cacatgattg gtatatgtgt cacgttgaca gtcataattg tgtgttctgt   1140
tttcatctat aaaatcttca agattgacat tgtgctttgg tacagggatt cctgctatga   1200
ttttctccca ataaaagctt cagatggaaa gacctatgac gcatatatac tgtatccaaa   1260
gactgttggg gaagggtcta cctctgactg tgatattttt gtgtttaaag tcttgcctga   1320
ggtcttggaa aaacagtgtg gatataagct gttcatttat ggaagggatg actacgttgg   1380
ggaagacatt gttgaggtca ttaatgaaaa cgtaaagaaa agcagaagac tgattatcat   1440
tttagtcaga gaaacatcag gcttcagctg gctgggtggt tcatctgaag agcaaatagc   1500
catgtataat gctcttgttc aggatggaat taaagttgtc ctgcttgagc tggagaaaat   1560
```

-continued

```
ccaagactat gagaaaatgc cagaatcgat taaattcatt aagcagaaac atggggctat   1620
ccgctggtca ggggacttta cacagggacc acagtctgca aagacaaggt tctggaagaa   1680
tgtcaggtac cacatgccag tccagcgacg gtcaccttca tctaaacacc agttactgtc   1740
accagccact aaggagaaac tgcaaagaga ggctcacgtg cctctcgggt agcatggaga   1800
agttgccaag agttctttag gtgcctcctg tcttatggcg ttgcaggcca ggttatgcct   1860
catgctgact tgcagagttc atggaatgta actatatcat cctttatccc tgaggtcacc   1920
tggaatcaga ttattaaggg aataagccat gacgtcaata gcagcccagg gcacttcaga   1980
gtagagggct tgggaagatc ttttaaaaag gcagtaggcc cggtgtggtg gctcacgcct   2040
ataatcccag cactttggga ggctgaagtg ggtggatcac cagaggtcag gagttcgaga   2100
ccagcccagc caacatggca aaaccccatc tctactaaaa atacaaaaat gagctaggca   2160
tggtggcaca cgcctgtaat cccagctaca cctgaggctg aggcaggaga attgcttgaa   2220
ccggggagac ggaggttgca gtgagccgag tttgggccac tgcactctag cctggcaaca   2280
gagcaagact ccgtctcaaa aaaagggcaa taaatgccct ctctgaatgt ttgaactgcc   2340
aagaaaaggc atggagacag cgaactagaa gaaagggcaa gaaggaaata gccaccgtct   2400
acagatggct tagttaagtc atccacagcc caagggcggg gctatgcctt gtctggggac   2460
cctgtagagt cactgaccct ggagcggctc tcctgagagg tgctgcaggc aaagtgagac   2520
tgacacctca ctgaggaagg gagacatatt cttggagaac tttccatctg cttgtatttt   2580
ccatacacat ccccagccag aagttagtgt ccgaagaccg aattttattt tacagagctt   2640
gaaaactcac ttcaatgaac aaagggattc tccaggattc caaagttttg aagtcatctt   2700
agctttccac aggagggaga gaacttaaaa aagcaacagt agcagggaat tgatccactt   2760
cttaatgctt tcctccctgg catgaccatc ctgtcctttg ttattatcct gcattttacg   2820
tctttggagg aacagctccc tagtggcttc ctccgtctgc aatgtccctt gcacagccca   2880
cacatgaacc atccttccca tgatgccgct cttctgtcat cccgctcctg ctgaaacacc   2940
tcccaggggc tccacctgtt caggagctga agcccatgct ttcccaccag catgtcactc   3000
ccagaccacc tccctgccct gtcctccagc ttcccctcgc tgtcctgctg tgtgaattcc   3060
caggttggcc tggtggccat gtcgcctgcc cccagcactc ctctgtctct gctcttgcct   3120
cgacccttcc tcctcctttg cctaggaggc cttctcgcat tttctctagc tgatcagaat   3180
tttaccaaaa ttcagaacat cctccaattc cacagtctct gggagacttt ccctaagagg   3240
cgacttcctc tccagccttc tctctctggt caggcccact gcagagatgg tggtgagcac   3300
atctgggagg ctggtctccc tccagctgga attgctgctc tctgagggag aggctgtggt   3360
ggctgtctct gtccctcact gccttccagg agcaatttgc acatgtaaca tagatttatg   3420
taatgcttta tgtttaaaaa cattccccaa ttatcttatt taatttttgc aattattcta   3480
attttatata tagagaaagt gacctatttt ttaaaaaaat cacactctaa gttctattga   3540
acctaggact tgagcctcca tttctggctt ctagtctggt gttctgagta cttgatttca   3600
ggtcaataac ggtcccccct cactccacac tggcacgttt gtgagaagaa atgacatttt   3660
gctaggaagt gaccgagtct aggaatgctt ttattcaaga caccaaattc caaacttcta   3720
aatgttggaa ttttcaaaaa ttgtgtttag attttatgaa aaactcttct actttcatct   3780
attctttccc tagaggcaaa catttcttaa aatgtttcat tttcattaaa aatgaaagcc   3840
aaatttatat gccaccgatt gcaggacaca agcacagttt taagagttgt atgaacatgg   3900
```

```
agaggacttt tggtttttat atttctcgta tttaatatgg gtgaacacca acttttattt   3960

ggaataataa ttttcctcct aaacaaaaac acattgagtt taagtctctg actcttgcct   4020

ttccacctgc tttctcctgg gcccgctttg cctgcttgaa ggaacagtgc tgttctggag   4080

ctgctgttcc aacagacagg gcctagcttt catttgacac acagactaca gccagaagcc   4140

catggagcag ggatgtcacg tcttgaaaag cctattagat gttttacaaa tttaattttg   4200

cagattattt tagtctgtca tccagaaaat gtgtcagcat gcatagtgct aagaaagcaa   4260

gccaatttgg aaacttaggt tagtgacaaa attggccaga gagtgggggt gatgatgacc   4320

aagaattaca agtagaatgg cagctggaat ttaaggaggg acaagaatca atggataagc   4380

gtgggtggag gaagatccaa acagaaaagt gcaaagttat tccccatctt ccaagggttg   4440

aattctggag gaagaagaca cattcctagt tccccgtgaa cttcctttga cttattgtcc   4500

ccactaaaac aaaacaaaaa acttttaatg ccttccacat taattagatt ttcttgcagt   4560

tttttatgg catttttttta aagatgccct aagtgttgaa gaagagtttg caaatgcaac   4620

aaaatattta attaccggtt gttaaaactg gtttagcaca atttatattt tccctctctt   4680

gcctttctta tttgcaataa aaggtattga gccatttttt aaatgacatt tttgataaat   4740

tatgtttgta ctagttgatg aaggagtttt ttttaacctg tttatataat tttgcagcag   4800

aagccaaatt ttttgtatat taaagcacca aattcatgta cagcatgcat cacggatcaa   4860

tagactgtac ttattttcca ataaaatttt caaactttgt actgttaaa               4909
```

<210> SEQ ID NO 18
<211> LENGTH: 569
<212> TYPE: PRT
<213> ORGANISM: Homo sapiens

<400> SEQUENCE: 18

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
```

-continued

```
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565
```

<210> SEQ ID NO 19
<211> LENGTH: 1484
<212> TYPE: DNA
<213> ORGANISM: Homo sapiens

<400> SEQUENCE: 19

```
cccgtgagga ggaaaaggtg tgtccgctgc cacccagtgt gagcgggtga caccacccgg      60

ttaggaaatc ccagctccca agagggtata aatccctgct ttactgctga gctcctgctg     120

gaggtgaaag tctggcctgg cagccttccc caggtgagca gcaacaaggc cacgtgctgc     180

tgggtctcag tcctccactt cccgtgtcct ctggaagttg tcaggagcaa tgttgcgctt     240

gtacgtgttg gtaatgggag tttctgcctt cacccttcag cctgcggcac acacaggggc     300

tgccagaagc tgccggtttc gtgggaggca ttacaagcgg gagttcaggc tggaagggga     360

gcctgtagcc ctgaggtgcc cccaggtgcc ctactggttg tgggcctctg tcagcccccg     420

catcaacctg acatggcata aaaatgactc tgctaggacg gtcccaggag aagaagagac     480

acggatgtgg gcccaggacg gtgctctgtg gcttctgcca gccttgcagg aggactctgg     540

cacctacgtc tgcactacta gaaatgcttc ttactgtgac aaaatgtcca ttgagctcag     600

agtttttgag aatacagatg ctttcctgcc gttcatctca tacccgcaaa ttttaacctt     660

gtcaacctct ggggtattag tatgccctga cctgagtgaa ttcacccgtg acaaaactga     720

cgtgaagatt caatggtaca aggattctct tcttttggat aaagacaatg agaaatttct     780

aagtgtgagg gggaccactc acttactcgt acacgatgtg gccctggaag atgctggcta     840

ttaccgctgt gtcctgacat ttgcccatga aggccagcaa tacaacatca ctaggagtat     900

tgagctacgc atcaagaaaa aaaaagaaga gaccattcct gtgatcattt cccccctcaa     960

gaccatatca gcttctctgg ggtcaagact gacaatcccg tgtaaggtgt ttctgggaac    1020

cggcacaccc ttaaccacca tgctgtggtg gacggccaat gacacccaca tagagagcgc    1080

ctacccggga ggccgcgtga ccgaggggcc acgccaggaa tattcagaaa ataatgagaa    1140

ctacattgaa gtgccattga tttttgatcc tgtcacaaga gaggatttgc acatggattt    1200

taaatgtgtt gtccataata ccctgagttt tcagacacta cgcaccacag tcaaggaagc    1260

ctcctccacg ttctcctggg gcattgtgct ggccccactt tcactggcct tcttggtttt    1320

ggggggaata tggatgcaca gacggtgcaa acacagaact ggaaaagcag atggtctgac    1380

tgtgctatgg cctcatcatc aagactttca atcctatccc aagtgaaata aatggaatga    1440

aataattcaa acacaaaaaa aaaaaaaaaa aaaaaaaaaa aaaa                     1484
```

<210> SEQ ID NO 20
<211> LENGTH: 1436
<212> TYPE: DNA
<213> ORGANISM: Homo sapiens

<400> SEQUENCE: 20

```
gggatgggag atactgttgt ggtcacctct ggaaaataca ttctgctact cttaaaaact      60

agtgacgctc atacaaatca acagaaagag cttctgaagg aagactttaa agctgcttct     120

gccacgtgct gctgggtctc agtcctccac ttcccgtgtc ctctggaagt tgtcaggagc     180

aatgttgcgc ttgtacgtgt tggtaatggg agtttctgcc ttcacccttc agcctgcggc     240

acacacaggg gctgccagaa gctgccggtt tcgtgggagg cattacaagc gggagttcag     300

gctggaaggg gagcctgtag ccctgaggtg cccccaggtg ccctactggt tgtgggcctc     360

tgtcagcccc cgcatcaacc tgacatggca taaaaatgac tctgctagga cggtcccagg     420

agaagaagag acacggatgt gggcccagga cggtgctctg tggcttctgc cagccttgca     480

ggaggactct ggcacctacg tctgcactac tagaaatgct tcttactgtg acaaaatgtc     540

cattgagctc agagtttttg agaatacaga tgctttcctg ccgttcatct catacccgca     600

aattttaacc ttgtcaacct ctggggtatt agtatgccct gacctgagtg aattcacccg     660
```

-continued

```
tgacaaaact gacgtgaaga ttcaatggta caaggattct cttcttttgg ataaagacaa    720

tgagaaattt ctaagtgtga gggggaccac tcacttactc gtacacgatg tggccctgga    780

agatgctggc tattaccgct gtgtcctgac atttgcccat gaaggccagc aatacaacat    840

cactaggagt attgagctac gcatcaagaa aaaaaaagaa gagaccattc ctgtgatcat    900

ttccccccctc aagaccatat cagcttctct ggggtcaaga ctgacaatcc cgtgtaaggt    960

gtttctggga accggcacac ccttaaccac catgctgtgg tggacggcca atgacaccca   1020

catagagagc gcctacccgg gaggccgcgt gaccgagggg ccacgccagg aatattcaga   1080

aaataatgag aactacattg aagtgccatt gatttttgat cctgtcacaa gagaggattt   1140

gcacatggat tttaaatgtg ttgtccataa taccctgagt tttcagacac tacgcaccac   1200

agtcaaggaa gcctcctcca cgttctcctg ggcattgtg ctggccccac tttcactggc   1260

cttcttggtt ttgggggaa tatggatgca cagacggtgc aaacacagaa ctggaaaagc   1320

agatggtctg actgtgctat ggcctcatca tcaagacttt caatcctatc ccaagtgaaa   1380

taaatggaat gaaataattc aaacacaaaa aaaaaaaaaa aaaaaaaaaa aaaaaa       1436
```

```
<210> SEQ ID NO 21
<211> LENGTH: 398
<212> TYPE: PRT
<213> ORGANISM: Homo sapiens

<400> SEQUENCE: 21

Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240
```

```
Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Trp Gly Ile
            340                 345                 350

Val Leu Ala Pro Leu Ser Leu Ala Phe Leu Val Leu Gly Gly Ile Trp
        355                 360                 365

Met His Arg Arg Cys Lys His Arg Thr Gly Lys Ala Asp Gly Leu Thr
    370                 375                 380

Val Leu Trp Pro His His Gln Asp Phe Gln Ser Tyr Pro Lys
385                 390                 395


<210> SEQ ID NO 22
<211> LENGTH: 3177
<212> TYPE: DNA
<213> ORGANISM: Homo sapiens

<400> SEQUENCE: 22

cagaagacct cctgtcctat gaggccctcc ccatggcttt aggtaagctc cttccactct     60

catttttca cctgagaaat gagagaggaa aatgtctaca attggtgttt atcaaatgct    120

ttcaggctct ggtgagcaag cgtccaggaa aatgtcaagc gcatggagct ccaggcctgt    180

ctgggggatc tgggcacggg gaggcatcca tgggagacca tgcaggcact ctgaggcagg    240

ggctgcaagc tagtgcctgc tggggcagca ggtgaacaga gaggtgtaac tgctgtgaca    300

gaagtcatgg agtccttgga gtgtgagggt cattttccac tgttgataga atagggaaat    360

tggtgaaata gccctgttaa atgagagaaa gaacagtgtg agctcaatga gaaatactaa    420

tagaatgtgg cactgagcca caaggtctga gggttgattg ataaggaagg gtggggactg    480

tggagaatta agggcttggc acaggtcagt tccaccagtt gtcacaagag aatgcaggct    540

caggtggcca gaacttctcg cttttccaga agagtccgat attctgattt cattatatat    600

agtattctga ttaaaccaga caataaagca agcagataaa atatttaaag tataagctgc    660

cagtttgcaa cctccggtta ggatttgtgt ggggcaaaga aaaaaactct caggatcatt    720

ggtatgtaga ctctaatttt aagtttctaa tttaaaattg gcccctgagg ctgggcgtgg    780

tggctcacac ctgtaatccc agcattttgg gaggccaagg tgggtggatc tcttgaggtc    840

aagagttcaa ggcctgcctg gccaacatgg tgaaaccctg tctctattaa aaatacaaaa    900

attagctggg catggtggtg catgtctgca atcttagcta cttgggtagc taaggcagga    960

gaattgctgg aacccgggag gtagaggttg cagtgaatgg agatcacacc actgcactcc   1020

agtctgggca atagagagag acgctctctc taaaaaaaaa tatgtaaaga taaataaaat   1080

gaaataaaat aggcctctaa tgagcaggcc attctccttt ctgggtctta ctttccttgc   1140

actcctttct gggtgttaag aggaggtcta gaggaagctg gacaactctt agcttgtagt   1200
```

```
aagcacagtg gaagtatcag ctcttaatgg gtcatggaca cgttacgaag ctaggcgccg   1260

tgctgagcac tttacatggt ttatcccact gaaccctctc aataacccta tgaggaaggg   1320

ctattattgc tcacattttc agaagaggaa atggatatag agagattaga taatttgccc   1380

atggccagac agctagtata agaggaggag gtggattgac tgcagacatt ctgtcttcaa   1440

accactacac tatgctatgg aggcacagag acttaatgaa atcatggaga ggggaattgc   1500

tttgtcaacc acaagcagtt attccggggg cagcagatcc tcccctgtcc cccagtggta   1560

caatggtccc tggtgggttg tgctacaatg ttagcccatg gtcttatgtg tttttcaaat   1620

gtgtaaagta ggatgctgga accactctta gaaccagata ccaatacatt gtgaagaaat   1680

aaatctctgt gcttaaaact ggttcatccc aaaatatttt gaactgacac acaataggtg   1740

ctaaataaat gtgtgttaac ttgaattgga ttgaattcgg gaaaaaagtg caataagctt   1800

agtgaagaca ccatgttccc tgggtagagg aaccacattc tccatctaag gccaggagta   1860

tgggaggtat caatgtttgc ccagcacaga acagggtgcc aagaagagaa aagttgacgg   1920

ggtgcatact ctgactggaa actggaaggg tgagaacaga gggtaaagga tagagatgga   1980

accatgtgca tacactttgt gttaccttgg acaagtcatt catttctctg gacctctgct   2040

ttctctctac acaatggggt cccaccactt cccttacagc tgacttgtat gaagaaggag   2100

gtggaggagg aggagaaggt gaagacaatg ctgactcaaa gggtaaatta tttttaggat   2160

ccaagtttga aaacaatttt aggctactag atatgaacaa catcttgatt atgtagttga   2220

aggaaattaa agatgaatgg tttaattaaa aattaatcag aatgaaaacg attgattact   2280

aatatatctg caatggttta ttttcctgag tggcagactc actaaggttt ttgaatactc   2340

ctgtgtgatt gctctatgta tgtatgtatg tatgtatgta tgcatgtatc tatctatctg   2400

ttgtctaata gaatggatca catctctgct aataaaaaca ctacactggc agggtacaat   2460

tataatcatt aactgtgcct ggaatttgca gcagcagcca ccagaggtac cagtgccctt   2520

taagggttca taatttagaa taatccaatt atctgagttt ttcagggact gaggggtttg   2580

gcaaggtgta gaactttcag taataaagtc aagaaagtcc tggacaaacc aaggtagttg   2640

gtcactctag tccataacca ggtaaagagc tttccctgta acctgtgtaa ggttttagaa   2700

tcatttcttt ccttattacc aaaaatcctc cccaaatttt caagaaatta tgaactaaat   2760

agttactcta tgagatagga gttcagccca aaagaaacac cataagaaca aatataattc   2820

ttgcttatgt taaccatgca atgaagcaga gagaaaaagt cagtggcctc tttaggagga   2880

ctgtagtgtg ggaagaaata actaaactgg gtttcaatcc tggcctggcc aggatctgga   2940

gcaagtgagt taatctttct aagccttgag tagtttataa aagaatggcc actccataga   3000

cagagtagcc tgaaccttga gttcttctat aaagtcacta tgaatttata ctcattttga   3060

aagtgggtgt caatatgtct gtccactttg cacagctgtt atgtggacaa aaggagatct   3120

gtgtgaaagt gtaacacaga gcctaaacta taacaggtaa gcaacacagt tgtccct      3177
```

```
<210> SEQ ID NO 23
<211> LENGTH: 20
<212> TYPE: PRT
<213> ORGANISM: Homo sapiens

<400> SEQUENCE: 23

Asp Leu Tyr Glu Glu Gly Gly Gly Gly Gly Gly Glu Gly Glu Asp Asn
1               5                   10                  15

Ala Asp Ser Lys
            20
```

<210> SEQ ID NO 24
<211> LENGTH: 4725
<212> TYPE: DNA
<213> ORGANISM: Homo sapiens

<400> SEQUENCE: 24

```
tgccgggatc caggtctccg gggtccgctt tggccagagg cgcggaagga agcagtgccc     60

ggcgacactg cacccatccc ggctgctttt gctgcgccct ctcagcttcc caagaaaggc    120

atcgtcatgt gatcatcacc taagaactag aacatcagca ggccctagaa gcctcactct    180

tgcccctccc tttaatatct caaaggatga cacttctgtg gtgtgtagtg agtctctact    240

tttatggaat cctgcaaagt gatgcctcag aacgctgcga tgactgggga ctagacacca    300

tgaggcaaat ccaagtgttt gaagatgagc cagctcgcat caagtgccca ctctttgaac    360

acttcttgaa attcaactac agcacagccc attcagctgg ccttactctg atctggtatt    420

ggactaggca ggaccgggac cttgaggagc caattaactt ccgcctcccc gagaaccgca    480

ttagtaagga gaaagatgtg ctgtggttcc ggcccactct cctcaatgac actggcaact    540

atacctgcat gttaaggaac actacatatt gcagcaaagt tgcatttccc ttggaagttg    600

ttcaaaaaga cagctgtttc aattccccca tgaaactccc agtgcataaa ctgtatatag    660

aatatggcat tcagaggatc acttgtccaa atgtagatgg atattttcct tccagtgtca    720

aaccgactat cacttggtat atgggctgtt ataaaataca gaattttaat aatgtaatac    780

ccgaaggtat gaacttgagt ttcctcattg ccttaatttc aaataatgga aattacacat    840

gtgttgttac atatccagaa aatggacgta cgtttcatct caccaggact ctgactgtaa    900

aggtagtagg ctctccaaaa aatgcagtgc cccctgtgat ccattcacct aatgatcatg    960

tggtctatga gaaagaacca ggagaggagc tactcattcc ctgtacggtc tattttagtt   1020

ttctgatgga ttctcgcaat gaggtttggt ggaccattga tggaaaaaaa cctgatgaca   1080

tcactattga tgtcaccatt aacgaaagta taagtcatag tagaacagaa gatgaaacaa   1140

gaactcagat tttgagcatc aagaaagtta cctctgagga tctcaagcgc agctatgtct   1200

gtcatgctag aagtgccaaa ggcgaagttc caaagcagcc aaggtgaagc agaaagtgcc   1260

agctccaaga tacacagtgg aactggcttg tggttttgga gccacagtcc tgctagtggt   1320

gattctcatt gttgtttacc atgtttactg gctagagatg gtcctatttt accgggctca   1380

ttttggaaca gatgaaacca ttttagatgg aaaagagtat gatatttatg tatcctatgc   1440

aaggaatgcg gaagaagaag aatttgtatt actgaccctc cgtggagttt tggagaatga   1500

atttggatac aagctgtgca tctttgaccg agacagtctg cctgggggaa ttgtcacaga   1560

tgagactttg agcttcattc agaaaagcag acgcctcctg gttgttctaa gccccaacta   1620

cgtgctccag ggaacccaag ccctcctgga gctcaaggct ggcctagaaa atatggcctc   1680

tcggggcaac atcaacgtca ttttagtaca gtacaaagct gtgaaggaaa cgaaggtgaa   1740

agagctgaag agggctaaga cggtgctcac ggtcattaaa tggaaagggg aaaaatccaa   1800

gtatccacag ggcaggttct ggaagcagct gcaggtggcc atgccagtga agaaaagtcc   1860

caggcggtct agcagtgatg agcagggcct ctcgtattca tctttgaaaa atgtatgaaa   1920

ggaataatga aaagggtaaa aagaacaagg ggtgctccag gaagaaagag tccccccagt   1980

cttcattcgc agtttatggt ttcataggca aaaataatgg tctaagcctc ccaataggga   2040

taaatttagg gtgactgtgt ggctgactat tctgcttcct caggcaacac taaagtttag   2100
```

-continued

```
aaagatatca tcaacgttct gtcaccagtc tctgatgcca ctatgttctt tgcaggcaaa   2160
gacttgttca atgcgaattt ccccttctac attgtctatc cctgttttta tatgtctcca   2220
ttctttttaa aatcttaaca tatggagcag cctttcctat gaatttaaat atgcctttaa   2280
aataagtcac tgttgacagg gtcatgagtt tccgagtata gttttctttt tatcttattt   2340
ttactcgtcc gttgaaaaga taatcaaggc ctacatttta gctgaggata atgaactttt   2400
ttcctcattc ggctgtataa tacataacca cagcaagact gacatccact taggatgata   2460
caaagcagtg taactgaaaa tgtttctttt aattgattta aaggacttgt cttctatacc   2520
acccttgtcc tcatctcagg taatttatga aatctatgta aacttgaaaa atatttctta   2580
atttttgttt ttgctccagt caattcctga ttatccacag gtcaacccac atttttttcat   2640
tccttctccc tatctgctta tatcgcattg ctcatttaga gtttgcagga ggctccatac   2700
taggttcagt ctgaaagaaa tctcctaatg gtgctataga gagggaggta acagaaagac   2760
tcttttaggg catttttctg actcatgaaa agagcacaga aaaggatgtt tggcaatttg   2820
tcttttaagt cttaaccttg ctaatgtgaa tactgggaaa gtgatttttt ctcactcgtt   2880
tttgttgctc cattgtaaag ggcggaggtc agtcttagtg gccttgagag ttgcttttgg   2940
cattaatatt ctaagagaat taactgtatt tcctgtcacc tattcactag tgcaggaaat   3000
atacttgctc caaataagtc agtatgagaa gtcactgtca atgaaagttg ttttgtttgt   3060
tttcagtaat attttgctgt ttttaagact tggaaaacta agtgcagagt ttacagagtg   3120
gtaaatatct atgttacatg tagattatac atatatatac acacgtgtat atgagatata   3180
tatcttatat ctccacaaac acaaattata tatatacata tccacacaca tacattacat   3240
atatctgtgt atataaatcc acatgcacat gaaatatata tatatatata atttgtgtgt   3300
gtgtatgtgt atgtatatga ctttaaatag ctatgggtac aatattaaaa accactggaa   3360
ctcttgtcca gtttttaaat tatgttttta ctggaatgtt tttgtgtcag tgttttctgt   3420
acatattatt tgttaattca cagctcacag agtgatagtt gtcatagttc ttgccttccc   3480
taagtttata taaataactt aagtattgct acagtttatc taggttgcag tggcatctgc   3540
tgtgcacaga gcttccatgg tcactgctaa gcagtagcca gccatcgggc attaattgat   3600
ttcctactat attcccagca gacacattta gaaactaagc tatgttaacc tcagtgctca   3660
actatttgaa ctgttgagtg ataaaggaaa caaatataac tgtaaatgaa tcttggtatc   3720
ctgtgaaaca gaataattcg taatttaaga aagcccttat cccggtaaca tgaatgttga   3780
tgaacaaatg taaaattata tcctatattt aagtacccat aataaatcat ttccctctat   3840
aagtgttatt gattatttta aattgaaaaa agtttcactt ggatgaaaaa agtagaaaag   3900
taggtcattc ttggatctac tttttttttag ccttattaat atttttccct attagaaacc   3960
acaattactc cctctattaa cccttcactt actagaccag aaaagaactt attccagata   4020
agctttgaat atcaattctt acataaactt taggcaaaca gggaatagtc tagtcaccaa   4080
aggaccattc tcttgccaat gctgcattcc ttttgcactt ttggattcca tatttatccc   4140
aaatgctgtt gggcacccct agaaatacct tgatgttttt tctatttata tgcctgcctt   4200
tggtacttaa ttttacaaat gctgtaatat aaagcatatc aagtttatgt gatacgtatc   4260
attgcaagag aatttgtttc aagatttttt tttaatgttc cagaagatgg ccaatagaga   4320
acattcaagg gaaatgggga aacataattt agagaacaag aacaaaccat gtctcaaatt   4380
tttttaaaaa aaattaatgg ttttaaatat atgctatagg gacgttccat gcccaggtta   4440
acaaagaact gtgatatata gagtgtctaa ttacaaaatc atatacgatt tatttaattc   4500
```

-continued tcttctgtat tgtaacttag atgattccca aggactctaa taaaaaatca cttcattgta 4560
tttggaaaca aaaacatcat tcattaatta cttattttct ttccataggt tttaatattt 4620
tgagagtgtc ttttttattt cattcatgaa cttttgtatt tttcattttt catttgattt 4680
gtaaatttac ttatgttaaa aataaaccat ttattttcag ctttg 4725

<210> SEQ ID NO 25
<211> LENGTH: 570
<212> TYPE: PRT
<213> ORGANISM: Homo sapiens

<400> SEQUENCE: 25

Met Thr Leu Leu Trp Cys Val Val Ser Leu Tyr Phe Tyr Gly Ile Leu
1 5 10 15

Gln Ser Asp Ala Ser Glu Arg Cys Asp Asp Trp Gly Leu Asp Thr Met
20 25 30

Arg Gln Ile Gln Val Phe Glu Asp Glu Pro Ala Arg Ile Lys Cys Pro
35 40 45

Leu Phe Glu His Phe Leu Lys Phe Asn Tyr Ser Thr Ala His Ser Ala
50 55 60

Gly Leu Thr Leu Ile Trp Tyr Trp Thr Arg Gln Asp Arg Asp Leu Glu
65 70 75 80

Glu Pro Ile Asn Phe Arg Leu Pro Glu Asn Arg Ile Ser Lys Glu Lys
85 90 95

Asp Val Leu Trp Phe Arg Pro Thr Leu Leu Asn Asp Thr Gly Asn Tyr
100 105 110

Thr Cys Met Leu Arg Asn Thr Thr Tyr Cys Ser Lys Val Ala Phe Pro
115 120 125

Leu Glu Val Val Gln Lys Asp Ser Cys Phe Asn Ser Pro Met Lys Leu
130 135 140

Pro Val His Lys Leu Tyr Ile Glu Tyr Gly Ile Gln Arg Ile Thr Cys
145 150 155 160

Pro Asn Val Asp Gly Tyr Phe Pro Ser Ser Val Lys Pro Thr Ile Thr
165 170 175

Trp Tyr Met Gly Cys Tyr Lys Ile Gln Asn Phe Asn Asn Val Ile Pro
180 185 190

Glu Gly Met Asn Leu Ser Phe Leu Ile Ala Leu Ile Ser Asn Asn Gly
195 200 205

Asn Tyr Thr Cys Val Val Thr Tyr Pro Glu Asn Gly Arg Thr Phe His
210 215 220

Leu Thr Arg Thr Leu Thr Val Lys Val Val Gly Ser Pro Lys Asn Ala
225 230 235 240

Val Pro Pro Val Ile His Ser Pro Asn Asp His Val Val Tyr Glu Lys
245 250 255

Glu Pro Gly Glu Glu Leu Leu Ile Pro Cys Thr Val Tyr Phe Ser Phe
260 265 270

Leu Met Asp Ser Arg Asn Glu Val Trp Trp Thr Ile Asp Gly Lys Lys
275 280 285

Pro Asp Asp Ile Thr Ile Asp Val Thr Ile Asn Glu Ser Ile Ser His
290 295 300

Ser Arg Thr Glu Asp Glu Thr Arg Thr Gln Ile Leu Ser Ile Lys Lys
305 310 315 320

Val Thr Ser Glu Asp Leu Lys Arg Ser Tyr Val Cys His Ala Arg Ser
325 330 335

Ala Lys Gly Glu Val Ala Lys Ala Ala Lys Val Lys Gln Lys Val Pro
340 345 350

Ala Pro Arg Tyr Thr Val Glu Leu Ala Cys Gly Phe Gly Ala Thr Val
355 360 365

Leu Leu Val Val Ile Leu Ile Val Val Tyr His Val Tyr Trp Leu Glu
370 375 380

Met Val Leu Phe Tyr Arg Ala His Phe Gly Thr Asp Glu Thr Ile Leu
385 390 395 400

Asp Gly Lys Glu Tyr Asp Ile Tyr Val Ser Tyr Ala Arg Asn Ala Glu
405 410 415

Glu Glu Glu Phe Val Leu Leu Thr Leu Arg Gly Val Leu Glu Asn Glu
420 425 430

Phe Gly Tyr Lys Leu Cys Ile Phe Asp Arg Asp Ser Leu Pro Gly Gly
435 440 445

Ile Val Thr Asp Glu Thr Leu Ser Phe Ile Gln Lys Ser Arg Arg Leu
450 455 460

Leu Val Val Leu Ser Pro Asn Tyr Val Leu Gln Gly Thr Gln Ala Leu
465 470 475 480

Leu Glu Leu Lys Ala Gly Leu Glu Asn Met Ala Ser Arg Gly Asn Ile
485 490 495

Asn Val Ile Leu Val Gln Tyr Lys Ala Val Lys Glu Thr Lys Val Lys
500 505 510

Glu Leu Lys Arg Ala Lys Thr Val Leu Thr Val Ile Lys Trp Lys Gly
515 520 525

Glu Lys Ser Lys Tyr Pro Gln Gly Arg Phe Trp Lys Gln Leu Gln Val
530 535 540

Ala Met Pro Val Lys Lys Ser Pro Arg Arg Ser Ser Ser Asp Glu Gln
545 550 555 560

Gly Leu Ser Tyr Ser Ser Leu Lys Asn Val
565 570

<210> SEQ ID NO 26
<211> LENGTH: 2063
<212> TYPE: DNA
<213> ORGANISM: Homo sapiens

<400> SEQUENCE: 26
tgccgggatc caggtctccg gggtccgctt tggccagagg cgcggaagga agcagtgccc 60
ggcgacactg cacccatccc ggctgctttt gctgcgccct ctcagcttcc caagaaaggc 120
atcgtcatgt gatcatcacc taagaactag aacatcagca ggccctagaa gcctcactct 180
tgcccctccc tttaatatct caaaggatga cacttctgtg gtgtgtagtg agtctctact 240
tttatggaat cctgcaaagt gatgcctcag aacgctgcga tgactgggga ctagacacca 300
tgaggcaaat ccaagtgttt gaagatgagc cagctcgcat caagtgccca ctctttgaac 360
acttcttgaa attcaactac agcacagccc attcagctgg ccttactctg atctggtatt 420
ggactaggca ggaccgggac cttgaggagc caattaactt ccgcctcccc gagaaccgca 480
ttagtaagga gaaagatgtg ctgtggttcc ggcccactct cctcaatgac actggcaact 540
atacctgcat gttaaggaac actacatatt gcagcaaagt tgcatttccc ttggaagttg 600
ttcaaaaaga cagctgtttc aattccccca tgaaactccc agtgcataaa ctgtatatag 660
aatatggcat tcagaggatc acttgtccaa atgtagatgg atattttcct tccagtgtca 720
aaccgactat cacttggtat atgggctgtt ataaaataca gaattttaat aatgtaatac 780

```
ccgaaggtat gaacttgagt ttcctcattg ccttaatttc aaataatgga aattacacat    840

gtgttgttac atatccagaa aatggacgta cgtttcatct caccaggact ctgactgtaa    900

aggtagtagg ctctccaaaa aatgcagtgc cccctgtgat ccattcacct aatgatcatg    960

tggtctatga gaaagaacca ggagaggagc tactcattcc ctgtacggtc tattttagtt   1020

ttctgatgga ttctcgcaat gaggtttggt ggaccattga tggaaaaaaa cctgatgaca   1080

tcactattga tgtcaccatt aacgaaagta taagtcatag tagaacagaa gatgaaacaa   1140

gaactcagat tttgagcatc aagaaagtta cctctgagga tctcaagcgc agctatgtct   1200

gtcatgctag aagtgccaaa ggcgaagttg ccaaagcagc caaggtgaag cagaaggta    1260

atagatgcgg tcagtgatga atctctcagc tccaaattaa cattgtggtg aataaggaca   1320

aaaggagaga ttgagaacaa gagagctcca gcacctagcc cgacggcatc taacccatag   1380

taatgaatca aacttaaatg aaaaatatga aagttttcat ctatgtaaga tactcaaaat   1440

attgtttctg atattgttag taccgtaatg cccaaatgta gctaaaaaaa tcgacgtgag   1500

tacagtgaga cacaattttg tgtctgtaca attatgaaaa attaaaaaca aagaaaatat   1560

tcaaagctac caaagataga aaaaactggt agagccacat attgttggtg aattattaag   1620

accctttttaa aaatcattca tggtagagtt taagagtcat aaaaaagatt gcatcatctg   1680

acctaagact ttcggaattt ttcctgaaca aataacagaa agggaattat ataccttttta   1740

atattattag aagcattatc tgtagttgta aaacattatt aatagcagcc atccaattgt   1800

atgcaactaa ttaaggtatt gaatgtttat tttccaaaaa tgcataatta taatattatt   1860

ttaaacacta tgtatcaata tttaagcagg tttataatat accagcagcc acaattgcta   1920

aaatgaaaat catttaaatt atgattttaa atggtataaa catgatttct atgttgatag   1980

tactatatta ttctacaata aatggaaatt ataaagcctt cttgtcagaa gtgctgctcc   2040

taaaaaaaaa aaaaaaaaaa aaa                                            2063
```

<210> SEQ ID NO 27
<211> LENGTH: 356
<212> TYPE: PRT
<213> ORGANISM: Homo sapiens

<400> SEQUENCE: 27

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140
```

Pro Val His Lys Leu Tyr Ile Glu Tyr Gly Ile Gln Arg Ile Thr Cys
145 150 155 160

Pro Asn Val Asp Gly Tyr Phe Pro Ser Ser Val Lys Pro Thr Ile Thr
165 170 175

Trp Tyr Met Gly Cys Tyr Lys Ile Gln Asn Phe Asn Asn Val Ile Pro
180 185 190

Glu Gly Met Asn Leu Ser Phe Leu Ile Ala Leu Ile Ser Asn Asn Gly
195 200 205

Asn Tyr Thr Cys Val Val Thr Tyr Pro Glu Asn Gly Arg Thr Phe His
210 215 220

Leu Thr Arg Thr Leu Thr Val Lys Val Val Gly Ser Pro Lys Asn Ala
225 230 235 240

Val Pro Pro Val Ile His Ser Pro Asn Asp His Val Val Tyr Glu Lys
245 250 255

Glu Pro Gly Glu Glu Leu Leu Ile Pro Cys Thr Val Tyr Phe Ser Phe
260 265 270

Leu Met Asp Ser Arg Asn Glu Val Trp Trp Thr Ile Asp Gly Lys Lys
275 280 285

Pro Asp Asp Ile Thr Ile Asp Val Thr Ile Asn Glu Ser Ile Ser His
290 295 300

Ser Arg Thr Glu Asp Glu Thr Arg Thr Gln Ile Leu Ser Ile Lys Lys
305 310 315 320

Val Thr Ser Glu Asp Leu Lys Arg Ser Tyr Val Cys His Ala Arg Ser
325 330 335

Ala Lys Gly Glu Val Ala Lys Ala Ala Lys Val Lys Gln Lys Gly Asn
340 345 350

Arg Cys Gly Gln
355

<210> SEQ ID NO 28
<211> LENGTH: 3589
<212> TYPE: DNA
<213> ORGANISM: Homo sapiens

<400> SEQUENCE: 28
cgcggacccg gccggcccag gcccgcgccc gccgcggccc tgagaggccc cggcaggtcc 60
cggcccggcg gcggcagcca tggccggggg gccgggcccg ggggagcccg cagcccccgg 120
cgcccagcac ttcttgtacg aggtgccgcc ctgggtcatg tgccgcttct acaaagtgat 180
ggacgccctg gagcccgccg actggtgcca gttcgccgcc ctgatcgtgc gcgaccagac 240
cgagctgcgg ctgtgcgagc gctccgggca gcgcacggcc agcgtcctgt ggccctggat 300
caaccgcaac gcccgtgtgg ccgacctcgt gcacatcctc acgcacctgc agctgctccg 360
tgcgcgggac atcatcacag cctggcaccc tcccgccccg cttccgtccc caggcaccac 420
tgccccgagg cccagcagca tccctgcacc cgccgaggcc gaggcctgga gcccccggaa 480
gttgccatcc tcagcctcca ccttcctctc cccagctttt ccaggctccc agacccattc 540
agggcctgag ctcggcctgg tcccaagccc tgcttccctg tggcctccac cgccatctcc 600
agccccttct tctaccaagc caggcccaga gagctcagtg tccctcctgc agggagcccg 660
cccctttccg ttttgctggc ccctctgtga gatttcccgg ggcacccaca acttctcgga 720
ggagctcaag atcggggagg gtggctttgg gtgcgtgtac cgggcggtga tgaggaacac 780
ggtgtatgct gtgaagaggc tgaaggagaa cgctgacctg gagtggactg cagtgaagca 840

-continued

```
gagcttcctg accgaggtgg agcagctgtc caggtttcgt cacccaaaca ttgtggactt    900
tgctggctac tgtgctcaga acggcttcta ctgcctggtg tacggcttcc tgcccaacgg    960
ctccctggag gaccgtctcc actgccagac ccaggcctgc ccacctctct cctggcctca   1020
gcgactggac atccttctgg gtacagcccg ggcaattcag tttctacatc aggacagccc   1080
cagcctcatc catggagaca tcaagagttc caacgtcctt ctggatgaga ggctgacacc   1140
caagctggga gactttggcc tggcccggtt cagccgcttt gccgggtcca gccccagcca   1200
gagcagcatg gtggcccgga cacagacagt gcggggcacc ctggcctacc tgcccgagga   1260
gtacatcaag acgggaaggc tggctgtgga cacggacacc ttcagctttg ggtggtagt    1320
gctagagacc ttggctggtc agagggctgt gaagacgcac ggtgccagga ccaagtatct   1380
gaaagacctg gtggaagagg aggctgagga ggctggagtg gctttgagaa gcacccagag   1440
cacactgcaa gcaggtctgg ctgcagatgc ctgggctgct cccatcgcca tgcagatcta   1500
caagaagcac ctggacccca ggcccgggcc ctgcccacct gagctgggcc tgggcctggg   1560
ccagctggcc tgctgctgcc tgcaccgccg ggccaaaagg aggcctccta tgacccaggt   1620
gtacgagagg ctagagaagc tgcaggcagt ggtggcgggg gtgcccgggc attcggaggc   1680
cgccagctgc atccccctt ccccgcagga gaactcctac gtgtccagca ctggcagagc    1740
ccacagtggg gctgctccat ggcagcccct ggcagcgcca tcaggagcca gtgcccaggc   1800
agcagagcag ctgcagagag gccccaacca gcccgtggag agtgacgaga gcctaggcgg   1860
cctctctgct gccctgcgct cctggcactt gactccaagc tgccctctgg acccagcacc   1920
cctcagggag gccggctgtc ctcaggggga cacggcagga gaatcgagct gggggagtgg   1980
cccaggatcc cggcccacag ccgtggaagg actggccctt ggcagctctg catcatcgtc   2040
gtcagagcca ccgcagatta tcatcaaccc tgcccgacag aagatggtcc agaagctggc   2100
cctgtacgag gatggggccc tggacagcct gcagctgctg tcgtccagct ccctcccagg   2160
cttgggcctg gaacaggaca ggcaggggcc cgaagaaagt gatgaatttc agagctgatg   2220
tgttcacctg ggcagatccc ccaaatccgg aagtcaaagt tctcatggtc agaagttctc   2280
atggtgcacg agtcctcagc actctgccgg cagtgggggt gggggcccat gcccgcgggg   2340
gagagaagga ggtggccctg ctgttctagg ctctgtgggc ataggcaggc agagtggaac   2400
cctgcctcca tgccagcatc tgggggcaag gaaggctggc atcatccagt gaggaggctg   2460
gcgcatgttg ggaggctgct ggctgcacag acccgtgagg ggaggagagg ggctgctgtg   2520
caggggtgtg gagtagggag ctggctcccc tgagagccat gcagggcgtc tgcagcccag   2580
gcctctggca gcagctcttt gcccatctct ttggacagtg gccaccctgc acaatggggc   2640
cgacgaggcc tagggccctc ctacctgctt acaatttgga aaagtgtggc cgggtgcggt   2700
ggctcacgcc tgtaatccca gcactttggg aggccaaggc aggaggatcg ctggagccca   2760
gtaggtcaag accagccagg gcaacatgat gagaccctgt ctctgccaaa aaatttttta   2820
aactattagc ctggcgtggt agcgcacgcc tgtggtccca gctgctgggg aggctgaagt   2880
aggaggatca tttatgcttg ggaggtcgag gctgcagtga gtcatgattg tatgactgca   2940
ctccagcctg ggtgacagag caagaccctg tttcaaaaag aaaaaccctg ggaaaagtga   3000
agtatggctg taagtctcat ggttcagtcc tagcaagaag cgagaattct gagatcctcc   3060
agaaagtcga gcagcaccca cctccaacct cgggccagtg tcttcaggct ttactgggga   3120
cctgcgagct ggcctaatgt ggtggcctgc aagccaggcc atccctgggc gccacagacg   3180
agctccgagc caggtcaggc ttcggaggcc acaagctcag cctcaggccc aggcactgat   3240
```

```
tgtggcagag gggccactac ccaaggtcta gctaggccca agacctagtt acccagacag   3300

tgagaagccc ctggaaggca gaaaagttgg gagcatggca gacagggaag ggaaacattt   3360

tcagggaaaa gacatgtatc acatgtcttc agaagcaagt caggtttcat gtaaccgagt   3420

gtcctcttgc gtgtccaaaa gtagcccagg gctgtagcac aggcttcaca gtgattttgt   3480

gttcagccgt gagtcacact acatgccccc gtgaagctgg gcattggtga cgtccaggtt   3540

gtccttgagt aataaaaacg tatgttgcaa taaaaaaaaa aaaaaaaaa              3589


<210> SEQ ID NO 29
<211> LENGTH: 712
<212> TYPE: PRT
<213> ORGANISM: Homo sapiens

<400> SEQUENCE: 29

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
```

-continued

```
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
    370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
            420                 425                 430

Tyr Leu Lys Asp Leu Val Glu Glu Glu Ala Glu Glu Ala Gly Val Ala
        435                 440                 445

Leu Arg Ser Thr Gln Ser Thr Leu Gln Ala Gly Leu Ala Ala Asp Ala
    450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                485                 490                 495

Ala Cys Cys Cys Leu His Arg Arg Ala Lys Arg Arg Pro Pro Met Thr
            500                 505                 510

Gln Val Tyr Glu Arg Leu Glu Lys Leu Gln Ala Val Val Ala Gly Val
        515                 520                 525

Pro Gly His Ser Glu Ala Ala Ser Cys Ile Pro Pro Ser Pro Gln Glu
    530                 535                 540

Asn Ser Tyr Val Ser Ser Thr Gly Arg Ala His Ser Gly Ala Ala Pro
545                 550                 555                 560

Trp Gln Pro Leu Ala Ala Pro Ser Gly Ala Ser Ala Gln Ala Ala Glu
                565                 570                 575

Gln Leu Gln Arg Gly Pro Asn Gln Pro Val Glu Ser Asp Glu Ser Leu
            580                 585                 590

Gly Gly Leu Ser Ala Ala Leu Arg Ser Trp His Leu Thr Pro Ser Cys
        595                 600                 605

Pro Leu Asp Pro Ala Pro Leu Arg Glu Ala Gly Cys Pro Gln Gly Asp
    610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
                645                 650                 655

Pro Pro Gln Ile Ile Ile Asn Pro Ala Arg Gln Lys Met Val Gln Lys
            660                 665                 670

Leu Ala Leu Tyr Glu Asp Gly Ala Leu Asp Ser Leu Gln Leu Leu Ser
        675                 680                 685

Ser Ser Ser Leu Pro Gly Leu Gly Leu Glu Gln Asp Arg Gln Gly Pro
    690                 695                 700

Glu Glu Ser Asp Glu Phe Gln Ser
705                 710
```

<210> SEQ ID NO 30

-continued

<211> LENGTH: 3499
<212> TYPE: DNA
<213> ORGANISM: Homo sapiens

<400> SEQUENCE: 30
cgcggacccg gccggcccag gcccgcgccc gccgcggccc tgagaggccc cggcaggtcc 60
cggcccggcg gcggcagcca tggccggggg gccgggcccg ggggagcccg cagcccccgg 120
cgcccagcac ttcttgtacg aggtgccgcc ctgggtcatg tgccgcttct acaaagtgat 180
ggacgccctg gagcccgccg actggtgcca gttcgccgcc ctgatcgtgc gcgaccagac 240
cgagctgcgg ctgtgcgagc gctccgggca gcgcacggcc agcgtcctgt ggccctggat 300
caaccgcaac gcccgtgtgg ccgacctcgt gcacatcctc acgcacctgc agctgctccg 360
tgcgcgggac atcatcacag cctggcaccc tcccgccccg cttccgtccc caggcaccac 420
tgccccgagg cccagcagca tccctgcacc cgccgaggcc gaggcctgga gcccccggaa 480
gttgccatcc tcagcctcca ccttcctctc cccagctttt ccaggctccc agacccattc 540
agggcctgag ctcggcctgg tcccaagccc tgcttccctg tggcctccac cgccatctcc 600
agccccttct tctaccaagc caggcccaga gagctcagtg tccctcctgc agggagcccg 660 ccccttccg ttttgctggc ccctctgtga gatttcccgg ggcacccaca acttctcgga 720
ggagctcaag atcggggagg gtggctttgg gtgcgtgtac cgggcggtga tgaggaacac 780
ggtgtatgct gtgaagaggc tgaaggagaa cgctgacctg gagtggactg cagtgaagca 840
gagcttcctg accgaggtgg agcagctgtc caggtttcgt cacccaaaca ttgtggactt 900
tgctggctac tgtgctcaga acggcttcta ctgcctggtg tacggcttcc tgcccaacgg 960
ctccctggag gaccgtctcc actgccagac ccaggcctgc ccacctctct cctggcctca 1020
gcgactggac atccttctgg gtacagcccg ggcaattcag tttctacatc aggacagccc 1080
cagcctcatc catggagaca tcaagagttc caacgtcctt ctggatgaga ggctgacacc 1140
caagctggga gactttggcc tggcccggtt cagccgcttt gccgggtcca gccccagcca 1200
gagcagcatg gtggcccgga cacagacagt gcggggcacc ctggcctacc tgcccgagga 1260
gtacatcaag acgggaaggc tggctgtgga cacggacacc ttcagctttg gggtggtagt 1320
gctagagacc ttggctggtc agagggctgt gaagacgcac ggtgccagga ccaagtatct 1380
gaaagacctg gtggaagagg aggctgagga ggctggagtg gctttgagaa gcacccagag 1440
cacactgcaa gcaggtctgg ctgcagatgc ctgggctgct cccatcgcca tgcagatcta 1500
caagaagcac ctggacccca ggcccgggcc ctgcccacct gagctgggcc tgggcctggg 1560
ccagctggcc tgctgctgcc tgcaccgccg ggccaaaagg aggcctccta tgacccagga 1620
gaactcctac gtgtccagca ctggcagagc ccacagtggg gctgctccat ggcagcccct 1680
ggcagcgcca tcaggagcca gtgcccaggc agcagagcag ctgcagagag gccccaacca 1740
gcccgtggag agtgacgaga gcctaggcgg cctctctgct gccctgcgct cctggcactt 1800
gactccaagc tgccctctgg acccagcacc cctcagggag gccggctgtc ctcaggggga 1860
cacggcagga gaatcgagct gggggagtgg cccaggatcc cggcccacag ccgtggaagg 1920
actggccctt ggcagctctg catcatcgtc gtcagagcca ccgcagatta tcatcaaccc 1980
tgcccgacag aagatggtcc agaagctggc cctgtacgag gatggggccc tggacagcct 2040
gcagctgctg tcgtccagct ccctcccagg cttgggcctg gaacaggaca ggcaggggcc 2100
cgaagaaagt gatgaatttc agagctgatg tgttcacctg ggcagatccc ccaaatccgg 2160
aagtcaaagt tctcatggtc agaagttctc atggtgcacg agtcctcagc actctgccgg 2220

```
cagtgggggt gggggcccat gcccgcgggg gagagaagga ggtggccctg ctgttctagg   2280

ctctgtgggc ataggcaggc agagtggaac cctgcctcca tgccagcatc tgggggcaag   2340

gaaggctggc atcatccagt gaggaggctg gcgcatgttg ggaggctgct ggctgcacag   2400

acccgtgagg ggaggagagg ggctgctgtg caggggtgtg gagtagggag ctggctcccc   2460

tgagagccat gcagggcgtc tgcagcccag gcctctggca gcagctcttt gcccatctct   2520

ttggacagtg gccaccctgc acaatggggc cgacgaggcc tagggccctc ctacctgctt   2580

acaatttgga aaagtgtggc cgggtgcggt ggctcacgcc tgtaatccca gcactttggg   2640

aggccaaggc aggaggatcg ctggagccca gtaggtcaag accagccagg gcaacatgat   2700

gagaccctgt ctctgccaaa aaattttta aactattagc ctggcgtggt agcgcacgcc   2760

tgtggtccca gctgctgggg aggctgaagt aggaggatca tttatgcttg ggaggtcgag   2820

gctgcagtga gtcatgattg tatgactgca ctccagcctg ggtgacagag caagaccctg   2880

tttcaaaaag aaaaaccctg ggaaaagtga agtatggctg taagtctcat ggttcagtcc   2940

tagcaagaag cgagaattct gagatcctcc agaaagtcga gcagcaccca cctccaacct   3000

cgggccagtg tcttcaggct ttactgggga cctgcgagct ggcctaatgt ggtggcctgc   3060

aagccaggcc atccctgggc gccacagacg agctccgagc caggtcaggc ttcggaggcc   3120

acaagctcag cctcaggccc aggcactgat tgtggcagag gggccactac ccaaggtcta   3180

gctaggccca agacctagtt acccagacag tgagaagccc ctggaaggca gaaaagttgg   3240

gagcatggca gacagggaag ggaaacattt tcagggaaaa gacatgtatc acatgtcttc   3300

agaagcaagt caggtttcat gtaaccgagt gtcctcttgc gtgtccaaaa gtagcccagg   3360

gctgtagcac aggcttcaca gtgattttgt gttcagccgt gagtcacact acatgccccc   3420

gtgaagctgg gcattggtga cgtccaggtt gtccttgagt aataaaaacg tatgttgcaa   3480

taaaaaaaaa aaaaaaaaa                                                3499
```

<210> SEQ ID NO 31
<211> LENGTH: 682
<212> TYPE: PRT
<213> ORGANISM: Homo sapiens

<400> SEQUENCE: 31

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140
```

-continued

```
Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
    370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
            420                 425                 430

Tyr Leu Lys Asp Leu Val Glu Glu Glu Ala Glu Glu Ala Gly Val Ala
        435                 440                 445

Leu Arg Ser Thr Gln Ser Thr Leu Gln Ala Gly Leu Ala Ala Asp Ala
    450                 455                 460

Trp Ala Ala Pro Ile Ala Met Gln Ile Tyr Lys Lys His Leu Asp Pro
465                 470                 475                 480

Arg Pro Gly Pro Cys Pro Pro Glu Leu Gly Leu Gly Leu Gly Gln Leu
                485                 490                 495

Ala Cys Cys Cys Leu His Arg Arg Ala Lys Arg Arg Pro Pro Met Thr
            500                 505                 510

Gln Glu Asn Ser Tyr Val Ser Ser Thr Gly Arg Ala His Ser Gly Ala
        515                 520                 525

Ala Pro Trp Gln Pro Leu Ala Ala Pro Ser Gly Ala Ser Ala Gln Ala
    530                 535                 540

Ala Glu Gln Leu Gln Arg Gly Pro Asn Gln Pro Val Glu Ser Asp Glu
545                 550                 555                 560
```

```
Ser Leu Gly Gly Leu Ser Ala Ala Leu Arg Ser Trp His Leu Thr Pro
                565                 570                 575

Ser Cys Pro Leu Asp Pro Ala Pro Leu Arg Glu Ala Gly Cys Pro Gln
            580                 585                 590

Gly Asp Thr Ala Gly Glu Ser Ser Trp Gly Ser Gly Pro Gly Ser Arg
        595                 600                 605

Pro Thr Ala Val Glu Gly Leu Ala Leu Gly Ser Ser Ala Ser Ser Ser
    610                 615                 620

Ser Glu Pro Pro Gln Ile Ile Ile Asn Pro Ala Arg Gln Lys Met Val
625                 630                 635                 640

Gln Lys Leu Ala Leu Tyr Glu Asp Gly Ala Leu Asp Ser Leu Gln Leu
                645                 650                 655

Leu Ser Ser Ser Ser Leu Pro Gly Leu Gly Leu Glu Gln Asp Arg Gln
            660                 665                 670

Gly Pro Glu Glu Ser Asp Glu Phe Gln Ser
        675                 680


<210> SEQ ID NO 32
<211> LENGTH: 3352
<212> TYPE: DNA
<213> ORGANISM: Homo sapiens

<400> SEQUENCE: 32

cgcggacccg gccggcccag gcccgcgccc gccgcggccc tgagaggccc cggcaggtcc      60

cggcccggcg gcggcagcca tggccggggg gccgggcccg ggggagcccg cagcccccgg     120

cgcccagcac ttcttgtacg aggtgccgcc ctgggtcatg tgccgcttct acaaagtgat     180

ggacgccctg gagcccgccg actggtgcca gttcgccgcc ctgatcgtgc gcgaccagac     240

cgagctgcgg ctgtgcgagc gctccgggca gcgcacggcc agcgtcctgt ggccctggat     300

caaccgcaac gcccgtgtgg ccgacctcgt gcacatcctc acgcacctgc agctgctccg     360

tgcgcgggac atcatcacag cctggcaccc tcccgccccg cttccgtccc caggcaccac     420

tgccccgagg cccagcagca tccctgcacc cgccgaggcc gaggcctgga gcccccggaa     480

gttgccatcc tcagcctcca ccttcctctc cccagctttt ccaggctccc agacccattc     540

agggcctgag ctcggcctgg tcccaagccc tgcttccctg tggcctccac cgccatctcc     600

agccccttct tctaccaagc caggcccaga gagctcagtg tccctcctgc agggagcccg     660

ccccttttccg ttttgctggc ccctctgtga gatttcccgg ggcacccaca acttctcgga     720

ggagctcaag atcggggagg gtggctttgg gtgcgtgtac cgggcggtga tgaggaacac     780

ggtgtatgct gtgaagaggc tgaaggagaa cgctgacctg gagtggactg cagtgaagca     840

gagcttcctg accgaggtgg agcagctgtc caggtttcgt cacccaaaca ttgtggactt     900

tgctggctac tgtgctcaga acggcttcta ctgcctggtg tacggcttcc tgcccaacgg     960

ctccctggag gaccgtctcc actgccagac ccaggcctgc ccacctctct cctggcctca    1020

gcgactggac atccttctgg gtacagcccg ggcaattcag tttctacatc aggacagccc    1080

cagcctcatc catggagaca tcaagagttc caacgtcctt ctggatgaga ggctgacacc    1140

caagctggga gactttggcc tggcccggtt cagccgcttt gccgggtcca gccccagcca    1200

gagcagcatg gtggcccgga cacagacagt gcggggcacc ctggcctacc tgcccgagga    1260

gtacatcaag acgggaaggc tggctgtgga cacggacacc ttcagctttg ggtggtagt     1320

gctagagacc ttggctggtc agagggctgt gaagacgcac ggtgccagga ccaagtatct    1380

ggtgtacgag aggctagaga agctgcaggc agtggtggcg gggtgcccg ggcattcgga     1440
```

ggccgccagc tgcatccccc cttccccgca ggagaactcc tacgtgtcca gcactggcag 1500
agcccacagt ggggctgctc catggcagcc cctggcagcg ccatcaggag ccagtgccca 1560
ggcagcagag cagctgcaga gaggccccaa ccagcccgtg gagagtgacg agagcctagg 1620
cggcctctct gctgccctgc gctcctggca cttgactcca agctgccctc tggacccagc 1680
acccctcagg gaggccggct gtcctcaggg ggacacggca ggagaatcga gctgggggag 1740
tggcccagga tcccggccca cagccgtgga aggactggcc cttggcagct ctgcatcatc 1800
gtcgtcagag ccaccgcaga ttatcatcaa ccctgcccga cagaagatgg tccagaagct 1860
ggccctgtac gaggatgggg ccctggacag cctgcagctg ctgtcgtcca gctccctccc 1920
aggcttgggc ctggaacagg acaggcaggg gcccgaagaa agtgatgaat ttcagagctg 1980
atgtgttcac ctgggcagat cccccaaatc cggaagtcaa agttctcatg gtcagaagtt 2040
ctcatggtgc acgagtcctc agcactctgc cggcagtggg ggtgggggcc catgcccgcg 2100
ggggagagaa ggaggtggcc ctgctgttct aggctctgtg ggcataggca ggcagagtgg 2160
aaccctgcct ccatgccagc atctgggggc aaggaaggct ggcatcatcc agtgaggagg 2220
ctggcgcatg ttgggaggct gctggctgca cagacccgtg aggggaggag aggggctgct 2280
gtgcaggggt gtggagtagg gagctggctc ccctgagagc catgcagggc gtctgcagcc 2340
caggcctctg gcagcagctc tttgcccatc tctttggaca gtggccaccc tgcacaatgg 2400
ggccgacgag gcctagggcc ctcctacctg cttacaattt ggaaaagtgt ggccgggtgc 2460
ggtggctcac gcctgtaatc ccagcacttt gggaggccaa ggcaggagga tcgctggagc 2520
ccagtaggtc aagaccagcc agggcaacat gatgagaccc tgtctctgcc aaaaaatttt 2580
ttaaactatt agcctggcgt ggtagcgcac gcctgtggtc ccagctgctg gggaggctga 2640
agtaggagga tcatttatgc ttgggaggtc gaggctgcag tgagtcatga ttgtatgact 2700
gcactccagc ctgggtgaca gagcaagacc ctgtttcaaa aagaaaaacc ctgggaaaag 2760
tgaagtatgg ctgtaagtct catggttcag tcctagcaag aagcgagaat tctgagatcc 2820
tccagaaagt cgagcagcac ccacctccaa cctcgggcca gtgtcttcag gctttactgg 2880
ggacctgcga gctggcctaa tgtggtggcc tgcaagccag gccatccctg ggcgccacag 2940
acgagctccg agccaggtca ggcttcggag gccacaagct cagcctcagg cccaggcact 3000
gattgtggca gaggggccac tacccaaggt ctagctaggc ccaagaccta gttacccaga 3060
cagtgagaag cccctggaag gcagaaaagt tgggagcatg gcagacaggg aagggaaaca 3120
ttttcaggga aaagacatgt atcacatgtc ttcagaagca agtcaggttt catgtaaccg 3180
agtgtcctct tgcgtgtcca aaagtagccc agggctgtag cacaggcttc acagtgattt 3240
tgtgttcagc cgtgagtcac actacatgcc cccgtgaagc tgggcattgg tgacgtccag 3300
gttgtccttg agtaataaaa acgtatgttg caataaaaaa aaaaaaaaaa aa 3352

<210> SEQ ID NO 33
<211> LENGTH: 633
<212> TYPE: PRT
<213> ORGANISM: Homo sapiens

<400> SEQUENCE: 33

Met Ala Gly Gly Pro Gly Pro Gly Glu Pro Ala Ala Pro Gly Ala Gln
1 5 10 15

His Phe Leu Tyr Glu Val Pro Pro Trp Val Met Cys Arg Phe Tyr Lys
20 25 30

-continued

```
Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
        275                 280                 285

Gly Phe Leu Pro Asn Gly Ser Leu Glu Asp Arg Leu His Cys Gln Thr
    290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
    370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
            420                 425                 430

Tyr Leu Val Tyr Glu Arg Leu Glu Lys Leu Gln Ala Val Val Ala Gly
        435                 440                 445

Val Pro Gly His Ser Glu Ala Ala Ser Cys Ile Pro Pro Ser Pro Gln
```

-continued

```
    450                 455                 460

Glu Asn Ser Tyr Val Ser Ser Thr Gly Arg Ala His Ser Gly Ala Ala
465                 470                 475                 480

Pro Trp Gln Pro Leu Ala Ala Pro Ser Gly Ala Ser Ala Gln Ala Ala
                485                 490                 495

Glu Gln Leu Gln Arg Gly Pro Asn Gln Pro Val Glu Ser Asp Glu Ser
            500                 505                 510

Leu Gly Gly Leu Ser Ala Ala Leu Arg Ser Trp His Leu Thr Pro Ser
        515                 520                 525

Cys Pro Leu Asp Pro Ala Pro Leu Arg Glu Ala Gly Cys Pro Gln Gly
    530                 535                 540

Asp Thr Ala Gly Glu Ser Ser Trp Gly Ser Gly Pro Gly Ser Arg Pro
545                 550                 555                 560

Thr Ala Val Glu Gly Leu Ala Leu Gly Ser Ser Ala Ser Ser Ser Ser
                565                 570                 575

Glu Pro Pro Gln Ile Ile Ile Asn Pro Ala Arg Gln Lys Met Val Gln
            580                 585                 590

Lys Leu Ala Leu Tyr Glu Asp Gly Ala Leu Asp Ser Leu Gln Leu Leu
        595                 600                 605

Ser Ser Ser Ser Leu Pro Gly Leu Gly Leu Glu Gln Asp Arg Gln Gly
    610                 615                 620

Pro Glu Glu Ser Asp Glu Phe Gln Ser
625                 630


<210> SEQ ID NO 34
<211> LENGTH: 23
<212> TYPE: RNA
<213> ORGANISM: Artificial sequence
<220> FEATURE:
<223> OTHER INFORMATION: IL-1 alpha miRNA

<400> SEQUENCE: 34

uguaaacauc cuacacucuc agc                                            23


<210> SEQ ID NO 35
<211> LENGTH: 21
<212> TYPE: RNA
<213> ORGANISM: Artificial sequence
<220> FEATURE:
<223> OTHER INFORMATION: IL-1 alpha miRNA

<400> SEQUENCE: 35

uguaaacauc cuacacucag c                                              21


<210> SEQ ID NO 36
<211> LENGTH: 23
<212> TYPE: RNA
<213> ORGANISM: Artificial sequence
<220> FEATURE:
<223> OTHER INFORMATION: IL-1 alpha miRNA

<400> SEQUENCE: 36

uguaaacauc cucgacugga agc                                            23


<210> SEQ ID NO 37
<211> LENGTH: 22
<212> TYPE: RNA
<213> ORGANISM: Artificial sequence
<220> FEATURE:
<223> OTHER INFORMATION: IL-1 alpha miRNA
```

-continued

<400> SEQUENCE: 37
uggcucaguu cagcaggaac ag 22

<210> SEQ ID NO 38
<211> LENGTH: 22
<212> TYPE: RNA
<213> ORGANISM: Artificial sequence
<220> FEATURE:
<223> OTHER INFORMATION: IL-1R1 miRNA

<400> SEQUENCE: 38
uauggcuuuu cauuccuaug ug 22

<210> SEQ ID NO 39
<211> LENGTH: 20
<212> TYPE: RNA
<213> ORGANISM: Artificial sequence
<220> FEATURE:
<223> OTHER INFORMATION: IL-1R1 miRNA

<400> SEQUENCE: 39
ccucugggcc cuuccuccag 20

<210> SEQ ID NO 40
<211> LENGTH: 22
<212> TYPE: RNA
<213> ORGANISM: Artificial sequence
<220> FEATURE:
<223> OTHER INFORMATION: IL-1R1 miRNA

<400> SEQUENCE: 40
uggacggaga acugauaagg gu 22

<210> SEQ ID NO 41
<211> LENGTH: 21
<212> TYPE: RNA
<213> ORGANISM: Artificial sequence
<220> FEATURE:
<223> OTHER INFORMATION: IL-1R1 miRNA

<400> SEQUENCE: 41
acagcaggca cagacaggca g 21

<210> SEQ ID NO 42
<211> LENGTH: 22
<212> TYPE: RNA
<213> ORGANISM: Artificial sequence
<220> FEATURE:
<223> OTHER INFORMATION: IL-1R1 miRNA

<400> SEQUENCE: 42
gugaaauguu uaggaccacu ag 22

<210> SEQ ID NO 43
<211> LENGTH: 21
<212> TYPE: RNA
<213> ORGANISM: Artificial sequence
<220> FEATURE:
<223> OTHER INFORMATION: IL-1R1 miRNA

<400> SEQUENCE: 43
gccccugggc cuauccuaga a 21

<210> SEQ ID NO 44
<211> LENGTH: 22

-continued

```
<212> TYPE: RNA
<213> ORGANISM: Artificial sequence
<220> FEATURE:
<223> OTHER INFORMATION: IL-1R1 miRNA

<400> SEQUENCE: 44

uccuucauuc caccggaguc ug                                              22


<210> SEQ ID NO 45
<211> LENGTH: 15
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Wherein Xaa is 2-azetidine-1-carboxylic acid.

<400> SEQUENCE: 45

Phe Glu Trp Thr Pro Gly Trp Tyr Gln Xaa Tyr Ala Leu Pro Leu
1               5                   10                  15
```

METHODS FOR REDUCING CORNEAL NERVES DAMAGE, CORNEAL LYMPHANGIOGENESIS OR IMMUNITY TO CORNEAL ANTIGENS IN DRY-EYE ASSOCIATED OCULAR SURFACE DISEASES BY IL-1RA

RELATED APPLICATIONS

This application claims the benefit of U.S. Ser. No. 61/143,561, filed Jan. 9, 2009, the contents of which are incorporated by reference herein in their entirety.

FIELD OF THE INVENTION

This invention relates generally to the field of ophthalmology.

BACKGROUND OF THE INVENTION

Corneal epithelial damage can lead to chronic ocular surface disease. The mechanisms by which this occurs have not been elucidated, making the development of treatments that address the cause rather than the symptoms of chronic ocular surface disease difficult, if not impossible. As such, there has been a long-felt need in the art for the discovery of these mechanisms and for the development of compositions and methods of treatment.

SUMMARY OF THE INVENTION

The invention is based on the surprising discovery that IL-1 inhibition leads to corneal nerve regeneration. Moreover, the invention provides compositions and methods for treating neurotrophic dry eye disease by reducing damage to and regenerating corneal nerves. Nerve damage and increased immune activity within the cornea complete a vicious cycle of events, along with corneal epithelial damage, that would perpetuate itself and lead to chronic ocular surface disorders, but for the intervention of the treatments described herein. Neurotrophic dry eye (a neuropathic condition) is distinguished from other types of dry eye by a reduction or loss of corneal nerve tissue. For example, neurotrophic dry eye is characterized by a reduction or loss of at least about 10%, 25%, 50%, 75%, or more of corneal nerve tissue or corneal nerve fiber length compared to a normal condition.

The invention provides a method for protecting or treating corneal nerves in a subject in need thereof, including the steps of: (a) identifying a subject with corneal nerve damage or loss; and (b) locally administering to the cornea of the subject a composition that inhibits an activity of an inflammatory cytokine (e.g., IL-1 or a combination of IL-1 and IL-17), thereby enhancing corneal nerve regeneration and reducing the development of abnormalities in nerve morphology or density. Preferably, the subject has not been diagnosed as having meibomian gland dysfunction (MGD), e.g., posterior blepharitis.

In one aspect of the above method, the subject is identified as having corneal nerve damage or loss that results from a congenital defect, disease, trauma, medical or surgical procedure. In another aspect of the above method, the subject is identified as having corneal nerve damage or loss that results from neurotrophic keratitis, herpes simplex, zoster keratitis, diabetes mellitus, trigeminal nerve damage, orbital or head surgery, head trauma, aneurysm, intracranial neurologic disease, keratorefractive procedures, photorefractive keratectomy (PRK), laser in situ keratomileusis (LASIK), congenital defect, ocular surface disease, dry eye syndrome, a non-ophthalmic disorder, a non-ophthalmic procedure, peripheral neuropathy, or diabetic neuropathy.

The invention further provides a method for minimizing or preventing damage or loss of corneal nerves in a subject in need thereof, including the steps of: (a) identifying the subject at risk of developing corneal nerve damage or loss; and (b) locally administering to the cornea of the subject a composition that inhibits an activity of an inflammatory interleukin-1 or interleukin-17 cytokine prior to development of nerve damage or loss, thereby decreasing nerve degeneration and reducing or preventing the development of abnormalities in nerve morphology or density.

In one aspect of the above method, the subject is identified as being at risk of exposure to corneal nerve damage or loss that could result from disease, trauma, or a medical procedure. In another aspect of the above method, the subject is identified as being at risk of exposure to corneal nerve damage or loss that could result from neurotrophic keratitis, herpes simplex keratitis, herpes zoster keratitis, diabetes mellitus, trigeminal nerve damage, orbital or head surgery, head trauma, aneurysm, intracranial neurologic disease, keratorefractive procedures, photorefractive keratectomy (PRK), laser in situ keratomileusis (LASIK), ocular surface disease, dry eye syndrome, a non-ophthalmic disorder, a non-ophthalmic procedure, peripheral neuropathy, or diabetic neuropathy.

In certain embodiments, the above methods further include the step of identifying a subject with a sign or symptom of corneal nerve damage or loss. For example, a sign of corneal nerve damage or loss is a decrease of corneal innervation or sensation, a reduction in the number of nerve fibers or bundles innervating the cornea, death of neurons innervating the cornea, a decrease or loss of neurotransmitter release, a decrease or loss of nerve growth factor release, abnormal tearing reflexes, abnormal blink reflexes, abnormal nerve morphology, appearance of abnormal nerve sprouts, abnormal tortuosity, increased bead-like nerve formations, thinning of nerve fiber bundles, or thickening of nerve fiber bundles. For example, a symptom of corneal nerve damage or loss is abnormal tear production or dryness, abnormal blinking, and difficulty or loss of ability to focus, decreased or lost visual acuity, or decreased or lost corneal sensitivity. In one aspect of the above methods, the activity includes binding of an inflammatory IL-1 cytokine to an IL-1 receptor. Compositions of the above methods that inhibit binding of an inflammatory IL-1 cytokine to an IL-1 receptor include an amino acid sequence of SEQ ID NO: 15 or SEQ ID NO: 16. Compositions optionally include inhibitors of IL-17 activity, e.g., compounds that inhibit IL-17 binding to its receptor, or compounds that inhibit cytokines critical for generation of T helper-17/IL-17 response, such as inhibitors of IL-6 or inhibitors of IL-23. Preferably, the compositions do not include generic, broad spectrum immunosuppressive agents, such as cyclosporine A (CsA), as such non-specific suppressors of inflammation do not regenerate corneal nerves.

In each of the methods described herein, the composition is present in a concentration of 0.1-10% (weight/volume or w/v). Alternatively, the composition is present in a concentration of 1.0% (mg/ml), 1.5% (mg/ml), 2.0% (mg/ml), 2.5% (mg/ml), 3.0% (mg/ml), 3.5% (mg/ml), 4.0% (mg/ml), 4.5% (mg/ml), 5.0% (mg/ml), 5.5% (mg/ml), 6.0% (mg/ml), 6.5% (mg/ml), 7.0% (mg/ml), 7.5% (mg/ml), 8.0% (mg/ml), 8.5% (mg/ml), 9.0% (mg/ml), 9.5% (mg/ml), 10.0% (mg/ml), or any percentage point in between. In a preferred embodiment, the composition is present in a concentration of 2.5% (mg/ml) or 5% (mg/ml). For example, the composition is present in a concentration of 25 mg/ml or 50 mg/ml. Exemplary formulations contain an inhibitory composition present in a concentration of 2.5% (25 mg/ml) or 5% (50 mg/ml).

The form of a composition of the above methods is a solid, a paste, an ointment, a gel, a liquid, an aerosol, a mist, a polymer, a film, an emulsion, or a suspension. The composition is administered topically. In a preferred embodiment, the above methods do not include systemic administration or substantial dissemination to non-ocular tissue. In certain embodiments of the above methods, the composition further includes a compound selected from the group consisting of a physiological acceptable salt, poloxamer analogs with carbopol, carbopol/HPMC, carbopol-methyl cellulose, a mucolytic agent, carboxymethylcellulose (CMC), hyaluronic acid, cyclodextrin, and petroleum. An exemplary mucolytic agent is N-acetyl cysteine. In a preferred embodiment, the composition further includes carboxymethylcellulose (CMC).

Compositions of the above methods inhibit the transcription, transcript stability, translation, modification, localization, secretion, or function of a polynucleotide or polypeptide encoding an inflammatory interleukin-1 cytokine or an IL-1 receptor. In certain embodiments, a composition of the above methods includes a polynucleotide, a polypeptide, an antibody, or a small molecule. Alternatively, or in addition, a composition of the above methods includes a morpholino antisense oligonucleotide, microRNA (miRNA), short hairpin RNA (shRNA), or short interfering RNA (siRNA).

The invention provides a method for reducing or treating corneal lymphangiogenesis in a subject in need thereof, including the steps of: (a) identifying a subject with corneal lymphangiogenesis; and (b) locally administering to the cornea of the subject a composition that inhibits an activity of an inflammatory interleukin-1 cytokine, thereby inhibiting the ability of lymphatic vessels to expand within or invade corneal tissue and reducing or treating corneal lymphangiogenesis.

The invention provides a method for minimizing or preventing corneal lymphangiogenesis in a subject in need thereof, including the steps of: (a) identifying a subject at risk of developing lymphangiogenesis onset; and (b) locally administering to the cornea of the subject a composition that inhibits an activity of an inflammatory interleukin-1 cytokine prior to the development, thereby inhibiting the ability of lymphatic vessels to form or expand within, or to invade corneal tissue and minimizing or preventing corneal lymphangiogenesis.

The invention provides a method for reducing or treating the induction of immunity in a cornea of a subject in need thereof, including the steps of: (a) identifying a subject with an induction of immunity; and (b) locally administering to the cornea of the subject a composition that inhibits an activity of an inflammatory interleukin-1 cytokine, thereby inhibiting the ability of lymphatic vessels to expand within or to invade corneal tissue and reducing or treating the induction of immunity, wherein the lymphatic vessels permit the transport of immune cells between the corneal tissue and lymph nodes and the initiation of an immune response.

The invention provides a method for minimizing or preventing induction of immunity in a cornea of a subject in need thereof, including the steps of: (a) identifying the subject at risk of developing an immunity; and (b) locally administering to the cornea of the subject a composition that inhibits an activity of an inflammatory interleukin-1 cytokine prior to the development, thereby inhibiting the ability of lymphatic vessels to expand within or to invade corneal tissue and minimizing or preventing induction of immunity, wherein the lymphatic vessels permit the transport of immune cells between the corneal tissue and lymph nodes and the initiation of an immune response.

The invention provides a method for reducing or treating an autoimmune condition affecting a corneal tissue of a subject in need thereof, including the steps of: (a) identifying a subject with the autoimmune condition; and (b) locally administering to the cornea of the subject a composition that inhibits an activity of an inflammatory interleukin-1 cytokine, thereby inhibiting the ability of lymphatic vessels to expand within or to invade corneal tissue and reducing or treating the autoimmune condition, wherein the lymphatic vessels permit the transport of immune cells between the corneal tissue and lymph nodes and the initiation of an immune response.

The invention provides a method for minimizing or preventing the development of an autoimmune condition affecting a corneal tissue of a subject in need thereof, including the steps of: (a) identifying a subject at risk of developing said autoimmune condition; and (b) locally administering to the cornea of the subject a composition that inhibits an activity of an inflammatory interleukin-1 cytokine prior to the development, thereby inhibiting the ability of lymphatic vessels to expand within or to invade corneal tissue and minimizing or preventing the development of the autoimmune condition, wherein the lymphatic vessels permit the transport of immune cells between said corneal tissue and lymph nodes and the initiation of an immune response.

In certain embodiments of the above methods, the subject has a dry-eye associated ocular surface disease. Alternatively, or in addition, the subject is at risk of developing a dry-eye associated ocular surface disease.

The ability of lymphatic vessels to expand within or to invade corneal tissue encompasses the potential or actual growth, expansion, elaboration, splitting, or remodeling of lymphatic vessels either within a corneal tissue or from a non-corneal tissue (such as the adjacent limbus) into corneal tissue. The phrase "lymphatic vessels permit the transport of immune cells" describes the unidirectional or bidirectional movement or deposition of an immune cell between a corneal tissue and a non-corneal tissue, preferably, a lymph node or other sites in the lymphoid compartment. Exemplary immune cells is include, but are not limited to, T cells, B cells, dendritic cells, macrophages, monocytes, and natural killer (NK) cells.

In one aspect of the above methods, the activity includes binding of an inflammatory IL-1 cytokine to an IL-1 receptor. Compositions of the above methods that inhibit binding of an inflammatory IL-1 cytokine to an IL-1 receptor include an amino acid sequence of SEQ ID NO: 15 or SEQ ID NO: 16.

The form of a composition of the above methods is a solid, a paste, an ointment, a gel, a liquid, an aerosol, a mist, a polymer, a film, an emulsion, or a suspension. The composition is administered topically. In a preferred embodiment, the above methods do not include systemic administration or substantial dissemination to non-ocular tissue. In certain embodiments of the above methods, the composition further includes a compound selected from the group consisting of a physiological acceptable salt, poloxamer analogs with carbopol, carbopol/HPMC, carbopol-methyl cellulose, a mucolytic agent, carboxymethylcellulose (CMC), hyaluronic acid, cyclodextrin, and petroleum. An exemplary mucolytic agent is N-acetyl cysteine. In a preferred embodiment, the composition further includes carboxymethylcellulose (CMC).

Compositions of the above methods inhibit the transcription, transcript stability, translation, modification, localization, secretion, or function of a polynucleotide or polypeptide encoding an inflammatory interleukin-1 cytokine or an IL-1 receptor. In certain embodiments, a composition of the above methods includes a polynucleotide, a polypeptide, an antibody, or a small molecule. Alternatively, or in addition, a composition of the above methods includes a morpholino antisense oligonucleotide, microRNA (miRNA), short hairpin RNA (shRNA), or short interfering RNA (siRNA).

In certain embodiments of the above methods, the activity includes binding of an inflammatory IL-1 cytokine to an IL-1 receptor. Furthermore, compositions of the above methods that inhibit binding of an inflammatory IL-1 cytokine to an IL-1 receptor include the amino acid of SEQ ID NO: 15 or SEQ ID NO: 16. In certain embodiments, compositions of the above methods are present in a concentration of 0.1-10% (mg/ml). Alternatively, the composition is present in a concentration of 1.0% (mg/ml), 1.5% (mg/ml), 2.0% (mg/ml), 2.5% (mg/ml), 3.0% (mg/ml), 3.5% (mg/ml), 4.0% (mg/ml), 4.5% (mg/ml), 5.0% (mg/ml), 5.5% (mg/ml), 6.0% (mg/ml), 6.5% (mg/ml), 7.0% (mg/ml), 7.5% (mg/ml), 8.0% (mg/ml), 8.5% (mg/ml), 9.0% (mg/ml), 9.5% (mg/ml), 10.0% (mg/ml), or any percentage point in between. In a preferred embodiment, the composition is present in a concentration of 2.5% (mg/ml) or 5% (mg/ml). In another preferred embodiment, the composition is present in a concentration of 25 mg/ml or 50 mg/ml. In a further preferred embodiment, the composition is present in a concentration of 2.5% (25 mg/ml) or 5% (50 mg/ml).

In one aspect of the invention, the form of the compositions of the above methods is a solid, a paste, an ointment, a gel, a liquid, an aerosol, a mist, a polymer, a film, an emulsion, or a suspension.

Compositions of the above methods are administered topically. The above methods do not include systemic administration or substantial dissemination of the composition to non-ocular tissue.

In certain embodiments, compositions of the above methods further include a compound selected from the group consisting of a physiological acceptable salt, poloxamer analogs with carbopol, carbopol/HPMC, carbopol-methyl cellulose, N-acetyl cysteine, carboxymethylcellulose (CMC), hyaluronic acid, cyclodextrin, and petroleum. Preferably, the composition further includes N-acetyl cysteine or carboxymethylcellulose (CMC).

Alternatively, compositions of the above methods inhibit or enhance the transcription, transcript stability, translation, modification, localization, secretion, or function of a polynucleotide or polypeptide encoding the IL-1 receptor, type 2 (IL-1R2). IL-1R2 binds IL-1 and can inhibit the function of IL-1R1. Thus, in one embodiment, enhancement of IL-1R2 function provides another mechanism by which IL-1R1 activity is inhibited. In this same embodiment, inhibition of an antagonist of IL-1R2, specifically, IL-1Ra3, inhibits IL-1R1 function. Thus, the composition alone, or in combination with an enhancer of IL-1R2, inhibits the transcription, transcript stability, translation, modification, localization, secretion, or function of a polynucleotide or polypeptide encoding IL-1Ra3, SEQ ID NO: 22 or 23. Alternatively, in an embodiment wherein IL-1R2 receptor function augments the activity of IL-1R1, the composition contains one or more regions of a polynucleotide or polypeptide encoding IL-1Ra3 to augment IL-1R2 inhibition. Furthermore, the composition of this embodiment comprises the whole polynucleotide or polypeptide encoding IL-1Ra3.

Compositions of the methods of the invention include a polynucleotide, a polypeptide, an antibody, a compound, or a small molecule with means to inhibit the transcription, transcript stability, translation, modification, localization, secretion, or function of a polynucleotide or polypeptide encoding an accessory protein of an IL-1 Receptor. For example, this IL-1 receptor accessory protein is IL-1RAP, which directly binds IL-1 and IL-1R1, and is defined by the polynucleotide sequence of SEQ ID NO: 24 or 26 and the polypeptide sequence of SEQ ID NO: 25 or 27. IL-1RAP belongs to a signaling complex that is required for signal transduction from IL-1R1. Thus, inhibition of IL-1RAP antagonizes IL-1R1 function.

In another embodiment, compositions of the methods of the invention include a polynucleotide, a polypeptide, an antibody, a compound, or a small molecule with means to inhibit the transcription, transcript stability, translation, modification, localization, secretion, or function of a polynucleotide or polypeptide encoding an associated kinase to an IL-1 receptor. For example, IL-1 receptor-associated kinase is IRAK1. IRAK1 is a downstream signaling effector that leads to transcriptional events associated with escalating inflammatory responses and is defined by the polynucleotide sequence of SEQ ID NO: 28, 30, or 32 and the polypeptide sequence of SEQ ID NO: 29, 31, or 33. Upon IL-1 receptor binding by IL-1, IRAK1 is recruited to the receptor complex, becomes hyperphosphorylated, and participates in the formation of a new protein complex consisting of hyperphosphorylated IRAK1 and TRAF6. The formation of this IRAK1/TRAF6 complex is a prerequisite for tumor necrosis factor (TNF) associated factor 6 (TRAF6)-mediated activation of nuclear factor-κB (NF-κB). Thus, the modification of the expression or function of any component of the above-delineated signaling cascade indicates a binding event between IL-1 to an IL-1 receptor.

Compositions of the methods of the invention include a polynucleotide, a polypeptide, an antibody, or a small molecule that binds or modifies the function of IL-1α, IL-1b, IL-1R1, IL-1R2, IL-1Ra3, IL-1RAP, IL-17, or IRAK1. Moreover the compositions include morpholino antisense oligonucleotides, microRNAs (miRNAs), short hairpin RNA (shRNA), or short interfering RNA (siRNA) to silence gene expression. Exemplary compounds to be adapted for topical administration include, but are not limited to, anakinra/Kineret® (recombinant human IL-1Ra, rhIL-1Ra, and SEQ ID NO: 15 and 16), IL-1R antisense oligomers (U.S. Patent No. 2005033694), IL-1Ra-like nucleic acid molecule (Amgen, U.S. Patent No. 2001041792), and polynucleotide encoding a soluble IL-1R accessory molecule (Human Genome Sciences, U.S. Pat. No. 6,974,682).

Compositions of the methods of the invention include microRNA molecules adapted for topical administration to the cornea in order to silence gene expression. Exemplary miRNAs that bind to human IL-1α include, but are not limited to, miR-30c (SEQ ID NO: 34), miR-30b (SEQ ID NO: 35), miR-30a-5p (SEQ ID NO: 36), and miR-24 (SEQ ID NO: 37). Exemplary miRNAs (and corresponding sequences) that bind to human IL-1R1 include, but are not limited to, miR-135b (SEQ ID NO: 38), miR-326 (SEQ ID NO: 39), miR-184 (SEQ ID NO: 40), miR-214 (SEQ ID NO: 41), miR-203 (SEQ ID NO: 42), miR-331 (SEQ ID NO: 43), and miR-205 (SEQ ID NO: 44).

Exemplary polypeptides to be adapted for topical administration to the cornea include, but are not limited to, anakinra/Kineret® (recombinant human IL-1Ra, rhIL-1Ra, and SEQ ID NO: 15 and 16), AF12198 (binds human IL-1R1, Ac-FEWTPGWYQJYALPL-NH2 where J represents the unnatural amino acid, 2-azetidine-1-carboxylic acid, SEQ ID NO: 45), IL-1R and IL-1RAP peptide antagonists (U.S. Patent No. 20060094663), IL-1R accessory molecule polypeptides (U.S. Patent No. 20050171337), IL-1Ra peptides (U.S. Patent No. 2005105830), and IL-1Ra-related peptides (Amgen, U.S. Patent No. 2001042304).

Exemplary antibodies to be adapted for topical administration to the cornea include, but are not limited to, IL-1 TRAP (inline fusion double chain protein of IL1R-gp130 with hIgGFc, Regeneron, U.S. Pat. No. 6,927,044), anti-IL-1α (U.S. Patent No. 20030026806), anti-IL-1β (U.S. Patent No. 20030026806 and Yamasaki et al. Stroke. 1995; 26:676-681), and humanized monoclonal anti-IL-1R (Amgen, U.S. Patent No. 2004022718 and Roche, U.S. Patent No. 2005023872).

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecule inhibitors can be synthetically engineered to consist of a fragment, or small portion, or a longer amino acid chain to fill a binding pocket of an enzyme. Typically small molecules are less than one kilodalton. An exemplary small molecule to be adapted for topical administration to the cornea is ZnPP (IL-1 blocker zinc protoporphyrin, naturally-occurring metabolite, Yamasaki et al. Stroke. 1995; 26:676-681).

Compositions of the methods of the invention include a polynucleotide, a polypeptide, an antibody, or a small molecule that binds or modifies the function of IL-1α, IL-1b, IL-1Ra, IL-1R1, IL-1R2, IL-1Ra3, IL-1RAP, IL-17, or IRAK1, administered topically with a pharmaceutically appropriate carrier. Delivery methods for polynucleotide compositions include, but are not limited to, liposomes, receptor-mediated delivery systems, naked DNA, and engineered viral vectors such as herpes viruses, retroviruses, adenoviruses and adeno-associated viruses, among others. Polynucleotide compositions are administered topically with a pharmaceutically acceptable liquid carrier, e.g., a liquid carrier, which is aqueous or partly aqueous. Alternatively, polynucleotide sequences within the composition are associated with a liposome (e.g., a cationic or anionic liposome).

A number of methods have been developed for delivering short DNA or RNA sequences into cells; e.g., polynucleotide molecules can be contacted directly onto the tissue site, or modified polynucleotide molecules, designed to specifically target desired cell types (e.g., sequences linked to peptides or antibodies that specifically bind receptors or antigens expressed on the target cell surface).

A preferred approach uses a recombinant DNA construct in which the short polynucleotide sequence is placed under the control of a strong polymerase III or polymerase II promoter. The use of such a construct will result in the transcription of sufficient amounts of polynucleotide that will form complementary base pairs with the endogenous transcripts of nucleic acids of the invention and thereby prevent translation of endogenous mRNA transcripts. The invention encompasses the construction of a short polynucleotide using the complementary strand as a template. For example, a vector can be introduced in vivo such that it is taken up by a cell and directs the transcription of an interfering RNA or precursor to a double stranded RNA molecule. Alternatively, the template for the short polynucleotide transcript is placed under the transcriptional control of a cell-type specific promoter or other regulatory element. Thus, diffusion or absorption of a topically administered composition beyond the cornea does not cause deleterious or systemic side effects. The vector remains episomal or becomes chromosomally integrated, as long as it can be transcribed to produce the desired polynucleotide. Vectors are constructed by recombinant DNA technology methods standard in the art. Vectors can be plasmid, viral, or others known in the art, used for replication and expression in mammalian cells. Expression of the sequence encoding the short polynucleotide can be placed under the control of any promoter known in the art to act in mammalian, preferably human cells. Promoters are inducible or constitutive. Exemplary promoters include, but are not limited to: the SV40 early promoter region (Bernoist et al., Nature 290: 304, 1981); the promoter contained in the 3' long terminal repeat of Rous sarcoma virus (Yamamoto et al., Cell, 22:787-797, 1988); the herpes thymidine kinase promoter (Wagner et al., Proc. Natl. Acad. Sci. USA, 78:1441, 1981); or the regulatory sequences of the metallothionein gene (Brinster et al., Nature, 296:39, 1988). Polypeptide compositions are associated with liposomes alone or in combination with receptor-mediated delivery systems, to enable transport across the plasma membrane. Polypeptide compositions are soluble or membrane-bound. An exemplary receptor-mediated delivery system involves fusion of a low-density or very-low-density lipoprotein containing particle or vesicle to the low-density lipoprotein (LDL) receptor (LDLR) as observed with Hepatitis C Virus (HCV) infection and HCV-mediated drug delivery methods.

Compositions of the methods of the invention include one or more extracellular or intracellular antibodies, also called intrabodies, raised against one or more of the following: IL-1α, IL-1b, IL-1Ra, IL-1R1, IL-1R2, IL-1Ra3, IL-1RAP, or IRAK1. Extracellular antibodies are topically administered with a pharmacologically appropriate aqueous or non-aqueous carrier. Sequences encoding intracellular antibodies are subcloned into a viral or mammalian expression vector, packed in a lipophilic device to facilitate transport across the plasma membrane, and topically administered to the cornea with a pharmacologically appropriate aqueous or non-aqueous carrier. Once inside the plasma membrane, host cell machinery transcribes, translates, and processes the intrabody code to generate an intracellular function-blocking antibody targeted against IL-1α, IL-1b, IL-1Ra, IL-1R1, IL-1R2, IL-1Ra3, IL-1RAP, or IRAK1. In the ca secreted molecules, intracellular antibodies prevent post-translational modification or secretion of the target protein. In the case of membrane-bound molecules, intracellular antibodies prevent intracellular signaling events upon receptor engagement by IL-1 cytokines.

In one preferred embodiment, methods of the invention includes a composition with means to inhibit the transcription, transcript stability, translation, modification, localization, secretion, or receptor binding of IL-1α, IL-1β, or a combination of both cytokines. In one embodiment, the composition comprises a polynucleotide capable of binding to a region of the IL-1α mRNA transcript, defined by SEQ ID NO: 1. In another embodiment, the composition comprises a polynucleotide capable of binding to a region of the IL-1β mRNA transcript, defined by SEQ ID NO: 3.

In another embodiment, the composition is capable of increasing the abundance of the naturally-occuring IL-1 Receptor antagonist (IL-1Ra). The composition comprises a polynucleotide, a polypeptide, an antibody, a compound, or a small molecule that binds to a region of the IL-1Ra gene, mRNA transcript defined by SEQ ID NO: 5, 7, 9, 11, or 13, a polypeptide isoform of IL-1Ra defined by SEQ ID NO: 6, 8, 10, 12, or 14, or a recombinant IL-1Ra protein defined by SEQ ID NO: 16. Alternatively, the composition contains mRNA transcripts or polypeptides encoding a region or the entirety of the IL-1Ra gene.

The composition includes an antagonist or inverse agonist of a receptor for IL-1α or IL-1β, specifically, IL-1R1. In this embodiment an antagonist is defined as a binding partner, or ligand, of an IL-1R that inhibits the function of an agonist, IL-1, or inverse agonist by blocking its binding to the receptor. An inverse agonist is defined as a molecule which binds to the same IL-1R binding-site as an agonist, for instance, IL-1, but exerts the opposite pharmacological effect. The composition contains a polynucleotide, a polypeptide, an antibody, a compound, or a small molecule that binds to a region of the IL-1R1 defined by the polynucleotide and polypeptide sequences SEQ ID NO: 17-21. In an alternative embodiment, the composition includes a molecule with means to inhibit IL-1R transcription, transcript stability, translation, modification, localization, secretion, ligand binding, or association with an accessory protein of an IL-1R (IL-1RAP). IL-1RAP is defined by the polynucleotide sequence of SEQ ID NO: 24 or 26 and the amino acid sequence of SEQ ID NO: 25 or 27.

In another preferred embodiment, the composition includes a human recombinant IL-1R antagonist either in pure form, or as a component of a mixture. The human recombinant IL-1R antagonist is combined with balanced saline, carboxymethylcellulose (CMC), or hyaluronic acid (HA), or other vehicles prior to the composition contacting the cornea. Within these mixtures, the human recombinant IL-1R antagonist comprises at least 0.1%, 2.0%, 2.5%, 5%, or at most 10% of the total volume administered. Preferred aqueous formulations contain 2-2.5% of the purified antagonist. Purified is defined as the antagonist in the absence of unrelated polynucleotides, polypeptides, cellular organelles, or lipids. Purified is defines a degree of sterility that is safe for administration to a human subject, e.g., lacking infectious or toxic agents. All polynucleotides and polypeptides of the invention are purified and/or isolated. As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis. Signs or symptoms of corneal damage or abnormal nerve morphology are detected, analyzed, examined, and evaluated using in vivo confocal microscopy (IVCM) of the central cornea or other imaging or diagnostic devices that allow for detection of corneal nerve damage. Exemplary devices for IVCM include, but are not limited to the Heidelberg Retina Tomograph 3 with the Rostock Cornea Module (HRT3/RCM)(Heidelberg Engineering GMBH) and the Confoscan 4 Confocal Microscope (Nidek, Inc.). In certain embodiments of the above methods, IVCM is used to detect, analyze, examine, and evaluate the form and number of nerve fibers in the various corneal layers, as well as to discriminate between parallel running, bifurcating, branching, and interconnecting nerve fiber bundles. Alternatively or in addition, IVCM is used to detect, analyze, examine, and evaluate changes in the total number of nerves, changes in the length of nerves, nerve density, the presence or absence of abnormal nerve sprouts, the presence or absence of abnormal nerve fiber tortuosity, changes in number or morphology of bead-like nerve formations, and thinning versus thickening of nerve fiber bundles. In one aspect of the methods of the invention, IVCM is used to detect, analyze, examine, and evaluate nerve regeneration. Alternatively, or in addition, IVCM is used to detect, analyze, examine, and evaluate nerve degeneration. For instance, IVCM has been used to show an average of 6-8 corneal nerve bundles per image within the subbasal area of healthy individuals and nerve regeneration in patients who experienced nerve damage as a result of photoreceptive keratectomy.

The invention also provides a method for reducing corneal nerve damage and/or enhancing corneal nerve regeneration in a subject in need thereof, including the steps of: (a) identifying a subject with corneal nerve damage; and (b) locally administering to the cornea of the subject a composition that inhibits an activity of an inflammatory interleukin-17 cytokine, thereby enhancing corneal nerve regeneration, reducing the development of abnormalities in nerve morphology, and reducing corneal nerve damage.

The invention also provides a method for protecting or regenerating corneal nerves in a subject in need thereof, comprising the steps of: (a) identifying a subject with corneal nerve damage or loss; and (b) locally administering to the cornea of the subject a composition that inhibits an activity of an inflammatory interleukin-1 cytokine and a composition that inhibits an activity of an inflammatory interleukin-17 cytokine, thereby enhancing corneal nerve regeneration and reducing the development of abnormalities in nerve morphology or density. This combination therapy leads to a synergistic effect in regenerating corneal nerve tissue.

Publications, U.S. patents and applications, Genbank/NCBI accession numbers, and all other references cited herein, are herby incorporated by reference.

DETAILED DESCRIPTION

Figure 1:
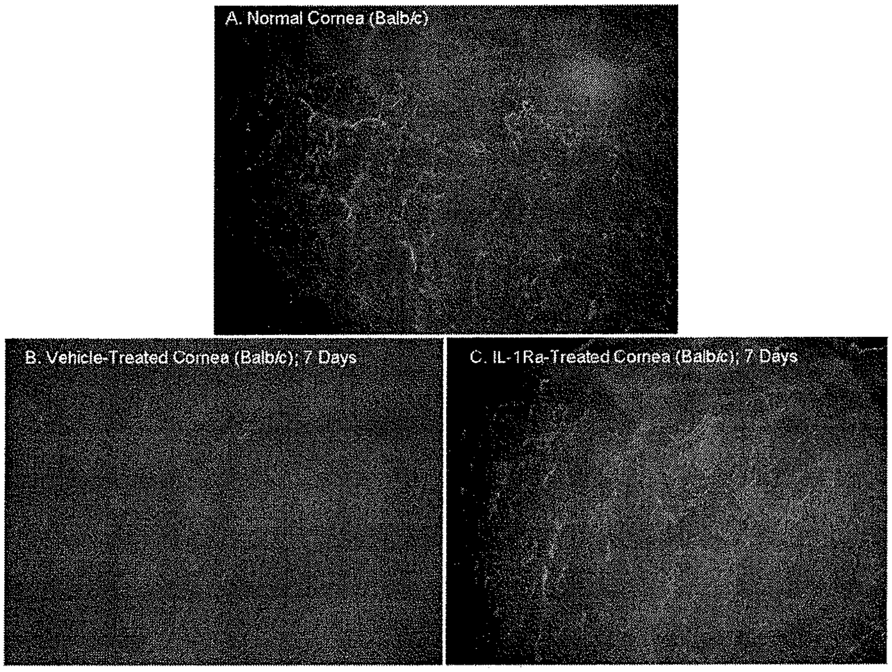
FIG. 1A is a microphotograph that shows the extent of terminal nerve branching system at the level of basal epithelial cells in a normal cornea of a Balb/c mouse.
FIG. 1B is a microphotograph of the terminal nerve processes following 7 days treatment with vehicle after epithelial debridement in a normal cornea of a Balb/c mouse, showing very minimal nerve regeneration activity at the level of the basal epithelial cells.
FIG. 1C is a microphotograph of the regenerated terminal nerve processes following 7 days treatment with 2.5% topical IL-1Ra after epithelial debridement in a normal cornea of a Balb/c mouse, showing a significant number of regenerate nerves at the level of basal epithelial cells, bringing the density of these nerves close to that seen in normal corneas (FIG. 1A).

IL-1, particularly IL-1β, has been reported to promote nerve regeneration. Earlier studies reported that IL-1β was upregulated or stimulated production of the neurotrophin, nerve growth factor (NGF) (Pons et al., 2002, Eur. Respir. J. 20:458-463; Akeda et al., 2007, Spine 32:635-642). For example, IL-10 inhibition using IL-1Ra was found to suppress a neurotrophin response in injured brain tissue. An increase in nerve growth factor (NGF) was found to be directly mediated through IL-1β and blocking IL-1β with IL-1Ra led to suppression of the NGF-mediated reparative response (DeKosky et al., 1996, Ann. Neurol. 39:123-127). The data reported herein indicate that IL-1 blockade stimulates corneal nerve regeneration, an unexpected and surprising finding that contradicts these earlier reports.

IL-1 blockade was used to treat patients characterized by complaints of chronic ocular irritation and discomfort. Using an animal model and clinical studies, compositions and methods of the invention demonstrate that corneal nerves are protected and indeed regenerated by inhibiting the action of IL-1. Specifically, IL-1 blockade through topical administration of IL-1 Receptor antagonist (IL-1 Ra), which acts as an antagonist to IL-1, protects corneal nerves, enhances corneal nerve regeneration, and reduces the abnormalities in subbasal nerve morphology.

Exemplary abnormalities in subbasal nerve morphology include, but are not limited to the presence of abnormal nerve sprouts, abnormal tortuosity, increased bead-like formation, and thinning or thickening of nerve fiber bundles. Thus, IL-1 inhibitors are protective in neuropathic conditions such as herpes simplex or zoster keratitis, diabetes mellitus, dry eye, exposure keratopathy, trigeminal nerve damage associated with orbital or head surgery, head trauma, aneurysms, or intracranial neurologic disease, and corneal nerve damage associated with keratorefractive procedures such as PRK and LASIK.

Corneal nerves are characterized by unique anatomical location, structural features, and functions, compared to other nerves, e.g., the cornea is an avascular location and has unmyelinated nerve endings sensitive to touch, temperature and chemicals. A touch of the cornea or other stimulus causes an involuntary reflex to close the eyelid.

Although some earlier reports describe interleukins and nervous system disorders, the corneal neuroprotective effect of IL-1 blockade is has not been observed prior to the invention described herein. U.S. Pat. No. 6,623,736 refers to interleukins and retinal and optic nerve disorders, but not the cornea or ocular surface. Optic neuritis, macular degeneration, retinitis pigmentosa, and diabetic retinopathy have entirely different pathophysiologic mechanisms, natural histories, epidemiologies, treatments and clinical presentations, as compared to the corneal and ocular surface disorders discussed herein. US20030083301 refers to treatment of spinal cord injuries. The spinal cord, part of the central nervous system, has a physiology, pathobiology, and anatomy distinct from the peripheral nerves of the cornea. There is no mention of any ocular disorders in US20030083301. US20090136453 and US20080242634 refer to methods of administering an IL-1 antagonist for treating pain, but do not describe corneal nerves or degeneration thereof. The invention described herein relates to damage of corneal nerves that can occur without surgical trauma, such as natural disease processes including chronic ocular surface disorders.

Prior to the invention, scientific literature reported that IL-1 induces expression of nerve growth factor (NGF), which is involved in nerve regeneration and survival. For example, Temporin (Temporin et al., 2008 Neurosci Lett., 440(2): 130-3) reports that IL-1 promotes sensory nerve regeneration. Ryoke (Ryoke et al., 2000 Biochem Biophys Res Commun., 267(3): 715-8) reports that IL-1 expression is associated with in vivo nerve regeneration. Guenard (Guenard et al., 1991 J Neurosci Res., 29(3): 396-400) reports that the IL-1 antagonist, IL-1 receptor antagonist (IL-1Ra), impedes peripheral nerve regeneration. Due to the unique nature of corneal nerves, IL-1 inhibition (and the combination of IL-1 and IL-17 inhibition) has a completely different effect in accordance with the invention compared to the earlier reports.

Corneal Structure

The cornea is the transparent front part of the eye that covers the iris, pupil, and anterior chamber. Together with the lens, the cornea refracts light, and as a result helps the eye to focus, accounting for approximately two-thirds of the eye's total optical power. The cornea has unmyelinated nerve endings sensitive to touch, temperature and chemicals; a touch of the cornea causes an involuntary reflex to close the eyelid.

Because transparency is of prime importance the cornea does not have blood vessels; it receives nutrients via diffusion from the tear fluid at the outside and the aqueous humor at the inside and also from neurotrophins supplied by nerve fibers that innervate it. In humans, the cornea has a diameter of about 11.5 mm and a thickness of 0.5-0.6 mm in the center and 0.6-0.8 mm at the periphery. Transparency, avascularity, the presence of highly immature resident immune cells, and immunologic privilege makes the cornea a unique tissue. Immune privilege is meant to describe certain sites in the body that are able to tolerate the introduction of an antigen without eliciting an inflammatory immune response. The cornea has no blood supply, but rather, the cornea it gets oxygen directly through the air and the tears that bathe it.

The human cornea, like that of other primates, has five layers. From the anterior to posterior they are the corneal epithelium, Bowman's layer, the corneal stroma, Descemet's membrane, and the corneal endothelium. The corneal epithelium is a thin epithelial multicellular tissue layer, stratified squamous epithelium, of continuously regenerating cells, kept moist with tears. Irregularity or edema of the corneal epithelium disrupts the smoothness of the air-tear film interface, the most significant component of the total refractive power of the eye, thereby reducing visual acuity. Bowman's layer, also known as the anterior limiting membrane, is a condensed layer of irregularly-arranged collagen, about 8-14 microns thick, that protects the corneal stroma. The corneal stroma, also known as the substantia propria, is a thick and transparent middle layer, consisting of regularly-arranged collagen fibers along with sparsely populated keratocytes. The corneal stroma consists of approximately 200 layers of type I collagen fibrils. Ninety percent of the corneal thickness is composed of the stroma. Descemet's membrane, also known as the posterior limiting membrane, is a thin and acellular layer that serves as the modified basement membrane of the corneal endothelium. The corneal endothelium is a simple squamous or low cuboidal monolayer of mitochondria-rich cells responsible for regulating fluid and solute transport between the aqueous and corneal stromal compartments. The corneal endothelium is bathed by aqueous humour, not by blood or lymph, and has a very different origin, function, and appearance from vascular endothelia. Unlike the corneal epithelium, the cells of the endothelium do not regenerate. Instead, corneal endothelial cells expand or spread to compensate for dead cells which reduces the overall cell density of the endothelium and impacts fluid regulation.

The cornea is one of the most sensitive tissues of the body, it is densely innervated with sensory nerve fibers via the ophthalmic division of the trigeminal nerve by way of 70-80 long and short ciliary nerves. Nerves enter the cornea via three levels, scleral, episcleral and conjunctival. Most of the bundles subdivide and form a network in the stroma, from which fibers supply different regions of the cornea. Three exemplary networks are midstromal, subepithelial/Bowman's layer, and epithelium. Corneal nerves of the subepithelial layer converge and terminate near the apex of the cornea.

Corneal Innervation

The cornea is one of the most densely innervated tissues in the body and is abundantly supplied by different types of nerve fibers. Rabbit studies have revealed that the nerve density of the corneal epithelium is about 300-600 times as much as that of skin and 20-40 times that of the dental pulp. It is estimated that there are approximately 7000 sensory receptors per $mm^2$ in the human corneal epithelium, implying that injuries to individual epithelial cells may be adequate to give a pain perception (Müller et al., Exp Eye Res 2003; 76:521-42).

Most corneal nerve fibers are sensory in origin and are derived from the ophthalmic branch of the trigeminal nerve. Nerve bundles enter the peripheral mid-stromal cornea in a radial fashion parallel to the corneal surface. Soon after entering the cornea, the main stromal bundles branch repeatedly and dichotomously into smaller fascicles that ascended into progressively more superficial layers of the stroma. Eventually, the stromal nerve fibers turn abruptly 90°, penetrate Bowman's layer and proceed towards the corneal surface. After penetrating Bowman's layer, bundles divide and run parallel to the corneal surface between Bowman's layer and the basal epithelium, forming the subbasal nerve plexus. The density and number of nerves in the subbasal epithelial nerve plexus are significantly greater than the density and number of nerves in the remaining corneal layers. Subbasal fibers subsequently form branches that turn upward and enter the corneal epithelium between the basal cells to reach the wing cells, where they terminate (Müller et al., Invest Ophthalmol Vis Sci 1996; 37:476-88).

Corneal nerve fibers mediate not only sensation but also exert critical trophic influences on the corneal epithelium and play a vital role to the preservation of a healthy ocular surface. Corneal sensation is a key mechanism in preventing injury through the blink reflex and reflex tearing. Neuropathy, e.g., degeneration of corneal nerves, leads to changes in sensation. Patients diagnosed with neuropathy of the corneal nerve experience diminished sensation and/or increased pain (hyperalgesia), characterized by chronic discomfort and irritation. Since lacrimation is regulated by the corneal nerves, corneal neuropathy (loss or damaged corneal nerve tissue or decreased length of corneal nerve fibers) leads to tear deficiency. Thus, the methods are useful to reduce the symptoms of tear-deficient dry eye.

Dysfunction of corneal innervation and related neuropathic pathology produces a degenerative condition known clinically as "neurotrophic keratitis", which therefore renders the corneal surface vulnerable to occult injury and delayed healing of established corneal epithelial injuries.

Most clinical cases of neurotrophic keratitis are caused by herpes simplex or zoster keratitis, diabetes mellitus, or by trigeminal nerve damage associated with orbital or head surgery, head trauma, aneurysms, or intracranial neurologic disease. Absent or reduced corneal sensation may be congenital in origin. Keratorefractive procedures such as photorefractive keratectomy (PRK) and laser in situ keratomileusis (LASIK) can sever stromal and subbasal corneal nerves plexus and produce a transient mild to severe neuropathologic condition, or neurotrophic dry eye. This form of "neurotrophic dry eye", characterized by nerve loss and associated dryness, is also seen in non-surgical conditions such as severe forms of dry eye that develop in subjects.

Intact corneal innervation is also mandatory for tearing reflexes. Under normal physiological conditions, sensory nerves in the cornea transmit an afferent stimulation signal to the brain stem and then, after a series of interneurons, the efferent signal is transmitted to the lacrimal gland through the parasympathetic and sympathetic nerves that innervate the gland and drive tear production and secretion (Dartt, D A Ocul Surf 2004; 2:76-91). Damage to this neural circuit interrupts the normal regulation of lacrimal gland secretion and causes dry eye disease. A reduction in neural drive from the cornea favors the occurrence of dry eye-associated ocular surface disease in two ways; first, by decreasing reflex-induced lacrimal secretion and by reducing the blink rate and, consequently, increasing evaporative loss; second, by decreasing the trophic factors to the epithelial layer. Damage to the sensory nerves in the ocular surface, particularly the cornea, as a consequence of refractive surgery and normal aging, prevents the normal reflex arc to the lacrimal gland and can result in decreased tear secretion and dry eye syndromes. Evidence for this mechanism comes from the clinical observation that dry eye syndrome frequently occurs after corneal refractive surgery (e.g., surgery in which the nerve is transected). Clinical studies confirmed that tear production and secretion are reduced after LASIK surgery (Battat et al., Ophthalmology 2001; 108:1230-5). Interestingly, hyposecretion of tears in dry eye may lead to pathologic alterations in corneal nerves and a decline in corneal sensitivity which subsequently perpetuate the dry eye state (Xu et al., Cornea 1996; 15:235-9). Dry eye is further described in PCT/US2008/009776, which is incorporated herein by reference.

Patients with only meibomian gland disease (MGD) or posterior blepharitis are generally not characterized as having clinical neuropathy (clinically significant corneal nerve damage), and hence do not have "neurotrophic" dry eye.

Corneal Pathology

Ocular diseases that affect the corneal epithelium such as dry eye, exposure keratopathy, and other ocular surface diseases cause corneal nerve degeneration. On the other hand, normal neural drive is an essential requirement for corneal epithelium to heal and maintain its homeostasis. Therefore, corneal nerve alterations, either as a primary reason (refractive surgery) or just as the outcome of dryness and other corneal epithelial or ocular surface diseases, have crucial effects on the homeostasis of corneal epithelium, thus neatly contributing to the increase of the vicious cycle of epithelial disease and nerve damage.

Interleukin-1 (IL-1)

The IL-1 family is a group of cytokines that function as major mediators of inflammation and immune response (Dinarello, C. A. 1996. Blood. 15:2095-2147). This family is composed of three forms: two proinflammatory forms, IL-1α and IL-1β, each having a precursor form, and an anti-inflammatory form, IL-1 receptor antagonist (IL-1Ra). The proinflammatory cytokine IL-1 plays an important role in inflammation and immunity by increasing chemokine production, adhesion factors, macrophage infiltration and activity, and lymphocyte proliferation. IL-1 has been implicated in the pathogenesis of human inflammatory diseases, such as rheumatoid arthritis, septic shock, and periodontitis (Jiang, Y. et al. 2000. Arthritis Rheum. 43:1001-1009; Okusawa, S. et al. 1988. J Clin Invest. 81: 1162-1172; McDevitt, M. J. et al. 2000. J. Periodontol. 71:156-163).

The compositions and methods described herein inhibit the activity of human IL-1α and/or IL-1β, as defined by the ability to induce signal transduction or initiate/activate a downstream signaling cascade from an IL-1 receptor. Compositions that contain an inhibitor of human IL-1α or IL-1β function antagonize the activity of an IL-1 receptor. The composition comprises a polynucleotide, a polypeptide, an antibody, a compound, or a small molecule with means to inhibit the transcription, transcript stability, translation, modification, localization, secretion, or function of a polynucleotide or polypeptide encoding human IL-1α or IL-1β. Moreover, the inhibitory polynucleotide or polypeptide composition binds to one or more region(s) of IL-1α or IL-1β comprised by SEQ ID NO: 1 and SEQ ID NO: 2 (IL-1a) or SEQ ID NO: 3 and SEQ ID NO: 4 (IL-1β). The inhibitory polynucleotide or polypeptide composition binds to one or more fragments of IL-1α or IL-1β comprised by SEQ ID NO: 1 and SEQ ID NO: 2 (IL-1α) or SEQ ID NO: 3 and SEQ ID NO: 4 (IL-1β).

A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

Human IL-1α is encoded by the following mRNA sequence (NCBI Accession No. NM_000575 and SEQ ID NO: 1): (For all mRNA transcripts incorporated into the present application, the initiator methionine, encoded by the codon "atg," is bolded and capitalized to delineate the start of the coding region.)

```
accaggcaacaccattgaaggctcatatgtaaaaatccatgccttcctttctcccaatctccattcccaa

acttagccactggcttctggctgaggccttacgcatacctcccggggcttgcacacaccttcttctacag

aagacacaccttgggcatatcctacagaagaccaggcttctctctggtccttggtagagggctactttac

tgtaacagggccagggtggagagttctctcctgaagctccatcccctctataggaaatgtgttgacaata

ttcagaagagtaagaggatcaagacttctttgtgctcaaataccactgttctcttctctaccctgcccta

accaggagcttgtcaccccaaactctgaggtgatttatgccttaatcaagcaaacttccctcttcagaaa
```

-continued agatggctcattttccctcaaaagttgccaggagctgccaagtattctgccaattcaccctggagcacaa tcaacaaattcagccagaacacaactacagctactattagaactattattattaataaattcctctccaa atctagccccttgacttcggatttcacgatttctcccttcctcctagaaacttgataagtttcccgcgct tcccttttttctaagactacatgtttgtcatcttataaagcaaaggggtgaataaatgaaccaaatcaata acttctggaatatctgcaaacaacaataatatcagctatgccatctttcactattttagccagtatcgag ttgaatgaacatagaaaaatacaaaactgaattcttccctgtaaattccccgttttgacgacgcacttgt agccacgtagccacgcctacttaagacaattacaaaaggcgaagaagactgactcaggcttaagctgcca gccagagagggagtcatttcattggcgtttgagtcagcaaagaagtcaagATGgccaaagttccagacat gtttgaagacctgaagaactgttacagtgaaaatgaagaagacagttcctccattgatcatctgtctctg aatcagaaatccttctatcatgtaagctatggcccactccatgaaggctgcatggatcaatctgtgtctc tgagtatctctgaaacctctaaaacatccaagcttaccttcaaggagagcatggtggtagtagcaaccaa cgggaaggttctgaagaagagacggttgagtttaagccaatccatcactgatgatgacctggaggccatc gccaatgactcagaggaagaaatcatcaagcctaggtcagcaccttttagcttcctgagcaatgtgaaat acaactttatgaggatcatcaaatacgaattcatcctgaatgacgccctcaatcaaagtataattcgagc caatgatcagtacctcacggctgctgcattacataatctggatgaagcagtgaaatttgacatgggtgct tataagtcatcaaaggatgatgctaaaattaccgtgattctaagaatctcaaaaactcaattgtatgtga ctgcccaagatgaagaccaaccagtgctgctgaaggagatgcctgagatacccaaaaccatcacaggtag tgagaccaacctcctcttcttctgggaaactcacggcactaagaactatttcacatcagttgcccatcca aacttgtttattgccacaaagcaagactactgggtgtgcttggcagggggggccaccctctatcactgact ttcagatactggaaaaccaggcgtaggtctggagtctcacttgtctcacttgtgcagtgttgacagttca tatgtaccatgtacatgaagaagctaaatcctttactgttagtcatttgctgagcatgtactgagccttg taattctaaatgaatgtttacactctttgtaagagtggaaccaacactaacatataatgttgttatttaa agaacaccctatattttgcatagtaccaatcattttaattattattcttcataacaattttaggaggacc agagctactgactatggctaccaaaaagactctacccatattacagatgggcaaattaaggcataagaaa actaagaaatatgcacaatagcagttgaaacaagaagccacagacctaggatttcatgatttcatttcaa ctgtttgccttctacttttaagttgctgatgaactcttaatcaaatagcataagtttctgggacctcagt tttatcattttcaaaatggagggaataatacctaagccttcctgccgcaacagttttttatgctaatcag ggaggtcattttggtaaaatacttcttgaagccgagcctcaagatgaaggcaaagcacgaaatgttattt tttaattattatttatatatgtatttataaatatatttaagataattataatatactatatttatgggaa ccccttcatcctctgagtgtgaccaggcatcctccacaatagcagacagtgttttctgggataagtaagt ttgatttcattaatacagggcattttggtccaagttgtgcttatcccatagccaggaaactctgcattct agtacttgggagacctgtaatcatataataaatgtacattaattaccttgagccagtaattggtccgatc tttgactcttttgccattaaacttacctgggcattcttgtttcaattccacctgcaatcaagtcctacaa gctaaaattagatgaactcaactttgacaaccatgagaccactgttatcaaaactttcttttctggaatg taatcaatgtttcttctaggttctaaaaattgtgatcagaccataatgttacattattatcaacaatagt gattgatagagtgttatcagtcataactaaataaagcttgcaacaaaattctctgacaaaaaaaaaaaaa aaa.

Human IL-1α is encoded by the following amino acid sequence (NCBI Accession No. NM_000575 and SEQ ID NO: 2):

```
MAKVPDMFEDLKNCYSENEEDSSSIDHLSLNQKSFYHVSYGPLHDSEEEI

IKPRSAPFSFLSNVKYNFMRIIKYEFILNDALNQSIIRANDQYLTAAALH

NLDEAVKFDMGAYKSSKDDAKITVILRISKTQLYVTAQDEDQPVLLK

EMPEIPKTITGSETNLLFFWETHGTKNYFTSVAHPNLFIATKQDYWV

CLAGGPPSITDFQILENQA.
```

Human IL-1β is encoded by the following mRNA sequence (NCBI Accession No. NM_000576 and SEQ ID NO: 3):

-continued

```
DMEQQVVFSMSFVQGEESNDKIPVALGLKEKNLYLSCVLKDDKPTLQLES

VDPKNYPKKKMEKRFVFNKIEINNKLEFESAQFPNWYISTSQAENMPVFL

GGTKGGQDITDFTMQFVSS.
```

Interleukin-1 Receptor (Type 1A Antagonist (IL-1Ra):

IL-1Ra is an endogenous receptor antagonist which is primarily produced by activated monocytes and tissue macrophages, inhibits the activities of the proinflammatory forms of IL-1 by competitively binding to IL-1 receptor. (Gabay, C. et al. 1997. 159: 5905-5913). IL-1Ra is an inducible gene that is typically upregulated in inflammatory conditions (Arend, W. P. 1993. Adv Immunol. 54: 167-223).

accaaacctcttcgaggcacaaggcacaacaggctgctctgggattctcttcagccaatcttcattgctc aagtgtctgaagcagccATGgcagaagtacctgagctcgccagtgaaatgatggcttattacagtggcaa tgaggatgacttgttctttgaagctgatggccctaaacagatgaagtgctccttccaggacctggacctc tgccctctggatggcggcatccagctacgaatctccgaccaccactacagcaagggcttcaggcaggccg cgtcagttgttgtggccatggacaagctgaggaagatgctggttccctgcccacagaccttccaggagaa tgacctgagcaccttctttcccttcatctttgaagaagaacctatcttcttcgacacatgggataacgag gcttatgtgcacgatgcacctgtacgatcactgaactgcacgctccgggactcacagcaaaaaagcttgg tgatgtctggtccatatgaactgaaagctctccacctccagggacaggatatggagcaacaagtggtgtt ctccatgtcctttgtacaaggagaagaaagtaatgacaaaatacctgtggccttgggcctcaaggaaaag aatctgtacctgtcctgcgtgttgaaagatgataagcccactctacagctggagagtgtagatcccaaaa attacccaaagaagaagatggaaaagcgatttgtcttcaacaagatagaaatcaataacaagctggaatt tgagtctgcccagttccccaactggtacatcagcacctctcaagcagaaaacatgcccgtcttcctggga gggaccaaaggcggccaggatataactgacttcaccatgcaatttgtgtcttcctaaagagagctgtacc cagagagtcctgtgctgaatgtggactcaatccctagggctggcagaaagggaacagaaaggtttttgag tacggctatagcctggactttcctgttgtctacaccaatgcccaactgcctgccttagggtagtgctaag aggatctcctgtccatcagccaggacagtcagctctctcctttcagggccaatccccagcccttttgttg agccaggcctctctcacctctcctactcacttaaagcccgcctgacagaaaccacggccacatttggttc taagaaaccctctgtcattcgctcccacattctgatgagcaaccgcttccctatttatttatttatttgt ttgtttgttttattcattggtctaatttattcaaagggggcaagaagtagcagtgtctgtaaaagagcct agtttttaatagctatggaatcaattcaatttggactggtgtgctctctttaaatcaagtcctttaatta agactgaaaatatataagctcagattatttaaatgggaatatttataaatgagcaaatatcatactgttc aatggttctgaaataaacttcactgaag.

Human IL-1β is encoded by the following amino acid sequence (NCBI Accession No. NM_000576 and SEQ ID NO: 4):

```
MAEVPELASEMMAYYSGNEDDLFFEADGPKQMKCSFQDLDLCPLDGGIQL

RISDHHYSKGFRQAASVVVAMDKLRKMLVPCPQTFQENDLSTFFPFIFEE

EPIFFDTWDNEAYVHDAPVRSLNCTLRDSQQKSLVMSGPYELKALHLQGQ
```

In the present invention, compositions comprise one or more regions of IL-1Ra transcripts 1, 2, 3, or 4, intacellular IL-1Ra (icIL-1Ra), or their corresponding polypeptide isoforms. Alternatively, compositions comprise the entirety of IL-1Ra transcripts 1, 2, 3, or 4, intacellular IL-1Ra (icIL-1Ra), or their corresponding polypeptide isoforms. Compositions comprising any form of human IL-1Ra, or fragments thereof, inhibit the function of IL-1R1. These polynucleotides and polypeptides are defined by the following sequences. Human IL-1Ra, transcript 1, is encoded by the following mRNA sequence (NCBI Accession No. NM_173842 and SEQ ID NO: 5):

atttctttataaaccacaactctgggcccgcaatggcagtccactgccttgctgcagtcacagaATGgaa atctgcagaggcctccgcagtcacctaatcactctcctcctcttcctgttccattcagagacgatctgcc gaccctctgggagaaaatccagcaagatgcaagccttcagaatctgggatgttaaccagaagaccttcta tctgaggaacaaccaactagttgctggatacttgcaaggaccaaatgtcaatttagaagaaaagatagat gtggtacccattgagcctcatgctctgttcttgggaatccatggagggaagatgtgcctgtcctgtgtca agtctggtgatgagaccagactccagctggaggcagttaacatcactgacctgagcgagaacagaaagca ggacaagcgcttcgccttcatccgctcagacagcggccccaccaccagttttgagtctgccgcctgcccc ggttggttcctctgcacagcgatggaagctgaccagcccgtcagcctcaccaatatgcctgacgaaggcg tcatggtcaccaaattctacttccaggaggacgagtagtactgcccaggcctgcctgttcccattcttgc atggcaaggactgcagggactgccagtccccctgccccagggctcccggctatgggggcactgaggacca gccattgaggggtggaccctcagaaggcgtcacaagaacctggtcacaggactctgcctcctcttcaact gaccagcctccatgctgcctccagaatggtctttctaatgtgtgaatcagagcacagcagcccctgcaca aagcccttccatgtcgcctctgcattcaggatcaaaccccgaccacctgcccaacctgctctcctcttgc cactgcctcttcctccctcattccaccttcccatgccctggatccatcaggccacttgatgacccccaac caagtggctcccacaccctgttttacaaaaaagaaaagaccagtccatgagggaggtttttaagggtttg tggaaaatgaaaattaggatttcatgatttttttttttcagtccccgtgaaggagagcccttcatttgga gattatgttctttcggggagaggctgaggacttaaaatattcctgcatttgtgaaatgatggtgaaagta agtggtagcttttcccttctttttcttctttttttgtgatgtcccaacttgtaaaaattaaaagttatgg tactatgttagccccataattttttttttttcctttaaaacacttccataatctggactcctctgtccagg cactgctgcccagcctccaagctccatctccactccagatttttacagctgcctgcagtactttacctc ctatcagaagtttctcagctcccaaggctctgagcaaatgtggctcctgggggttctttcttcctctgct gaaggaataaattgctccttgacattgtagagcttctggcacttggagacttgtatgaaagatggctgtg cctctgcctgtctcccccaccgggctgggagctctgcagagcaggaaacatgactcgtatatgtctcagg tccctgcagggccaagcacctagcctcgctcttggcaggtactcagcgaatgaatgctgtatatgttggg tgcaaagttccctacttcctgtgacttcagctctgttttacaataaaatcttgaaaatgcctaaaaaaaa aaaaaaaaaa.

Human IL-1Ra, transcript 1, is encoded by the following amino acid sequence (NCBI Accession No. NM_173842 and SEQ ID NO: 6):

MEICRGLRSHLITLLLFLFHSETICRPSGRKSSKMQAFRIWDVNQKTFYLRNNQLVAGYL

QGPNVNLEEKIDVVPIEPHALFLGIHGGKMCLSCVKSGDETRLQLEAVNITDLSENRKQD

KRFAFIRSDSGPTTSFESAACPGWFLCTAMEADQPVSLTNMPDEGVMVTKFYFQEDE.

Human IL-1Ra, transcript 2, is encoded by the following mRNA sequence (NCBI Accession No. NM_173841 and SEQ ID NO: 7):

gggcagctccaccctgggagggactgtggcccaggtactgcccgggtgctactttatgggcagcagctca gttgagttagagtctggaagacctcagaagacctcctgtcctatgaggccctccccATGgctttagctga cttgtatgaagaaggaggtggaggaggaggagaaggtgaagacaatgctgactcaaaggagacgatctgc cgaccctctgggagaaaatccagcaagatgcaagccttcagaatctgggatgttaaccagaagaccttct atctgaggaacaaccaactagttgctggatacttgcaaggaccaaatgtcaatttagaagaaaagataga -continued tgtggtacccattgagcctcatgctctgttcttgggaatccatggagggaagatgtgcctgtcctgtgtc aagtctggtgatgagaccagactccagctggaggcagttaacatcactgacctgagcgagaacagaaagc aggacaagcgcttcgccttcatccgctcagacagcggccccaccaccagttttgagtctgccgcctgccc cggttggttcctctgcacagcgatggaagctgaccagcccgtcagcctcaccaatatgcctgacgaaggc gtcatggtcaccaaattctacttccaggaggacgagtagtactgcccaggcctgcctgttcccattcttg catggcaaggactgcagggactgccagtccccctgccccagggctcccggctatgggggcactgaggacc agccattgaggggtggaccctcagaaggcgtcacaagaacctggtcacaggactctgcctcctcttcaac tgaccagcctccatgctgcctccagaatggtctttctaatgtgtgaatcagagcacagcagcccctgcac aaagcccttccatgtcgcctctgcattcaggatcaaaccccgaccacctgcccaacctgctctcctcttg ccactgcctcttcctccctcattccaccttcccatgccctggatccatcaggccacttgatgacccccaa ccaagtggctcccacaccctgttttacaaaaaagaaaagaccagtccatgagggaggtttttaagggttt gtggaaaatgaaaattaggatttcatgatttttttttttcagtccccgtgaaggagagcccttcatttgg agattatgttctttcggggagaggctgaggacttaaaatattcctgcatttgtgaaatgatggtgaaagt aagtggtagcttttcccttctttttcttctttttttgtgatgtcccaacttgtaaaaattaaaagttatg gtactatgttagccccataattttttttttcctttaaaacacttccataatctggactcctctgtccag gcactgctgcccagcctccaagctccatctccactccagatttttttacagctgcctgcagtactttacct cctatcagaagtttctcagctcccaaggctctgagcaaatgtggctcctgggggttctttcttcctctgc tgaaggaataaattgctccttgacattgtagagcttctggcacttggagacttgtatgaaagatggctgt gcctctgcctgtctcccccaccgggctgggagctctgcagagcaggaaacatgactcgtatatgtctcag gtccctgcagggccaagcacctagcctcgctcttggcaggtactcagcgaatgaatgctgtatatgttgg gtgcaaagttccctacttcctgtgacttcagctctgttttacaataaaatcttgaaaatgcctaaaaaaa aaaaaaaaaaaaaaaaaaaaaaaaaaaaaaaaaaaaaaaaaaaaa.

Human IL-1Ra, transcript 2, is encoded by the following amino acid sequence (NCBI Accession No. NM_173841 and SEQ ID NO: 8):

MALADLYEEGGGGGGEGEDNADSKETICRPSGRKSSKMQAFRIWDVNQKTFYLRNNQ

LVAGYLQGPNVNLEEKIDVVPIEPHALFLGIHGGKMCLSCVKSGDETRLQLEAVNITDLS

ENRKQDKRFAFIRSDSGPTTSFESAACPGWFLCTAMEADQPVSLTNMPDEGVMVTKFY

FQEDE.

Human IL-1Ra, transcript 3, is encoded by the following mRNA sequence (NCBI Accession No. NM_000577 and SEQ ID NO: 9):

gggcagctccaccctgggagggactgtggcccaggtactgcccgggtgctactttatgggcagcagctca gttgagttagagtctggaagacctcagaagacctcctgtcctatgaggccctccccATGgctttagagac gatctgccgaccctctgggagaaaatccagcaagatgcaagccttcagaatctgggatgttaaccagaag accttctatctgaggaacaaccaactagttgctggatacttgcaaggaccaaatgtcaatttagaagaaa agatagatgtggtacccattgagcctcatgctctgttcttgggaatccatggagggaagatgtgcctgtc ctgtgtcaagtctggtgatgagaccagactccagctggaggcagttaacatcactgacctgagcgagaac agaaagcaggacaagcgcttcgccttcatccgctcagacagcggccccaccaccagttttgagtctgccg cctgccccggttggttcctctgcacagcgatggaagctgaccagcccgtcagcctcaccaatatgcctga -continued cgaaggcgtcatggtcaccaaattctacttccaggaggacgagtagtactgcccaggcctgcctgttccc attcttgcatggcaaggactgcagggactgccagtcccctgccccagggctcccggctatgggggcact gaggaccagccattgaggggtggaccctcagaaggcgtcacaagaacctggtcacaggactctgcctcct cttcaactgaccagcctccatgctgcctccagaatggtctttctaatgtgtgaatcagagcacagcagcc cctgcacaaagcccttccatgtcgcctctgcattcaggatcaaaccccgaccacctgcccaacctgctct cctcttgccactgcctcttcctccctcattccaccttcccatgccctggatccatcaggccacttgatga cccccaaccaagtggctcccacaccctgttttacaaaaaagaaaagaccagtccatgagggaggttttta agggtttgtggaaaatgaaaattaggatttcatgatttttttttttcagtccccgtgaaggagagccctt catttggagattatgttctttcggggagaggctgaggacttaaaatattcctgcatttgtgaaatgatgg tgaaagtaagtggtagcttttcccttctttttcttctttttttgtgatgtcccaacttgtaaaaattaaa agttatggtactatgttagccccataattttttttttcctttaaaacacttccataatctggactcctc tgtccaggcactgctgcccagcctccaagctccatctccactccagatttttacagctgcctgcagtac tttacctcctatcagaagtttctcagctcccaaggctctgagcaaatgtggctcctgggggttctttctt cctctgctgaaggaataaattgctccttgacattgtagagcttctggcacttggagacttgtatgaaaga tggctgtgcctctgcctgtctcccccaccgggctgggagctctgcagagcaggaaacatgactcgtatat gtctcaggtccctgcagggccaagcacctagcctcgctcttggcaggtactcagcgaatgaatgctgtat atgttgggtgcaaagttccctacttcctgtgacttcagctctgttttacaataaaatcttgaaaatgcct aaaaaaaaaaaaaaaaaaaaaaaaaaaaaaaaaaaaaaaaaaaaaaaaaaaa.

Human IL-1Ra, transcript 3, is encoded by the following amino acid sequence (NCBI Accession No. NM_000577 and SEQ ID NO: 10):

MALETICRPSGRKSSKMQAFRIWDVNQKTFYLRNNQLVAGYLQGPNVNLEEKIDVVPIE

PHALFLGIHGGKMCLSCVKSGDETRLQLEAVNITDLSENRKQDKRFAFIRSDSGPTTSFE

SAACPGWFLCTAMEADQPVSLTNMPDEGVMVTKFYFQEDE.

Human IL-1Ra, transcript 4, is encoded by the following mRNA sequence (NCBI Accession No. NM_173843 and SEQ ID NO: 11):

gggcagctccaccctgggagggactgtggcccaggtactgcccgggtgctactttatgggcagcagctca gttgagttagagtctggaagacctcagaagacctcctgtcctatgaggccctccccatggctttagggg attataaaactaatcatcaaagccaagaaggcaagagcaagcatgtaccgctgaaaacacaagataactg cataagtaatgactttcagtgcagattcatagctaacccataaactgctggggcaaaaatcatcttggaa ggctctgaacctcagaaaggattcacaagacgatctgccgaccctctgggagaaaatccagcaagATGca agccttcagaatctgggatgttaaccagaagaccttctatctgaggaacaaccaactagttgctggatac ttgcaaggaccaaatgtcaatttagaagaaaagatagatgtggtacccattgagcctcatgctctgttct tgggaatccatggagggaagatgtgcctgtcctgtgtcaagtctggtgatgagaccagactccagctgga ggcagttaacatcactgacctgagcgagaacagaaagcaggacaagcgcttcgccttcatccgctcagac agcggccccaccaccagttttgagtctgccgcctgccccggttggttcctctgcacagcgatggaagctg accagcccgtcagcctcaccaatatgcctgacgaaggcgtcatggtcaccaaattctacttccaggagga cgagtagtactgcccaggcctgcctgttcccattcttgcatggcaaggactgcagggactgccagtcccc ctgccccagggctcccggctatgggggcactgaggaccagccattgaggggtggaccctcagaaggcgtc -continued acaagaacctggtcacaggactctgcctcctcttcaactgaccagcctccatgctgcctccagaatggtc tttctaatgtgtgaatcagagcacagcagcccctgcacaaagcccttccatgtcgcctctgcattcagga tcaaaccccgaccacctgcccaacctgctctcctcttgccactgcctcttcctccctcattccaccttcc catgccctggatccatcaggccacttgatgacccccaaccaagtggctcccacaccctgttttacaaaaa agaaaagaccagtccatgagggaggtttttaagggtttgtggaaaatgaaaattaggatttcatgatttt tttttttcagtccccgtgaaggagagcccttcatttggagattatgttctttcggggagaggctgaggac ttaaaatattcctgcatttgtgaaatgatggtgaaagtaagtggtagcttttcccttctttttcttcttt ttttgtgatgtcccaacttgtaaaaattaaaagttatggtactatgttagccccataatttttttttcc ttttaaaacacttccataatctggactcctctgtccaggcactgctgcccagcctccaagctccatctcc actccagatttttttacagctgcctgcagtactttacctcctatcagaagtttctcagctcccaaggctct gagcaaatgtggctcctgggggttctttcttcctctgctgaaggaataaattgctccttgacattgtaga gcttctggcacttggagacttgtatgaaagatggctgtgcctctgcctgtctcccccaccgggctgggag ctctgcagagcaggaaacatgactcgtatatgtctcaggtccctgcagggccaagcacctagcctcgctc ttggcaggtactcagcgaatgaatgctgtatatgttgggtgcaaagttccctacttcctgtgacttcagc tctgttttacaataaaatcttgaaaatgcctaaaaaaaaaaaaaaaaaaaaaaaaaaaaaaaaaaaaaaa aaaaaaaaaaaaa.

Human IL-1Ra, transcript 4, is encoded by the following amino acid sequence (NCBI Accession No. NM_173843 and SEQ ID NO: 12):

MQAFRIWDVNQKTFYLRNNQLVAGYLQGPNVNLEEKIDVVPIEPHALF

LGIHGGKMCLSCVKSGDETRLQLEAVNITDLSENRKQDKRFAFIRSDSGP

TTSFESAACPGWFLCTAMEADQPVSLTNMPDEGVMVTKFYFQEDE.

Human intracellular IL-1Ra, icIL-1Ra, is encoded by the following mRNA sequence (NCBI Accession No. M55646 and SEQ ID NO: 13):

agctccaccctgggagggactgtggcccaggtactgcccgggtgctactttatgggcagcagctcagttg agttagagtctggaagacctcagaagacctcctgtcctatgaggccctccccATGgctttagagacgatc tgccgaccctctgggagaaaatccagcaagatgcaagccttcagaatctgggatgttaaccagaagacct tctatctgaggaacaaccaactagttgctggatacttgcaaggaccaaatgtcaatttagaagaaaagat agatgtggtacccattgagcctcatgctctgttcttgggaatccatggagggaagatgtgcctgtcctgt gtcaagtctggtgatgagaccagactccagctggaggcagttaacatcactgacctgagcgagaacagaa agcaggacaagcgcttcgccttcatccgctcagacagtggccccaccaccagttttgagtctgccgcctg ccccggttggttcctctgcacagcgatggaagctgaccagcccgtcagcctcaccaatatgcctgacgaa ggcgtcatggtcaccaaattctacttccaggaggacgagtag.

Human intracellular IL-1Ra, icIL-1Ra, is encoded by the following amino acid sequence (NCBI Accession No. M55646 and SEQ ID NO: 14):

MALETICRPSGRKSSKMQAFRIWDVNQKTFYLRNNQLVAGYLQGPNVNLEEKIDVVPIE

PHALFLGIHGGKMCLSCVKSGDETRLQLEAVNITDLSENRKQDKRFAFIRSDSGPTTSFE

SAACPGWFLCTAMEADQPVSLTNMPDEGVMVTKFYFQEDE.

Human Recombinant IL-1Ra:

A recombinant form of human IL-1Ra (rHuIL-1Ra) was developed and tested in animal models for arthritis. This form of rHuIL-1Ra is also known as Anakinra or Kineret® differs from the native nonglycosylated IL-1Ra by the addition of an N-terminal methionine. It binds to IL-1R type I with the same affinity as IL-1B. Kineret® consists of 153 amino acids and has a molecular weight of 17.3 kilodaltons. It is produced by recombinant DNA technology using an *E. coli* bacterial expression system.

Anakinra has been investigated in several conditions considered mediated at least in part via IL-1. Some evidence suggests involvement of IL-1 in the pathogenesis of rheumatoid arthritis and septic shock (Jiang, Y. et al. 2000. Arthritis Rheum. 43:1001-1009; Fisher, C. J. et al.1994. JAMA.271:1836-1843; Okusawa, S. et al. 1988. J Clin Invest. 81:1162-1172; Bresnihan, B. et al. 1998. Rheum Dis Clin North Am. 24(3):615-628; Dayer, J. M. et al. 2001. Curr Opin Rheumatol. 13:170-176; Edwards, C. K. 2001. J Clin Rheumatol. 7:S17-S24). Anakinra has been approved by the FDA for the reduction in signs and symptoms of moderately to severely active rheumatoid arthritis in patients 18 years of age or older who have failed one or more disease-modifying antirheumatic drugs. Considering its high safety profile, administration of Anakinra has also been used in the treatment of arthritis in patients with Juvenile rheumatoid arthritis (Reiff, A. 2005. Curr Rheumatol Rep. 7:434-40). Other indications include prevention of graft-versus-host disease (GVHD) after bone marrow transplantation (Antin, J. H. et al. 1994. Blood. 84:1342-8), uveitis (Teoh, S. C. et al. 2007. Br J Opthalmol. 91: 263-4) osteoarthritis (Caron, J. P. et al. 1996. Arthritis Rheum. 39:1535-44), asthma, inflammatory bowel disease, acute pancreatitis (Hynninen, M. et al. 1999. J Crit Care. 14:63-8), psoriasis, and type II diabetes mellitus (Larsen, C. M. et al. 2007. N Engl J. Med. 356:1517-26). The systemic safety profile of IL-1Ra is extremely favorable, especially in comparison to other immunosuppressive treatments such as TNF-α blockers, cytotoxic agents, or even steroids.

Topical human recombinant IL-1Ra has been successfully used for prevention of corneal transplant rejection (Yamada, J. et al. 2000. Invest Opthalmol Vis Sci. 41:4203-8) and allergic conjunctivitis (Keane-Myers, A. M. et al. 1999. Invest Opthalmol Vis Sci. 40:3041-6) in experimental animal models. Similarly, using topical IL-1Ra significantly decreases corneal inflammation and leads to enhanced corneal transparency in the rat model of corneal alkali injury (Yamada, J. et al. 2003. Exp Eye Res. 76:161-7).

A recombinant form of human IL-1 Ra (rHuIL-1Ra) was developed and approved for use in humans by subcutaneous injection for the treatment of arthritis. This form of rHuIL-1Ra, also known as Anakinra or Kineret® (Amgen Inc.), differs from the native nonglycosylated IL-1Ra by the addition of an N-terminal methionine. It binds to human IL-1R, type 1, (IL-1R1) with the same affinity as IL-1β. Kineret® consists of 153 amino acids (see SEQ ID NO: 16) and has a molecular weight of 17.3 kilodaltons. It is produced by recombinant DNA technology using an *E. coli* bacterial expression system.

Compositions of the invention comprise one or more regions of SEQ ID NO: 15 or SEQ ID NO: 16. Furthermore, compositions of the invention comprise the entire sequence of either SEQ ID NO: 15 or SEQ ID NO: 16.

Anakinra/Kineret® is encoded by the following mRNA sequence (NCBI Accession No. M55646 and SEQ ID NO: 15):

agctccaccctgggagggactgtggcccaggtactgcccgggtgctactttatgggcagcagctcagttg agttagagtctggaagacctcagaagacctcctgtcctatgaggccctccccATGgctttagagacgatc tgccgaccctctgggagaaaatccagcaagatgcaagccttcagaatctgggatgttaaccagaagacct tctatctgaggaacaaccaactagttgctggatacttgcaaggaccaaatgtcaatttagaagaaaagat agatgtggtacccattgagcctcatgctctgttcttgggaatccatggagggaagatgtgcctgtcctgt gtcaagtctggtgatgagaccagactccagctggaggcagttaacatcactgacctgagcgagaacagaa agcaggacaagcgcttcgccttcatccgctcagacagtggccccaccaccagttttgagtctgccgcctg ccccggttggttcctctgcacagcgatggaagctgaccagcccgtcagcctcaccaatatgcctgacgaa ggcgtcatggtcaccaaattctacttccaggaggacgagtag.

Anakinra/Kineret® is encoded by the following polypeptide sequence (DrugBank Accession No. BTD00060 and SEQ ID NO: 16):

MRPSGRKSSKMQAFRIWDVNQKTFYLRNNQLVAGYLQGPNVNLEEKIDVVPIEPHALF

LGIHGGKMCLSCVKSGDETRLQLEAVNITDLSENRKQDKRFAFIRSDSGPTTSFESAACP

GWFLCTAMEADQPVSLTNMPDEGVMVTKFYFQEDE

IL-1 Receptors:

The composition of the present invention comprises a polynucleotide, a polypeptide, an antibody, a compound, or a small molecule with means to inhibit the transcription, transcript stability, translation, modification, localization, secretion, or function of a polynucleotide or polypeptide encoding the IL-1 receptor, either type 1 or 2. In the present application the IL-1 Receptor, type 1 (IL-1R1), is defined by the polynucleotide sequence of SEQ ID NO: 17 or the polypeptide sequence of SEQ ID NO: 18. In the present application the IL-1 Receptor, type 2 (IL-1R2), transcript variants 1 and 2, are defined by the polynucleotide sequences of SEQ ID NO: 19 and 20, or the polypeptide sequence of SEQ ID NO: 21. IL-1R2 can function as a "decoy" receptor which binds IL-1 cytokines and inhibits IL-1R1. Polynucleotide or polypeptide compositions bind to one or more region(s) of IL-1R1 or IL-1R2, and associated isoforms, comprised by SEQ ID NO: 17-21.

IL-1R1 is encoded by the following mRNA sequence (NCBI Accession No. NM_000877 and SEQ ID NO: 17):

tagacgcaccctctgaagatggtgactccctcctgagaagctggaccccttggtaaaagacaaggccttc tccaagaagaatATGaaagtgttactcagacttatttgtttcatagctctactgatttcttctctggagg ctgataaatgcaaggaacgtgaagaaaaaataattttagtgtcatctgcaaatgaaattgatgttcgtcc ctgtcctcttaacccaaatgaacacaaaggcactataacttggtataaagatgacagcaagacacctgta tctacagaacaagcctccaggattcatcaacacaaagagaaactttggtttgttcctgctaaggtggagg attcaggacattactattgcgtggtaagaaattcatcttactgcctcagaattaaaataagtgcaaaatt tgtggagaatgagcctaacttatgttataatgcacaagccatatttaagcagaaactacccgttgcagga gacggaggacttgtgtgcccttatatggagtttttaaaaatgaaaataatgagttacctaaattacagt ggtataaggattgcaaacctctacttcttgacaatatacactttagtggagtcaaagataggctcatcgt gatgaatgtggctgaaaagcatagagggaactatacttgtcatgcatcctacacatacttgggcaagcaa tatcctattacccgggtaatagaatttattactctagaggaaaacaaacccacaaggcctgtgattgtga gcccagctaatgagacaatggaagtagacttgggatcccagatacaattgatctgtaatgtcaccggcca gttgagtgacattgcttactggaagtggaatgggtcagtaattgatgaagatgacccagtgctaggggaa gactattacagtgtggaaaatcctgcaaacaaaagaaggagtaccctcatcacagtgcttaatatatcgg aaattgaaagtagattttataaacatccatttacctgttttgccaagaatacacatggtatagatgcagc atatatccagttaatatatccagtcactaatttccagaagcacatgattggtatatgtgtcacgttgaca gtcataattgtgtgttctgttttcatctataaaatcttcaagattgacattgtgctttggtacaggatt cctgctatgatttctcccaataaaagcttcagatggaaagacctatgacgcatatatactgtatccaaa gactgttggggaagggtctacctctgactgtgatatttttgtgtttaaagtcttgcctgaggtcttggaa aaacagtgtggatataagctgttcatttatggaagggatgactacgttggggaagacattgttgaggtca ttaatgaaaacgtaaagaaaagcagaagactgattatcattttagtcagagaaacatcaggcttcagctg gctgggtggttcatctgaagagcaaatagccatgtataatgctcttgttcaggatggaattaaagttgtc ctgcttgagctggagaaaatccaagactatgagaaaatgccagaatcgattaaattcattaagcagaaac atggggctatccgctggtcaggggactttacacagggaccacagtctgcaaagacaaggttctggaagaa tgtcaggtaccacatgccagtccagcgacggtcaccttcatctaaacaccagttactgtcaccagccact aaggagaaactgcaaagagaggctcacgtgcctctcgggtagcatggagaagttgccaagagttcttag gtgcctcctgtcttatggcgttgcaggccaggttatgcctcatgctgacttgcagagttcatggaatgta actatatcatcctttatccctgaggtcacctggaatcagattattaagggaataagccatgacgtcaata gcagcccagggcacttcagagtagagggcttgggaagatcttttaaaaaggcagtaggcccggtgtggtg gctcacgcctataatcccagcactttgggaggctgaagtgggtggatcaccagaggtcaggagttcgaga ccagcccagccaacatggcaaaaccccatctctactaaaaatacaaaaatgagctaggcatggtggcaca cgcctgtaatcccagctacacctgaggctgaggcaggagaattgcttgaaccggggagacggaggttgca gtgagccgagtttgggccactgcactctagcctggcaacagagcaagactccgtctcaaaaaaagggcaa taaatgccctctctgaatgtttgaactgccaagaaaaggcatggagacagcgaactagaagaaagggcaa -continued gaaggaaatagccaccgtctacagatggcttagttaagtcatccacagcccaagggcggggctatgcctt gtctggggaccctgtagagtcactgaccctggagcggctctcctgagaggtgctgcaggcaaagtgagac tgacacctcactgaggaagggagacatattcttggagaactttccatctgcttgtattttccatacacat ccccagccagaagttagtgtccgaagaccgaattttattttacagagcttgaaaactcacttcaatgaac aaagggattctccaggattccaaagttttgaagtcatcttagctttccacaggagggagagaacttaaaa aagcaacagtagcagggaattgatccacttcttaatgctttcctccctggcatgaccatcctgtcctttg ttattatcctgcattttacgtctttggaggaacagctccctagtggcttcctccgtctgcaatgtccctt gcacagcccacacatgaaccatccttcccatgatgccgctcttctgtcatcccgctcctgctgaaacacc tcccaggggctccacctgttcaggagctgaagcccatgctttcccaccagcatgtcactcccagaccacc tccctgccctgtcctccagcttcccctcgctgtcctgctgtgtgaattcccaggttggcctggtggccat gtcgcctgcccccagcactcctctgtctctgctcttgcctcgacccttcctcctcctttgcctaggaggc cttctcgcattttctctagctgatcagaattttaccaaaattcagaacatcctccaattccacagtctct gggagactttccctaagaggcgacttcctctccagccttctctctctggtcaggcccactgcagagatgg tggtgagcacatctgggaggctggtctccctccagctggaattgctgctctctgagggagaggctgtggt ggctgtctctgtccctcactgccttccaggagcaatttgcacatgtaacatagatttatgtaatgcttta tgtttaaaaacattccccaattatcttatttaattttgcaattattctaattttatatatagagaaagt gacctatttttaaaaaaatcacactctaagttctattgaacctaggacttgagcctccatttctggctt ctagtctggtgttctgagtacttgatttcaggtcaataacggtccccctcactccacactggcacgttt gtgagaagaaatgacattttgctaggaagtgaccgagtctaggaatgcttttattcaagacaccaaattc caaacttctaaatgttggaattttcaaaaattgtgtttagattttatgaaaaactcttctactttcatct attctttccctagaggcaaacatttcttaaaatgtttcattttcattaaaaatgaaagccaaatttatat gccaccgattgcaggacacaagcacagttttaagagttgtatgaacatggagaggacttttggtttttat atttctcgtatttaatatgggtgaacaccaacttttatttggaataataattttcctcctaaacaaaaac acattgagtttaagtctctgactcttgcctttccacctgctttctcctgggcccgctttgcctgcttgaa ggaacagtgctgttctggagctgctgttccaacagacagggcctagctttcatttgacacacagactaca gccagaagcccatggagcagggatgtcacgtcttgaaaagcctattagatgttttacaaatttaattttg cagattattttagtctgtcatccagaaaatgtgtcagcatgcatagtgctaagaaagcaagccaatttgg aaacttaggttagtgacaaaattggccagagagtgggggtgatgatgaccaagaattacaagtagaatgg cagctggaatttaaggagggacaagaatcaatggataagcgtgggtggaggaagatccaaacagaaaagt gcaaagttattccccatcttccaagggttgaattctggaggaagaagacacattcctagttccccgtgaa cttcctttgacttattgtccccactaaaacaaaacaaaaaacttttaatgccttccacattaattagatt ttcttgcagtttttttatggcatttttttaaagatgccctaagtgttgaagaagagtttgcaaatgcaac aaaatatttaattaccggttgttaaaactggtttagcacaatttatattttccctctcttgcctttctta tttgcaataaaaggtattgagccatttttttaaatgacatttttgataaattatgtttgtactagttgatg aaggagtttttttaacctgtttatataattttgcagcagaagccaaatttttttgtatattaaagcacca aattcatgtacagcatgcatcacggatcaatagactgtacttattttccaataaaattttcaaactttgt actgttaaa.

IL-1R1 is encoded by the following amino acid sequence (NCBI Accession No. NM_000877 and SEQ ID NO: 18):

MKVLLRLICFIALLISSLEADKCKEREEKIILVSSANEIDVRPCPLNPNEHKGTITWYKDDS

KTPVSTEQASRIHQHKEKLWFVPAKVEDSGHYYCVVRNSSYCLRIKISAKFVENEPNLC

YNAQAIFKQKLPVAGDGGLVCPYMEFFKNENNELPKLQWYKDCKPLLLDNIHFSGVKD

RLIVMNVAEKHRGNYTCHASYTYLGKQYPITRVIEFITLEENKPTRPVIVSPANETMEVD

LGSQIQLICNVTGQLSDIAYWKWNGSVIDEDDPVLGEDYYSVENPANKRRSTLITVLNIS

EIESRFYKHPFTCFAKNTHGIDAAYIQLIYPVTNFQKHMIGICVTLTVIIVCSVFIYKIFKIDI

VLWYRDSCYDFLPIKASDGKTYDAYILYPKTVGEGSTSDCDIFVFKVLPEVLEKQCGYK

LFIYGRDDYVGEDIVEVINENVKKSRRLIIILVRETSGFSWLGGSSEEQIAMYNALVQDGI

KVVLLELEKIQDYEKMPESIKFIKQKHGAIRWSGDFTQGPQSAKTRFWKNVRYHMPVQ

RRSPSSKHQLLSPATKEKLQREAHVPLG.

IL-1R2, transcript variant 1, is encoded by the following mRNA sequence (NCBI Accession No. NM_004633 and SEQ ID NO: 19):

cccgtgaggaggaaaaggtgtgtccgctgccacccagtgtgagcgggtgacaccacccggttaggaaatc ccagctcccaagagggtataaatccctgctttactgctgagctcctgctggaggtgaaagtctggcctgg cagccttccccaggtgagcagcaacaaggccacgtgctgctgggtctcagtcctccacttcccgtgtcct ctggaagttgtcaggagcaATGttgcgcttgtacgtgttggtaatgggagtttctgccttcacccttcag cctgcggcacacacaggggctgccagaagctgccggtttcgtgggaggcattacaagcgggagttcaggc tggaaggggagcctgtagccctgaggtgcccccaggtgccctactggttgtgggcctctgtcagcccccg catcaacctgacatggcataaaaatgactctgctaggacggtcccaggagaagaagagacacggatgtgg gcccaggacggtgctctgtggcttctgccagccttgcaggaggactctggcacctacgtctgcactacta gaaatgcttcttactgtgacaaaatgtccattgagctcagagtttttgagaatacagatgctttcctgcc gttcatctcatacccgcaaattttaaccttgtcaacctctggggtattagtatgccctgacctgagtgaa ttcacccgtgacaaaactgacgtgaagattcaatggtacaaggattctcttcttttggataaagacaatg agaaatttctaagtgtgaggggggaccactcacttactcgtacacgatgtggccctggaagatgctggcta ttaccgctgtgtcctgacatttgcccatgaaggccagcaatacaacatcactaggagtattgagctacgc atcaagaaaaaaaaagaagagaccattcctgtgatcatttccccccctcaagaccatatcagcttctctgg ggtcaagactgacaatcccgtgtaaggtgtttctgggaaccggcacacccttaaccaccatgctgtggtg gacggccaatgacacccacatagagagcgcctacccgggaggccgcgtgaccgaggggccacgccaggaa tattcagaaaataatgagaactacattgaagtgccattgatttttgatcctgtcacaagagaggatttgc acatggattttaaatgtgttgtccataataccctgagttttcagacactacgcaccacagtcaaggaagc ctcctccacgttctcctggggcattgtgctggccccactttcactggccttcttggttttgggggaata tggatgcacagacggtgcaaacacagaactggaaaagcagatggtctgactgtgctatggcctcatcatc aagactttcaatcctatcccaagtgaaataaatggaatgaaataattcaaacacaaaaaaaaaaaaaaaa aaaaaaaaaaaaaa.

IL-1R2, transcript variant 2, is encoded by the following mRNA sequence (NCBI Accession No. NM_173343 and SEQ ID NO: 20):

gggatgggagatactgttgtggtcacctctggaaaatacattctgctactcttaaaaactagtgacgctc atacaaatcaacagaaagagcttctgaaggaagactttaaagctgcttctgccacgtgctgctgggtctc agtcctccacttcccgtgtcctctggaagttgtcaggagcaATGttgcgcttgtacgtgttggtaatggg agtttctgccttcacccttcagcctgcggcacacacaggggctgccagaagctgccggtttcgtgggagg cattacaagcgggagttcaggctggaaggggagcctgtagccctgaggtgccccaggtgccctactggt tgtgggcctctgtcagcccccgcatcaacctgacatggcataaaaatgactctgctaggacggtcccagg agaagaagagacacggatgtgggcccaggacggtgctctgtggcttctgccagccttgcaggaggactct ggcacctacgtctgcactactagaaatgcttcttactgtgacaaaatgtccattgagctcagagtttttg agaatacagatgctttcctgccgttcatctcatacccgcaaattttaaccttgtcaacctctggggtatt agtatgccctgacctgagtgaattcacccgtgacaaaactgacgtgaagattcaatggtacaaggattct cttcttttggataaagacaatgagaaatttctaagtgtgaggggaccactcacttactcgtacacgatg tggccctggaagatgctggctattaccgctgtgtcctgacatttgcccatgaaggccagcaatacaacat cactaggagtattgagctacgcatcaagaaaaaaaaagaagagaccattcctgtgatcatttccccctc aagaccatatcagcttctctggggtcaagactgacaatcccgtgtaaggtgtttctgggaaccggcacac ccttaaccaccatgctgtggtggacggccaatgacacccacatagagagcgcctacccgggaggccgcgt gaccgaggggccacgccaggaatattcagaaaataatgagaactacattgaagtgccattgatttttgat cctgtcacaagagaggatttgcacatggattttaaatgtgttgtccataataccctgagttttcagacac tacgcaccacagtcaaggaagcctcctccacgttctcctggggcattgtgctggccccactttcactggc cttcttggttttgggggaatatggatgcacagacggtgcaaacacagaactggaaaagcagatggtctg actgtgctatggcctcatcatcaagactttcaatcctatcccaagtgaaataaatggaatgaaataattc aaacacaaaaaaaaaaaaaaaaaaaaaaaaaaaaa.

IL-1R2, transcript variants 1 and 2, are encoded by the following amino acid sequence (NCBI Accession No. NM_004633, NM_173343, and SEQ ID NO: 21):

MLRLYVLVMGVSAFTLQPAAHTGAARSCRFRGRHYKREFRLEGEPVALRC

PQVPYWLWASVSPRINLTWHKNDSARTVPGEEETRMWAQDGALWLLPALQ

EDSGTYVCTTRNASYCDKMSIELRVFENTDAFLPFISYPQILTLSTSGVL

VCPDLSEFTRDKTDVKIQWYKDSLLLDKDNEKFLSVRGTTHLLVHDVAL

EDAGYYRCVLTFAHEGQQYNITRSIELRIKKKKEETIPVIISPLKTISA

SLGSRLTIPCKVFLGTGTPLTTMLWWTANDTHIESAYPGGRVTEGPRQE

YSENNENYIEVPLIFDPVTREDLHMDFKCVVHNTLSFQTLRTTVKEASS

TFSWGIVLAPLSLAFLVLGGIWMHRRCKHRTGKADGLTVLWPHHQDFQS

YPK.

Interleukin-1 Receptor (Type 2) Antagonist (IL-1Ra3):

The present invention comprises compositions with means to inhibit or enhance the activity of the human IL-1R2. Compositions that comprise the IL-1R2 antagonist, IL-1Ra3, have either agonist or antagonist activity regarding the efficacy of IL-1R1 function. The composition comprises a polynucleotide, a polypeptide, an antibody, a compound, or a small molecule with means to inhibit the transcription, transcript stability, translation, modification, localization, secretion, or function of a polynucleotide or polypeptide encoding IL-1Ra3. The inhibitory polynucleotide or polypeptide composition binds to one or more region(s) of IL-1Ra3 comprised by SEQ ID NO: 22 and SEQ ID NO: 23.

IL-1Ra3 is encoded by a region or the entirety of the following mRNA sequence (NCBI Accession No. AF057168 and SEQ ID NO: 22): (for this sequence, the bolded and capitalized codon does not encode methionine, but rather represents the codon that encodes the first amino acid of the corresponding polypeptide)

cagaagacctcctgtcctatgaggccctccccatggctttaggtaagctccttccactctcatttttttca cctgagaaatgagagaggaaaatgtctacaattggtgtttatcaaatgctttcaggctctggtgagcaag cgtccaggaaaatgtcaagcgcatggagctccaggcctgtctgggggatctgggcacggggaggcatcca tgggagaccatgcaggcactctgaggcaggggctgcaagctagtgcctgctggggcagcaggtgaacaga gaggtgtaactgctgtgacagaagtcatggagtccttggagtgtgagggtcattttccactgttgataga atagggaaattggtgaaatagccctgttaaatgagagaaagaacagtgtgagctcaatgagaaatactaa tagaatgtggcactgagccacaaggtctgagggttgattgataaggaagggtggggactgtggagaatta agggcttggcacaggtcagttccaccagttgtcacaagagaatgcaggctcaggtggccagaacttctcg cttttccagaagagtccgatattctgatttcattatatatagtattctgattaaaccagacaataaagca agcagataaaatatttaaagtataagctgccagtttgcaacctccggttaggatttgtgtggggcaaaga aaaaaactctcaggatcattggtatgtagactctaattttaagtttctaatttaaaattggcccctgagg ctgggcgtggtggctcacacctgtaatcccagcattttgggaggccaaggtgggtggatctcttgaggtc aagagttcaaggcctgcctggccaacatggtgaaaccctgtctctattaaaaatacaaaaattagctggg catggtggtgcatgtctgcaatcttagctacttgggtagctaaggcaggagaattgctggaacccgggag gtagaggttgcagtgaatggagatcacaccactgcactccagtctgggcaatagagagagacgctctctc taaaaaaaaatatgtaaagataaataaaatgaaataaaataggcctctaatgagcaggccattctccttt ctgggtcttactttccttgcactcctttctgggtgttaagaggaggtctagaggaagctggacaactctt agcttgtagtaagcacagtggaagtatcagctcttaatgggtcatggacacgttacgaagctaggcgccg tgctgagcactttacatggtttatcccactgaaccctctcaataaccctatgaggaagggctattattgc tcacattttcagaagaggaaatggatatagagagattagataatttgcccatggccagacagctagtata agaggaggaggtggattgactgcagacattctgtcttcaaaccactacactatgctatggaggcacagag acttaatgaaatcatggagaggggaattgctttgtcaaccacaagcagttattccgggggcagcagatcc tcccctgtcccccagtggtacaatggtccctggtgggttgtgctacaatgttagcccatggtcttatgtg tttttcaaatgtgtaaagtaggatgctggaaccactcttagaaccagataccaatacattgtgaagaaat aaatctctgtgcttaaaactggttcatcccaaaatattttgaactgacacacaataggtgctaaataaat gtgtgttaacttgaattggattgaattcgggaaaaaagtgcaataagcttagtgaagacaccatgttccc tgggtagaggaaccacattctccatctaaggccaggagtatgggaggtatcaatgtttgcccagcacaga acagggtgccaagaagagaaaagttgacggggtgcatactctgactggaaactggaagggtgagaacaga gggtaaaggatagagatggaaccatgtgcatacactttgtgttaccttggacaagtcattcatttctctg gacctctgctttctctctacacaatggggtcccaccacttcccttacagctgacttgtatgaagaaggag gtggaggaggaggagaaggtgaagacaatgCTGactcaaagggtaaattatttttaggatccaagtttga aaacaattttaggctactagatatgaacaacatcttgattatgtagttgaaggaaattaaagatgaatgg tttaattaaaaattaatcagaatgaaaacgattgattactaatatatctgcaatggtttattttcctgag tggcagactcactaaggtttttgaatactcctgtgtgattgctctatgtatgtatgtatgtatgtatgta tgcatgtatctatctatctgttgtctaatagaatggatcacatctctgctaataaaaacactacactggc agggtacaattataatcattaactgtgcctggaatttgcagcagcagccaccagaggtaccagtgccctt taagggttcataatttagaataatccaattatctgagtttttcagggactgaggggtttggcaaggtgta gaactttcagtaataaagtcaagaaagtcctggacaaaccaaggtagttggtcactctagtccataacca ggtaaagagctttccctgtaacctgtgtaaggttttagaatcatttctttccttattaccaaaaatcctc cccaaattttcaagaaattatgaactaaatagttactctatgagataggagttcagcccaaaagaaacac cataagaacaaatataattcttgcttatgttaaccatgcaatgaagcagagagaaaaagtcagtggcctc -continued

```
tttaggaggactgtagtgtgggaagaaataactaaactgggtttcaatcctggcctggccaggatctgga
gcaagtgagttaatctttctaagccttgagtagtttataaaagaatggccactccatagacagagtagcc
tgaaccttgagttcttctataaagtcactatgaatttatactcattttgaaagtgggtgtcaatatgtct
gtccactttgcacagctgttatgtggacaaaaggagatctgtgtgaaagtgtaacacagagcctaaacta
taacaggtaagcaacacagttgtccct.
```

One or more isoforms of IL-1Ra3 comprise the following amino acid sequence (NCBI Accession No. AF_057168 and SEQ ID NO: 23):

```
DLYEEGGGGGGEGEDNADSK.
```

Interleukin-1 Receptor Accessory Protein (IL-1RAP):

Compositions that inhibit the activity of human IL-1RAP inhibit IL-1RAP binding to an IL-1 cytokine or an IL-1 receptor, and subsequent transduction of downstream intracellular signals. Compositions that comprise an inhibitor of IL-1RAP function antagonize the activity of an IL-1 receptor. The composition comprises a polynucleotide, a polypeptide, an antibody, a compound, or a small molecule with means to inhibit the transcription, transcript stability, translation, modification, localization, secretion, or function of a polynucleotide or polypeptide encoding IL-1RAP. The inhibitory polynucleotide or polypeptide composition binds to one or more region(s) of IL-1RAP, and associated isoforms, comprised by SEQ ID NO: 24-27. IL-1RAP, transcript variant 1, is encoded by the following mRNA sequence (NCBI Accession No. NM_002182 and SEQ ID NO: 24):

```
tgccgggatccaggtctccggggtccgctttggccagaggcgcggaaggaagcagtgcccggcgacactg
cacccatcccggctgcttttgctgcgccctctcagcttcccaagaaaggcatcgtcatgtgatcatcacc
taagaactagaacatcagcaggccctagaagcctcactcttgcccctccctttaatatctcaaaggATGa
cacttctgtggtgtgtagtgagtctctacttttatggaatcctgcaaagtgatgcctcagaacgctgcga
tgactggggactagacaccatgaggcaaatccaagtgtttgaagatgagccagctcgcatcaagtgccca
ctctttgaacacttcttgaaattcaactacagcacagcccattcagctggccttactctgatctggtatt
ggactaggcaggaccgggaccttgaggagccaattaacttccgcctccccgagaaccgcattagtaagga
gaaagatgtgctgtggttccggcccactctcctcaatgacactggcaactatacctgcatgttaaggaac
actacatattgcagcaaagttgcatttcccttggaagttgttcaaaaagacagctgtttcaattcccccca
tgaaactcccagtgcataaactgtatatagaatatggcattcagaggatcacttgtccaaatgtagatgg
atattttccttccagtgtcaaaccgactatcacttggtatatgggctgttataaaatacagaattttaat
aatgtaatacccgaaggtatgaacttgagtttcctcattgccttaatttcaaataatggaaattacacat
gtgttgttacatatccagaaaatggacgtacgtttcatctcaccaggactctgactgtaaaggtagtagg
ctctccaaaaaatgcagtgccccctgtgatccattcacctaatgatcatgtggtctatgagaaagaacca
ggagaggagctactcattccctgtacggtctattttagttttctgatggattctcgcaatgaggtttggt
ggaccattgatggaaaaaaacctgatgacatcactattgatgtcaccattaacgaaagtataagtcatag
tagaacagaagatgaaacaagaactcagattttgagcatcaagaaagttacctctgaggatctcaagcgc
agctatgtctgtcatgctagaagtgccaaaggcgaagttccaaagcagccaaggtgaagcagaaagtgcc
agctccaagatacacagtggaactggcttgtggttttggagccacagtcctgctagtggtgattctcatt
gttgtttaccatgtttactggctagagatggtcctattttaccgggctcattttggaacagatgaaacca
ttttagatggaaaagagtatgatatttatgtatcctatgcaaggaatgcggaagaagaagaatttgtatt
actgaccctccgtggagttttggagaatgaatttggatacaagctgtgcatctttgaccgagacagtctg
cctgggggaattgtcacagatgagactttgagcttcattcagaaaagcagacgcctcctggttgttctaa
gccccaactacgtgctccagggaacccaagccctcctggagctcaaggctggcctagaaaatatggcctc
tcggggcaacatcaacgtcattttagtacagtacaaagctgtgaaggaaacgaaggtgaaagagctgaag
agggctaagacggtgctcacggtcattaaatggaaaggggaaaaatccaagtatccacagggcaggttct
```

-continued ggaagcagctgcaggtggccatgccagtgaagaaaagtcccaggcggtctagcagtgatgagcagggcct ctcgtattcatctttgaaaaatgtatgaaaggaataatgaaaagggtaaaaagaacaaggggtgctccag gaagaaagagtccccccagtcttcattcgcagtttatggtttcataggcaaaaataatggtctaagcctc ccaatagggataaatttagggtgactgtgtggctgactattctgcttcctcaggcaacactaaagtttag aaagatatcatcaacgttctgtcaccagtctctgatgccactatgttctttgcaggcaaagacttgttca atgcgaatttccccttctacattgtctatccctgtttttatatgtctccattctttttaaaatcttaaca tatggagcagcctttcctatgaatttaaatatgcctttaaaataagtcactgttgacagggtcatgagtt tccgagtatagttttctttttatcttatttttactcgtccgttgaaaagataatcaaggcctacatttta gctgaggataatgaactttttttcctcattcggctgtataatacataaccacagcaagactgacatccact taggatgatacaaagcagtgtaactgaaaatgtttcttttaattgatttaaaggacttgtcttctatacc acccttgtcctcatctcaggtaatttatgaaatctatgtaaacttgaaaaatatttcttaatttttgttt ttgctccagtcaattcctgattatccacaggtcaacccacatttttttcattccttctccctatctgctta tatcgcattgctcatttagagtttgcaggaggctccatactaggttcagtctgaaagaaatctcctaatg gtgctatagagagggaggtaacagaaagactcttttagggcatttttctgactcatgaaaagagcacaga aaaggatgtttggcaatttgtcttttaagtcttaaccttgctaatgtgaatactgggaaagtgatttttt ctcactcgtttttgttgctccattgtaaagggcggaggtcagtcttagtggccttgagagttgcttttgg cattaatattctaagagaattaactgtatttcctgtcacctattcactagtgcaggaaatatacttgctc caaataagtcagtatgagaagtcactgtcaatgaaagttgttttgtttgttttcagtaatattttgctgt ttttaagacttggaaaactaagtgcagagtttacagagtggtaaatatctatgttacatgtagattatac atatatatacacacgtgtatatgagatatatatcttatatctccacaaacacaaattatatatatacata tccacacacatacattacatatatctgtgtatataaatccacatgcacatgaaatatatatatatatata atttgtgtgtgtgtatgtgtatgtatatgactttaaatagctatgggtacaatattaaaaaccactggaa ctcttgtccagtttttaaattatgtttttactggaatgtttttgtgtcagtgttttctgtacatattatt tgttaattcacagctcacagagtgatagttgtcatagttcttgccttccctaagtttatataaataactt aagtattgctacagtttatctaggttgcagtggcatctgctgtgcacagagcttccatggtcactgctaa gcagtagccagccatcgggcattaattgatttcctactatattcccagcagacacatttagaaactaagc tatgttaacctcagtgctcaactatttgaactgttgagtgataaaggaaacaaatataactgtaaatgaa tcttggtatcctgtgaaacagaataattcgtaatttaagaaagcccttatcccggtaacatgaatgttga tgaacaaatgtaaaattatatcctatatttaagtacccataataaatcatttccctctataagtgttatt gattattttaaattgaaaaaagtttcacttggatgaaaaaagtagaaaagtaggtcattcttggatctac tttttttagccttattaatatttttccctattagaaaccacaattactccctctattaacccttcactt actagaccagaaaagaacttattccagataagctttgaatatcaattcttacataaactttaggcaaaca gggaatagtctagtcaccaaaggaccattctcttgccaatgctgcattccttttgcacttttggattcca tatttatcccaaatgctgttgggcacccctagaaataccttgatgtttttctatttatatgcctgcctt tggtacttaattttacaaatgctgtaatataaagcatatcaagtttatgtgatacgtatcattgcaagag aatttgtttcaagatttttttttaatgttccagaagatggccaatagagaacattcaagggaaatgggga aacataatttagagaacaagaacaaaccatgtctcaaatttttttaaaaaaaattaatggttttaaatat atgctatagggacgttccatgcccaggttaacaaagaactgtgatatatagagtgtctaattacaaaatc atatacgatttatttaattctcttctgtattgtaacttagatgattcccaaggactctaataaaaaatca -continued cttcattgtatttggaaacaaaaacatcattcattaattacttattttctttccataggttttaatattt tgagagtgtctttttatttcattcatgaacttttgtatttttcatttttcatttgatttgtaaatttac ttatgttaaaaataaaccatttattttcagctttg.

IL-1RAP, transcript variant 1, is encoded by the following amino acid sequence (NCBI Accession No. NM_002182 and SEQ ID NO: 25):

MTLLWCVVSLYFYGILQSDASERCDDWGLDTMRQIQVFEDEPARIKCPLF

EHFLKFNYSTAHSAGLTLIWYWTRQDRDLEEPINFRLPENRISKEKDVL

WFRPTLLNDTGNYTCMLRNTTYCSKVAFPLEVVQKDSCFNSPMKLPVHKL

YIEYGIQRITCPNVDGYFPSSVKPTITWYMGCYKIQNFNNVIPEGMNLSF

LIALISNNGNYTCVVTYPENGRTFHLTRTLTVKVVGSPKNAVPPVIHSP

NDHVVYEKEPGEELLIPCTVYFSFLMDSRNEVWWTIDGKKPDDITIDVT

-continued

INESISHSRTEDETRTQILSIKKVTSEDLKRSYVCHARSAKGEVAKAAK

VKQKVPAPRYTVELACGFGATVLLVVILIVVYHVYWLEMVLFYRAHFGT

DETILDGKEYDIYVSYARNAEEEEFVLLTLRGVLENEFGYKLCIFDRDS

LPGGIVTDETLSFIQKSRRLLVVLSPNYVLQGTQALLELKAGLENMASR

GNINVILVQYKAVKETKVKELKRAKTVLTVIKWKGEKSKYPQGRFWKQLQ

VAMPVKKSPRRSSSDEQGLSYSSLKNV.

IL-1RAP, transcript variant 2, is encoded by the following mRNA sequence (NCBI Accession No. NM_134470 and SEQ ID NO: 26):

tgccgggatccaggtctccggggtccgctttggccagaggcgcggaaggaagcagtgcccggcgacactg cacccatcccggctgcttttgctgcgccctctcagcttcccaagaaaggcatcgtcatgtgatcatcacc taagaactagaacatcagcaggccctagaagcctcactcttgcccctccctttaatatctcaaaggATGa cacttctgtggtgtgtagtgagtctctacttttatggaatcctgcaaagtgatgcctcagaacgctgcga tgactggggactagacaccatgaggcaaatccaagtgtttgaagatgagccagctcgcatcaagtgccca ctctttgaacacttcttgaaattcaactacagcacagcccattcagctggccttactctgatctggtatt ggactaggcaggaccgggaccttgaggagccaattaacttccgcctccccgagaaccgcattagtaagga gaaagatgtgctgtggttccggcccactctcctcaatgacactggcaactatacctgcatgttaaggaac actacatattgcagcaaagttgcatttcccttggaagttgttcaaaaagacagctgtttcaattcccccca tgaaactcccagtgcataaactgtatatagaatatggcattcagaggatcacttgtccaaatgtagatgg atattttccttccagtgtcaaaccgactatcacttggtatatgggctgttataaaatacagaattttaat aatgtaatacccgaaggtatgaacttgagtttcctcattgccttaatttcaaataatggaaattacacat gtgttgttacatatccagaaaatggacgtacgtttcatctcaccaggactctgactgtaaaggtagtagg ctctccaaaaaatgcagtgccccctgtgatccattcacctaatgatcatgtggtctatgagaaagaacca ggagaggagctactcattccctgtacggtctattttagttttctgatggattctcgcaatgaggtttggt ggaccattgatggaaaaaaacctgatgacatcactattgatgtcaccattaacgaaagtataagtcatag tagaacagaagatgaaacaagaactcagattttgagcatcaagaaagttacctctgaggatctcaagcgc agctatgtctgtcatgctagaagtgccaaaggcgaagttgccaaagcagccaaggtgaagcagaaaggta atagatgcggtcagtgatgaatctctcagctccaaattaacattgtggtgaataaggacaaaaggagaga ttgagaacaagagagctccagcacctagcccgacggcatctaacccatagtaatgaatcaaacttaaatg aaaaatatgaaagttttcatctatgtaagatactcaaaatattgtttctgatattgttagtaccgtaatg cccaaatgtagctaaaaaaatcgacgtgagtacagtgagacacaattttgtgtctgtacaattatgaaaa attaaaaacaaagaaaatattcaaagctaccaaagatagaaaaaactggtagagccacatattgttggtg aattattaagacccttttaaaaatcattcatggtagagtttaagagtcataaaaaagattgcatcatctg acctaagactttcggaatttttcctgaacaaataacagaaagggaattatataccttttaatattattag aagcattatctgtagttgtaaaacattattaatagcagccatccaattgtatgcaactaattaaggtatt gaatgtttattttccaaaaaatgcataattataatattattttaaacactatgtatcaatatttaagcagg -continued tttataatataccagcagccacaattgctaaaatgaaaatcatttaaattatgattttaaatggtataaa catgatttctatgttgatagtactatattattctacaataaatggaaattataaagccttcttgtcagaa gtgctgctcctaaaaaaaaaaaaaaaaaaaaaa.

IL-1RAP, transcript variant 2, is encoded by the following amino acid sequence (NCBI Accession No. NM_134470 and SEQ ID NO: 27):

MTLLWCVVSLYFYGILQSDASERCDDWGLDTMRQIQVFEDEPARIKCPLF

EHFLKFNYSTAHSAGLTLIWYWTRQDRDLEEPINFRLPENRISKEKDVLW

FRPTLLNDTGNYTCMLRNTTYCSKVAFPLEVVQKDSCFNSPMKLPVHKLY

IEYGIQRITCPNVDGYFPSSVKPTITWYMGCYKIQNFNNVIPEGMNLSFL

IALISNNGNYTCVVTYPENGRTFHLTRTLTVKVVGSPKNAVPPVIHSPND

HVVYEKEPGEELLIPCTVYFSFLMDSRNEVWWTIDGKKPDDITIDVTINE

SISHSRTEDETRTQILSIKKVTSEDLKRSYVCHARSAKGEVAKAAKVKQK

GNRCGQ.

Interleukin-1 Receptor Associated Kinase 1 (IRAK1):

The invention also comprises compositions and methods to inhibit the activity of human IRAK1, defined as the ability of this protein to bind an IL-1 receptor following ligation of this receptor with IL-1, as well as to transduce downstream signals leading to an inflammatory response. Compositions that comprise an inhibitor of IRAK1 antagonize downstream signaling from an IL-1 receptor. The composition comprises a polynucleotide, a polypeptide, an antibody, a compound, or a small molecule with means to inhibit the transcription, transcript stability, translation, modification, localization, secretion, or function of a polynucleotide or polypeptide encoding IRAK1. The inhibitory polynucleotide or polypeptide composition binds to one or more region(s) of IRAK1, and associated isoforms, comprised by SEQ ID NO: 28-33. IRAK1, transcript variant 1, is encoded by the following mRNA sequence (NCBI Accession No. NM_001569 and SEQ ID NO: 28):

cgcggacccggccggcccaggcccgcgcccgccgcggccctgagaggccccggcaggtcccggcccggcg gcggcagccATGgccgggggccgggcccgggggagcccgcagcccccggcgcccagcacttcttgtacg aggtgccgccctgggtcatgtgccgcttctacaaagtgatggacgccctggagcccgccgactggtgcca gttcgccgccctgatcgtgcgcgaccagaccgagctgcggctgtgcgagcgctccgggcagcgcacggcc agcgtcctgtggccctggatcaaccgcaacgcccgtgtggccgacctcgtgcacatcctcacgcacctgc agctgctccgtgcgcgggacatcatcacagcctggcaccctcccgccccgcttccgtccccaggcaccac tgccccgaggcccagcagcatccctgcacccgccgaggccgaggcctggagcccccggaagttgccatcc tcagcctccaccttcctctccccagcttttccaggctcccagacccattcagggcctgagctcggcctgg tcccaagccctgcttccctgtggcctccaccgccatctccagccccttcttctaccaagccaggcccaga gagctcagtgtccctcctgcagggagcccgcccctttccgttttgctggcccctctgtgagatttcccgg ggcacccacaacttctcggaggagctcaagatcggggagggtggctttgggtgcgtgtaccgggcggtga tgaggaacacggtgtatgctgtgaagaggctgaaggagaacgctgacctggagtggactgcagtgaagca gagcttcctgaccgaggtggagcagctgtccaggtttcgtcacccaaacattgtggactttgctggctac tgtgctcagaacggcttctactgcctggtgtacggcttcctgcccaacggctccctggaggaccgtctcc actgccagacccaggcctgcccacctctctcctggcctcagcgactggacatccttctgggtacagcccg ggcaattcagtttctacatcaggacagccccagcctcatccatggagacatcaagagttccaacgtcctt ctggatgagaggctgacacccaagctgggagactttggcctggcccggttcagccgctttgccgggtcca gccccagccagagcagcatggtggcccggacacagacagtgcggggcaccctggcctacctgcccgagga gtacatcaagacgggaaggctggctgtggacacggacaccttcagctttggggtggtagtgctagagacc ttggctggtcagagggctgtgaagacgcacggtgccaggaccaagtatctgaaagacctggtggaagagg aggctgaggaggctggagtggctttgagaagcacccagagcacactgcaagcaggtctggctgcagatgc ctgggctgctcccatcgccatgcagatctacaagaagcacctggaccccaggcccgggccctgcccacct gagctgggcctgggcctgggccagctggcctgctgctgcctgcaccgccgggccaaaaggaggcctccta tgacccaggtgtacgagaggctagagaagctgcaggcagtggtggcgggggtgcccgggcattcggaggc -continued

```
cgccagctgcatcccccttccccgcaggagaactcctacgtgtccagcactggcagagcccacagtggg
gctgctccatggcagcccctggcagcgccatcaggagccagtgcccaggcagcagagcagctgcagagag
gccccaaccagcccgtggagagtgacgagagcctaggcggcctctctgctgccctgcgctcctggcactt
gactccaagctgccctctggacccagcacccctcagggaggccggctgtcctcaggggacacggcagga
gaatcgagctgggggagtggcccaggatcccggcccacagccgtggaaggactggcccttggcagctctg
catcatcgtcgtcagagccaccgcagattatcatcaaccctgcccgacagaagatggtccagaagctggc
cctgtacgaggatggggccctggacagcctgcagctgctgtcgtccagctccctcccaggcttgggcctg
gaacaggacaggcaggggcccgaagaaagtgatgaatttcagagctgatgtgttcacctgggcagatccc
ccaaatccggaagtcaaagttctcatggtcagaagttctcatggtgcacgagtcctcagcactctgccgg
cagtgggggtgggggcccatgcccgcgggggagagaaggaggtggccctgctgttctaggctctgtgggc
ataggcaggcagagtggaaccctgcctccatgccagcatctgggggcaaggaaggctggcatcatccagt
gaggaggctggcgcatgttgggaggctgctggctgcacagacccgtgaggggaggagaggggctgctgtg
caggggtgtggagtagggagctggctcccctgagagccatgcagggcgtctgcagcccaggcctctggca
gcagctctttgcccatctctttggacagtggccaccctgcacaatggggccgacgaggcctagggccctc
ctacctgcttacaatttggaaaagtgtggccgggtgcggtggctcacgcctgtaatcccagcactttggg
aggccaaggcaggaggatcgctggagcccagtaggtcaagaccagccagggcaacatgatgagaccctgt
ctctgccaaaaaatttttaaactattagcctggcgtggtagcgcacgcctgtggtcccagctgctgggg
aggctgaagtaggaggatcatttatgcttgggaggtcgaggctgcagtgagtcatgattgtatgactgca
ctccagcctgggtgacagagcaagaccctgtttcaaaaagaaaaaccctgggaaaagtgaagtatggctg
taagtctcatggttcagtcctagcaagaagcgagaattctgagatcctccagaaagtcgagcagcaccca
cctccaacctcgggccagtgtcttcaggctttactggggacctgcgagctggcctaatgtggtggcctgc
aagccaggccatccctgggcgccacagacgagctccgagccaggtcaggcttcggaggccacaagctcag
cctcaggcccaggcactgattgtggcagaggggccactacccaaggtctagctaggcccaagacctagtt
acccagacagtgagaagcccctggaaggcagaaaagttgggagcatggcagacagggaagggaaacattt
tcagggaaaagacatgtatcacatgtcttcagaagcaagtcaggtttcatgtaaccgagtgtcctcttgc
gtgtccaaaagtagcccagggctgtagcacaggcttcacagtgattttgtgttcagccgtgagtcacact
acatgcccccgtgaagctgggcattggtgacgtccaggttgtccttgagtaataaaaacgtatgttgcaa
taaaaaaaaaaaaaaaaa.
```

IRAK1, transcript variant 1, is encoded by the following amino acid sequence (NCBI Accession No. NM_001569 and SEQ ID NO: 29):

```
MAGGPGPGEPAAPGAQHFLYEVPPWVMCRFYKVMDALEPADWCQFAALIV
RDQTELRLCERSGQRTASVLWPWINRNARVADLVHILTHLQLLRARDIIT
AWHPPAPLPSPGTTAPRPSSIPAPAEAEAWSPRKLPSSASTFLSPAFPGS
QTHSGPELGLVPSPASLWPPPPSPAPSSTKPGPESSVSLLQGARPFPFCW
PLCEISRGTHNFSEELKIGEGGFGCVYRAVMRNTVYAVKRLKENADLEWT
AVKQSFLTEVEQLSRFRHPNIVDFAGYCAQNGFYCLVYGFLPNGSLEDRL
HCQTQACPPLSWPQRLDILLGTARAIQFLHQDSPSLIHGDIKSSNVLLD
```

-continued

```
ERLTPKLGDFGLARFSRFAGSSPSQSSMVARTQTVRGTLAYLPEEYIKTG
RLAVDTDTFSFGVVVLETLAGQRAVKTHGARTKYLKDLVEEEAEEAGVA
LRSTQSTLQAGLAADAWAAPIAMQIYKKHLDPRPGPCPPELGLGLGQLA
CCCLHRRAKRRPPMTQVYERLEKLQAVVAGVPGHSEAASCIPPSPQENS
YVSSTGRAHSGAAPWQPLAAPSGASAQAAEQLQRGPNQPVESDESLGGL
SAALRSWHLTPSCPLDPAPLREAGCPQGDTAGESSWGSGPGSRPTAVEG
LALGSSASSSSEPPQIIINPARQKMVQKLALYEDGALDSLQLLSSSSLP
GLGLEQDRQGPEESDEFQS.
```

IRAK1, transcript variant 2, is encoded by the following mRNA sequence (NCBI Accession No. NM_001025242 and SEQ ID NO: 30):

cgcggacccggccggcccaggcccgcgcccgccgcggccctgagaggccccggcaggtcccggcccggcg
gcggcagccATGgccggggggccgggcccgggggagcccgcagcccccggcgcccagcacttcttgtacg
aggtgccgccctgggtcatgtgccgcttctacaaagtgatggacgccctggagcccgccgactggtgcca
gttcgccgccctgatcgtgcgcgaccagaccgagctgcggctgtgcgagcgctccgggcagcgcacggcc
agcgtcctgtggccctggatcaaccgcaacgcccgtgtggccgacctcgtgcacatcctcacgcacctgc
agctgctccgtgcgcgggacatcatcacagcctggcaccctcccgccccgcttccgtccccaggcaccac
tgccccgaggcccagcagcatccctgcacccgccgaggccgaggcctggagcccccggaagttgccatcc
tcagcctccaccttcctctccccagcttttccaggctcccagacccattcagggcctgagctcggcctgg
tcccaagccctgcttccctgtggcctccaccgccatctccagccccttcttctaccaagccaggcccaga
gagctcagtgtccctcctgcagggagcccgcccctttccgttttgctggcccctctgtgagatttcccgg
ggcacccacaacttctcggaggagctcaagatcggggagggtggctttgggtgcgtgtaccgggcggtga
tgaggaacacggtgtatgctgtgaagaggctgaaggagaacgctgacctggagtggactgcagtgaagca
gagcttcctgaccgaggtggagcagctgtccaggtttcgtcacccaaacattgtggactttgctggctac
tgtgctcagaacggcttctactgcctggtgtacggcttcctgcccaacggctccctggaggaccgtctcc
actgccagacccaggcctgcccacctctctcctggcctcagcgactggacatccttctgggtacagcccg
ggcaattcagtttctacatcaggacagccccagcctcatccatggagacatcaagagttccaacgtcctt
ctggatgagaggctgacacccaagctgggagactttggcctggcccggttcagccgctttgccgggtcca
gccccagccagagcagcatggtggcccggacacagacagtgcggggcaccctggcctacctgcccgagga
gtacatcaagacgggaaggctggctgtggacacggacaccttcagctttggggtggtagtgctagagacc
ttggctggtcagagggctgtgaagacgcacggtgccaggaccaagtatctgaaagacctggtggaagagg
aggctgaggaggctggagtggctttgagaagcacccagagcacactgcaagcaggtctggctgcagatgc
ctgggctgctcccatcgccatgcagatctacaagaagcacctggaccccaggcccgggccctgcccacct
gagctgggcctgggcctgggccagctggcctgctgctgcctgcaccgccgggccaaaaggaggcctccta
tgacccaggagaactcctacgtgtccagcactggcagagcccacagtggggctgctccatggcagcccct
ggcagcgccatcaggagccagtgcccaggcagcagagcagctgcagagaggccccaaccagcccgtggag
agtgacgagagcctaggcggcctctctgctgccctgcgctcctggcacttgactccaagctgccctctgg
acccagcacccctcagggaggccggctgtcctcaggggacacggcaggagaatcgagctgggggagtgg
cccaggatcccggcccacagccgtggaaggactggcccttggcagctctgcatcatcgtcgtcagagcca
ccgcagattatcatcaaccctgcccgacagaagatggtccagaagctggccctgtacgaggatggggccc
tggacagcctgcagctgctgtcgtccagctccctcccaggcttgggcctggaacaggacaggcaggggcc
cgaagaaagtgatgaatttcagagctgatgtgttcacctgggcagatcccccaaatccggaagtcaaagt
tctcatggtcagaagttctcatggtgcacgagtcctcagcactctgccggcagtgggggtgggggcccat
gcccgcgggggagagaaggaggtggccctgctgttctaggctctgtgggcataggcaggcagagtggaac
cctgcctccatgccagcatctgggggcaaggaaggctggcatcatccagtgaggaggctggcgcatgttg
ggaggctgctggctgcacagacccgtgaggggaggagaggggctgctgtgcaggggtgtggagtagggag
ctggctcccctgagagccatgcagggcgtctgcagcccaggcctctggcagcagctctttgcccatctct
ttggacagtggccaccctgcacaatggggccgacgaggcctagggccctcctacctgcttacaatttgga
aaagtgtggccgggtgcggtggctcacgcctgtaatcccagcactttgggaggccaaggcaggaggatcg
ctggagcccagtaggtcaagaccagccagggcaacatgatgagaccctgtctctgccaaaaaattttta
aactattagcctggcgtggtagcgcacgcctgtggtcccagctgctggggaggctgaagtaggaggatca
tttatgcttgggaggtcgaggctgcagtgagtcatgattgtatgactgcactccagcctgggtgacagag -continued caagaccctgtttcaaaaagaaaaaccctgggaaaagtgaagtatggctgtaagtctcatggttcagtcc tagcaagaagcgagaattctgagatcctccagaaagtcgagcagcacccacctccaacctcgggccagtg tcttcaggctttactggggacctgcgagctggcctaatgtggtggcctgcaagccaggccatccctgggc gccacagacgagctccgagccaggtcaggcttcggaggccacaagctcagcctcaggcccaggcactgat tgtggcagaggggccactacccaaggtctagctaggcccaagacctagttacccagacagtgagaagccc ctggaaggcagaaaagttgggagcatggcagacagggaagggaaacattttcagggaaaagacatgtatc acatgtcttcagaagcaagtcaggtttcatgtaaccgagtgtcctcttgcgtgtccaaaagtagcccagg gctgtagcacaggcttcacagtgattttgtgttcagccgtgagtcacactacatgcccccgtgaagctgg gcattggtgacgtccaggttgtccttgagtaataaaaacgtatgttgcaataaaaaaaaaaaaaaaaaa.

IRAK1, transcript variant 2, is encoded by the following amino acid sequence (NCBI Accession No. NM_001025242 and SEQ ID NO: 31):

MAGGPGPGEPAAPGAQHFLYEVPPWVMCRFYKVMDALEPADWCQFAALI

VRDQTELRLCERSGQRTASVLWPWINRNARVADLVHILTHLQLLRARDI

ITAWHPPAPLPSPGTTAPRPSSIPAPAEAEAWSPRKLPSSASTFLSPAFP

GSQTHSGPELGLVPSPASLWPPPPSPAPSSTKPGPESSVSLLQGARPFPF

CWPLCEISRGTHNFSEELKIGEGGFGCVYRAVMRNTVYAVKRLKENADLE

WTAVKQSFLTEVEQLSRFRHPNIVDFAGYCAQNGFYCLVYGFLPNGSLED

RLHCQTQACPPLSWPQRLDILLGTARAIQFLHQDSPSLIHGDIKSSNVL

-continued

LDERLTPKLGDFGLARFSRFAGSSPSQSSMVARTQTVRGTLAYLPEEYIK

TGRLAVDTDTFSFGVVVLETLAGQRAVKTHGARTKYLKDLVEEEAEEAGV

ALRSTQSTLQAGLAADAWAAPIAMQIYKKHLDPRPGPCPPELGLGLGQLA

CCCLHRRAKRRPPMTQENSYVSSTGRAHSGAAPWQPLAAPSGASAQAAEQ

LQRGPNQPVESDESLGGLSAALRSWHLTPSCPLDPAPLREAGCPQGDTA

GESSWGSGPGSRPTAVEGLALGSSASSSSEPPQIIINPARQKMVQKLALY

EDGALDSLQLLSSSSLPGLGLEQDRQGPEESDEFQS.

IRAK1, transcript variant 3, is encoded by the following mRNA sequence (NCBI Accession No. NM_001025243 and SEQ ID NO: 32):

cgcggacccggccggcccaggcccgcgcccgccgcggccctgagaggccccggcaggtcccggcccggcg gcggcagccATGgccgggggggccgggcccgggggagcccgcagcccccggcgcccagcacttcttgtacg aggtgccgccctgggtcatgtgccgcttctacaaagtgatggacgccctggagcccgccgactggtgcca gttcgccgccctgatcgtgcgcgaccagaccgagctgcggctgtgcgagcgctccgggcagcgcacggcc agcgtcctgtggccctggatcaaccgcaacgcccgtgtggccgacctcgtgcacatcctcacgcacctgc agctgctccgtgcgcgggacatcatcacagcctggcaccctcccgccccgcttccgtccccaggcaccac tgccccgaggcccagcagcatccctgcacccgccgaggccgaggcctggagcccccggaagttgccatcc tcagcctccaccttcctctccccagcttttccaggctcccagacccattcagggcctgagctcggcctgg tcccaagccctgcttccctgtggcctccaccgccatctccagccccttcttctaccaagccaggcccaga gagctcagtgtccctcctgcagggagcccgccccttccgttttgctggcccctctgtgagatttcccgg ggcacccacaacttctcggaggagctcaagatcggggagggtggctttgggtgcgtgtaccgggcggtga tgaggaacacggtgtatgctgtgaagaggctgaaggagaacgctgacctggagtggactgcagtgaagca gagcttcctgaccgaggtggagcagctgtccaggtttcgtcacccaaacattgtggactttgctggctac tgtgctcagaacggcttctactgcctggtgtacggcttcctgcccaacggctccctggaggaccgtctcc actgccagacccaggcctgcccacctctctcctggcctcagcgactggacatccttctgggtacagcccg ggcaattcagtttctacatcaggacagccccagcctcatccatggagacatcaagagttccaacgtcctt ctggatgagaggctgacacccaagctgggagactttggcctggcccggttcagccgctttgccgggtcca gccccagccagagcagcatggtggcccggacacagacagtgcggggcaccctggcctacctgcccgagga gtacatcaagacgggaaggctggctgtggacacggacaccttcagctttggggtggtagtgctagagacc -continued

```
ttggctggtcagagggctgtgaagacgcacggtgccaggaccaagtatctggtgtacgagaggctagaga

agctgcaggcagtggtggcgggggtgcccgggcattcggaggccgccagctgcatccccccttccccgca

ggagaactcctacgtgtccagcactggcagagcccacagtggggctgctccatggcagcccctggcagcg

ccatcaggagccagtgcccaggcagcagagcagctgcagagaggccccaaccagcccgtggagagtgacg

agagcctaggcggcctctctgctgccctgcgctcctggcacttgactccaagctgccctctggacccagc

acccctcagggaggccggctgtcctcaggggacacggcaggagaatcgagctgggggagtggcccagga

tcccggcccacagccgtggaaggactggcccttggcagctctgcatcatcgtcgtcagagccaccgcaga

ttatcatcaaccctgcccgacagaagatggtccagaagctggccctgtacgaggatggggccctggacag

cctgcagctgctgtcgtccagctccctcccaggcttgggcctggaacaggacaggcaggggcccgaagaa

agtgatgaatttcagagctgatgtgttcacctgggcagatcccccaaatccggaagtcaaagttctcatg

gtcagaagttctcatggtgcacgagtcctcagcactctgccggcagtgggggtgggggcccatgcccgcg

ggggagagaaggaggtggccctgctgttctaggctctgtgggcataggcaggcagagtggaaccctgcct

ccatgccagcatctgggggcaaggaaggctggcatcatccagtgaggaggctggcgcatgttgggaggct

gctggctgcacagacccgtgaggggaggagaggggctgctgtgcaggggtgtggagtagggagctggctc

ccctgagagccatgcagggcgtctgcagcccaggcctctggcagcagctctttgcccatctctttggaca

gtggccaccctgcacaatggggccgacgaggcctagggccctcctacctgcttacaatttggaaaagtgt

ggccgggtgcggtggctcacgcctgtaatcccagcactttgggaggccaaggcaggaggatcgctggagc

ccagtaggtcaagaccagccagggcaacatgatgagaccctgtctctgccaaaaaatttttttaaactatt

agcctggcgtggtagcgcacgcctgtggtcccagctgctggggaggctgaagtaggaggatcatttatgc

ttgggaggtcgaggctgcagtgagtcatgattgtatgactgcactccagcctgggtgacagagcaagacc

ctgtttcaaaaagaaaaaccctgggaaaagtgaagtatggctgtaagtctcatggttcagtcctagcaag

aagcgagaattctgagatcctccagaaagtcgagcagcacccacctccaacctcgggccagtgtcttcag

gctttactggggacctgcgagctggcctaatgtggtggcctgcaagccaggccatccctgggcgccacag

acgagctccgagccaggtcaggcttcggaggccacaagctcagcctcaggcccaggcactgattgtggca

gaggggccactacccaaggtctagctaggcccaagacctagttacccagacagtgagaagcccctggaag

gcagaaaagttgggagcatggcagacagggaagggaaacattttcagggaaaagacatgtatcacatgtc

ttcagaagcaagtcaggtttcatgtaaccgagtgtcctcttgcgtgtccaaaagtagcccagggctgtag

cacaggcttcacagtgattttgtgttcagccgtgagtcacactacatgcccccgtgaagctgggcattgg

tgacgtccaggttgtccttgagtaataaaaacgtatgttgcaataaaaaaaaaaaaaaaaaa.
```

IRAK1, transcript variant 3, is encoded by the following amino acid sequence (NCBI Accession No. NM_001025243 and SEQ ID NO: 33):

```
MAGGPGPGEPAAPGAQHFLYEVPPWVMCRFYKVMDALEPADWCQFAALIV

RDQTELRLCERSGQRTASVLWPWINRNARVADLVHILTHLQLLRARDII

TAWHPPAPLPSPGTTAPRPSSIPAPAEAEAWSPRKLPSSASTFLSPAFP

GSQTHSGPELGLVPSPASLWPPPPSPAPSSTKPGPESSVSLLQGARPFPF

CWPLCEISRGTHNFSEELKIGEGGFGCVYRAVMRNTVYAVKRLKENADL

EWTAVKQSFLTEVEQLSRFRHPNIVDFAGYCAQNGFYCLVYGFLPNGSL

EDRLHCQTQACPPLSWPQRLDILLGTARAIQFLHQDSPSLIHGDIKSSN

VLLDERLTPKLGDFGLARFSRFAGSSPSQSSMVARTQTVRGTLAYLPEE
```

-continued

```
YIKTGRLAVDTDTFSFGVVVLETLAGQRAVKTHGARTKYLVYERLEKLQA

VVAGVPGHSEAASCIPPSPQENSYVSSTGRAHSGAAPWQPLAAPSGASA

QAAEQLQRGPNQPVESDESLGGLSAALRSWHLTPSCPLDPAPLREAGCP

QGDTAGESSWGSGPGSRPTAVEGLALGSSASSSSEPPQIIINPARQKMV

QKLALYEDGALDSLQLLSSSSLPGLGLEQDRQGPEESDEFQS.
```

Silencing Expression with MicroRNAs

The present invention comprises compositions with means to inhibit the activity of IL-1α, IL-1b, IL-1R1, IL-1R2, IL-1Ra3, IL-1RAP, or IRAK1, by delivering micro-RNA (miRNA) molecules to an ocular or adnexal tissue with an appropriate pharmaceutical carrier. Compositions that comprise a miRNA targeted to either IL-1α, IL-1b, IL-1R1, IL-1R2, IL-1Ra3, IL-1RAP, or IRAK1 antagonize the function of IL-1R1. The composition comprises one or more miRNA(s) that bind to one or more regions of IL-1α, IL-1b, IL-1R1, IL-1R2, IL-1Ra3, IL-1RAP, or IRAK1. The following table contains exemplary miRNAs that have been shown to partially or completely silence the expression of human IL-1α or IL-1R1.

TABLE 1

Summary of miRNAs, their human target genes, nucleotide sequences, and their sequence identifier numbers.

| Target Gene | miRNA | Polynucleotide sequence (5' to 3') | SEQ ID NO: |
|---|---|---|---|
| IL-1α | miR-30c | UGUAAACAUCCUACACUCUCAGC | 34 |
| IL-1α | miR-30b | UGUAAACAUCCUACACUCAGC | 35 |
| IL-1α | miR-30a-5p | UGUAAACAUCCUCGACUGGAAGC | 36 |
| IL-1α | miR-24 | UGGCUCAGUUCAGCAGGAACAG | 37 |
| IL-1R1 | miR-135b | UAUGGCUUUUCAUUCCUAUGUG | 38 |
| IL-1R1 | miR-326 | CCUCUGGGCCCUUCCUCCAG | 39 |
| IL-1R1 | miR-184 | UGGACGGAGAACUGAUAAGGGU | 40 |
| IL-1R1 | miR-214 | ACAGCAGGCACAGACAGGCAG | 41 |
| IL-1R1 | miR-203 | GUGAAAUGUUUAGGACCACUAG | 42 |
| IL-1R1 | miR-331 | GCCCCUGGGCCUAUCCUAGAA | 43 |
| IL-1R1 | miR-205 | UCCUUCAUUCCACCGGAGUCUG | 44 |

IL-1 and IL-1R-Mediated Signaling

As used herein, the phrase "inhibit an activity of an inflammatory interleukin-1 cytokine" is meant to describe the inhibition, prevention, diminution, reduction, decrease, repression, or interruption intracellular signaling initiated, communicated, or transduced from an IL-1 receptor. In one aspect of the invention, inhibition, prevention, diminution, reduction, decreases, repression, or interruption of intracellular signaling initiated, communicated, or transduced from an IL-1 receptor is achieved by preventing or decreasing binding of an IL-1 cytokine to an IL-1R. Alternatively, or in addition, transduction of intracellular signaling from an IL-1R is prevented by removing, silencing, or mutating a downstream effector or target within a signaling cascade. The expression and/or function or activity of downstream effectors and/or targets are removed (e.g., deleted, knocked-out, sequestered, denatured, degraded, etc.), silenced (degraded, transcriptionally or translationally repressed), or mutated (nucleotide or amino acid sequence encoding the active product is altered to encode a non-functional product) by genetic modification or administration of a therapeutic compound.

Exemplary downstream effectors and/or targets include, but are not limited to, one or more isoforms or homologs of an IL-1 (interleukin 1), an IL-1α (interleukin 1 alpha), an (interleukin 1 beta), an IL-1R (interleukin 1 receptor, type I), an IL-1 Ra (IIL-1R antagonist), an IL-1RAcP (IL-1R accessory protein), a TOLLIP (TOLL interacting protein), an IRAK1 (IL-1R associated kinase 1), an IRAK2 (IL-1R associated kinase 2), an IRAK 3 (IL-1R associated kinase 3), a MYD88 (myeloid differentiation primary response gene 88), an ECSIT (evolutionarily conserved signaling intermediate in Toll pathways), a TRAF6 (TNF-receptor associated factor 6), a MEKK1 (MAP ERK kinase kinase 1), a TAB1 (TAK1 binding protein 1), a TAK1 (transforming growth factor b activated kinase 1), a NIK (NFkB Inducing Kinase), a RKIP (Raf kinase inhibitor protein), a MEK3 (Mitogen-Activated Protein Kinase Kinase 3; MEK3 or MKK3), a MEK6 (Mitogen-Activated Protein Kinase Kinase 6; MEK6 or MKK6), a MAPK14 (mitogen activated protein kinase 14), a MAPK8 (mitogen activated protein kinase 8), a MEKK1 (mitogen activated protein kinase kinase kinase 1), a MAP3K14 (mitogen activated protein kinase kinase kinase 14), a MEKK7 (mitogen activated protein kinase kinase kinase 7 or MKK7), a MAP3K7IP1 (mitogen activated protein kinase kinase kinase 7 interacting protein 1), a JNK (Jun N-terminal kinase), p38 (also known as p38 MAPK or p38 mitogen activated protein kinase), cJUN (jun oncogene), AP-1 (activator protein 1; transcription factor), IL-6 (interleukin 6, also known as interferon beta 2), TNFα (tumor necrosis factor-alpha), a TNF (tumor necrosis factor superfamily member), an IFNα (interferon alpha, interferon alpha 1), an IFNβ (interferon beta, interferon beta 1), a TGFβ1 (transforming growth factor beta 1), a TGFβ2 (transforming growth factor beta 2), a TGFβ3 (transforming growth factor beta 3), an IKKα (inhibitor of kappa light polypeptide gene enhancer in B-cells, kinase alpha), an IKKβ (inhibitor of kappa light polypeptide gene enhancer in B-cells, kinase beta), a IκBα (nuclear factor of kappa light polypeptide gene enhancer in B-cells inhibitor, alpha), a Chuk (conserved helix-loop-helix ubiquitous kinase), and a NFκB (nuclear factor of kappa light polypeptide gene enhancer in B-cells 1; also known as p105). Additional signaling molecules and relationships are defined by O'Neill, L. A. J. and Greene, C. 1998. Journal of Leukocyte Biology. 63: 650-657.

The inhibition of an activity of an interleukin-1 cytokine is determined by sampling the cornea and determining the abundance of a polynucleotide or polypeptide which encodes for component of an IL-1R signaling cascade. An increase or decrease in the abundance of a polynucleotide or polypeptide which encodes for component of an IL-1R signaling cascade following administration of a therapeutic composition of the invention compared to the abundance of the component of an IL-1R signaling cascade prior to the administration indicates inhibition of an activity of an inflammatory interleukin-1 cytokine.

Figure 5:
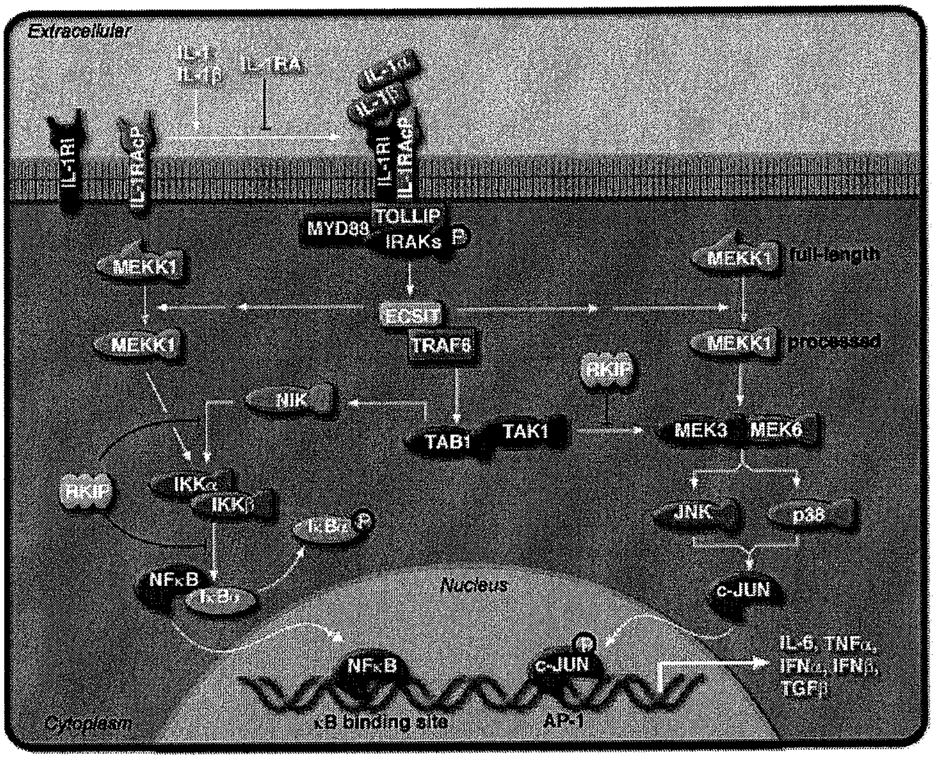
FIG. 5 is a schematic representation of signaling pathways that are transduced from the IL-1RI and the downstream effectors involved in carrying these intracellular signals (drawing reproduced from BioCarta website).
Figure 6:
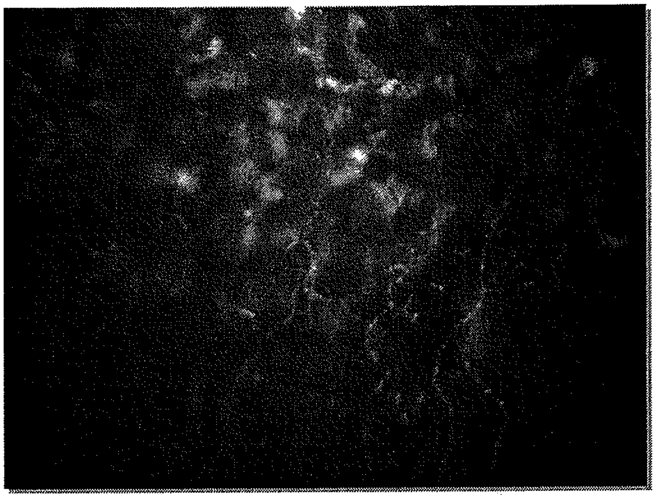
FIG. 6 is an in vivo confocal microscopic image (Confoscan 4; Nidek, Inc.) of subbasal nerve fibers in a healthy cornea of a 42-year-old male subject. Nerve bundles show a preferred orientation in the superior-inferior direction. Note the nerve fibers appear almost straight or slightly tortuous.
Figure 7:
FIG. 7 is an in vivo confocal microscopic image (Confoscan 4; Nidek, Inc.) of subbasal nerve fibers in the cornea of a 56-year-old female subject with herpes zoster ophthalmicus. Note the significant decrease in the number of nerve bundles compared to the normal cornea. This microphotograph also shows signs of other nerve abnormalities such as high tortuosity, increased bead-like nerve formations, and an abnormal branching pattern.

Specifically, FIG. 5 shows the functional interrelationships between components of two exemplary signaling cascades. The arrows between components in this figure indicate that the component preceding the arrow activates the component following the arrow. Conversely, the blunted lines indicated that the component preceding the blunted line inhibits the activity or function of the component following the blunted line.

Briefly, the IL-1R, type I, binds IL-1β, however, IL-1R requires the IL-1 receptor accessory protein (IL-1RAcP) to transduce a signal. IL-1 binding causes activation of two kinases, IRAK-1 and IRAK-2, associated with the IL-1 receptor complex. IRAK-1 (IL-1 Receptor Associated Kinase) activates and recruits TRAF6 to the IL-1 receptor complex. TRAF6 activates two pathways, one leading to NF-kB activation and another leading to c-jun activation. The TRAF associated protein ECSIT leads to c-Jun activation through the Map kinase/JNK signaling system. TRAF6 also signals through the TAB1/TAK1 kinases to trigger the degradation of I-kB, and activation of NF-kB.

For instance, in certain embodiments of the invention, a decrease in the abundance or absence of the processed form of MEKK1, a decrease in the abundance or absence of phosphorylated IκBα, a decrease in the abundance or absence of phosphorylated c-JUN, a decrease in the abundance or absence of ICAM-1, or a decrease in the abundance or absence of IL-6, TNFα, IFNα, IFNβ, TGFβ is indicative of inhibition of an interleukin-1 cytokine. Similarly, a decrease or absence of activity or function of any of the above-listed components is indicative of inhibition of an interleukin-1 cytokine.

Pharmaceutically-Appropriate Carriers

Exemplary compounds incorporated to facilitate and expedite local delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alpha-terpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist.

Optionally, the composition further contains a compound selected from the group consisting of a physiological acceptable salt, poloxamer analogs with carbopol, carbopol/hydroxypropyl methyl cellulose (HPMC), carbopol-methyl cellulose, N-acetyl cysteine, carboxymethylcellulose (CMC), hyaluronic acid, cyclodextrin, and petroleum.

Examples

Example 1: Effect of IL-1 Blockade on Central Nerve Regeneration in Epithelial Disease It was observed that subjects with the most severe clinical signs of dry eye reported feeling surprising improvement after administration of IL-1 blockade. Upon further investigation, patients with severe dry eye were found to also suffer after administration of IL-1 blockade corneal nerve damage or even loss of nerve function. To better elucidate the mechanism of this unexpected improvement following treatment, the contribution of nerve damage and function to the normal and pathological processes of tear production and dry eye was investigated.

To examine the role of IL-1 blockade in corneal nerve homeostasis, regeneration of the corneal subbasal nerve plexus and terminal epithelial branches after epithelial debridement was measured. Mice were anesthetized, and a 2-mm circular corneal epithelial defect was made in one eye of each anesthetized mouse using a scalpel blade. One group of mice (n=5) was treated with topical eye drop of IL-1Ra 2.5% mixed with carboxymethylcellulose 1%, 3 times a day for 7 days. The control group (n=5) was treated using vehicle (carboxymethylcellulose 1%), 3 times a day for 7 days. After 7 days, animals were euthanized, and corneas were removed and fixed in 4% Para formaldehyde for 40 minutes at room temperature. Corneas were washed with PBS. Permeabilization and blocking was achieved with 2-hour incubation in 2% BSA in PBS and 0.2% Triton X-100. Corneas were incubated with rabbit anti-mouse β III tubulin primary antibody at a dilution of 1:200 for 16 hours at 4°. After three washes in PBS corneas were incubated in goat anti-rabbit secondary antibody conjugated to rhodamine at a dilution of 1:200 for 2 hours at room temperature. The corneas were coverslipped with mounting medium and imaged. The corneas were photographed at the level of the subbasal nerve plexus and terminal branching in cornea paracentral regions in the area of the wound (FIG. 1). For the treated eye, nerve density at the level of terminal branching was normalized to the contralateral normal cornea. The results of this experiment showed that in the IL-1Ra-treated group, the percent density of regenerated nerve at the level of basal epithelial cell was 80% compared to 15% in the vehicle-treated group.

Figure 2:
FIG. 2 is a series of in vivo confocal images (Confoscan 4; Nidek Technologies) of subbasal corneal nerve before (left) and after (right) a one-month treatment with IL-1Ra 2.5% in a dry eye patient, showing an increase of 25% in nerve density after the treatment compared to the baseline.
Figure 3:
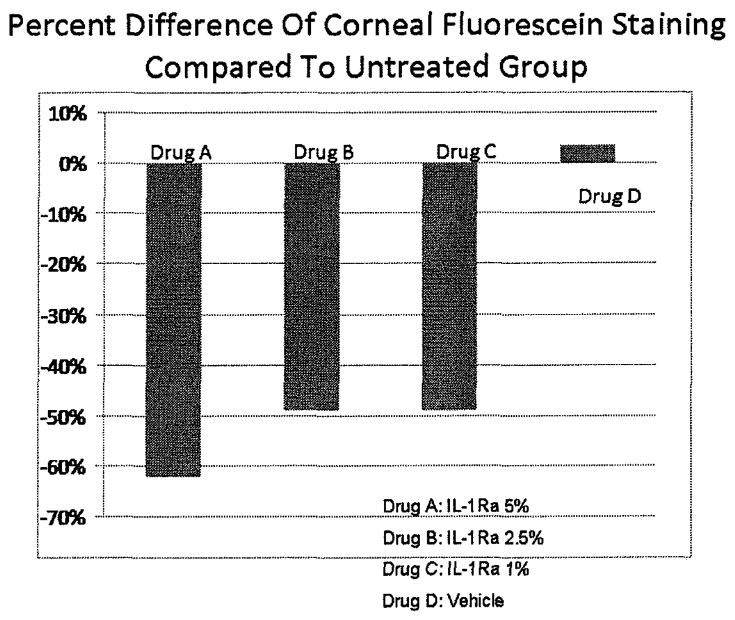
FIG. 3 is a graph of the percent difference of corneal fluorescein staining observed in mouse models of dry eye treated with varying concentrations of IL-1Ra compared to untreated animals. As the graph shows, all concentrations of IL-1Ra (1%, 2.5%, and 5%) can decrease the corneal fluorescein staining score; however, the percent reduction of corneal fluorescein staining was modestly higher in the group that received topical IL-1Ra at a concentration of 5%.
Figure 4:
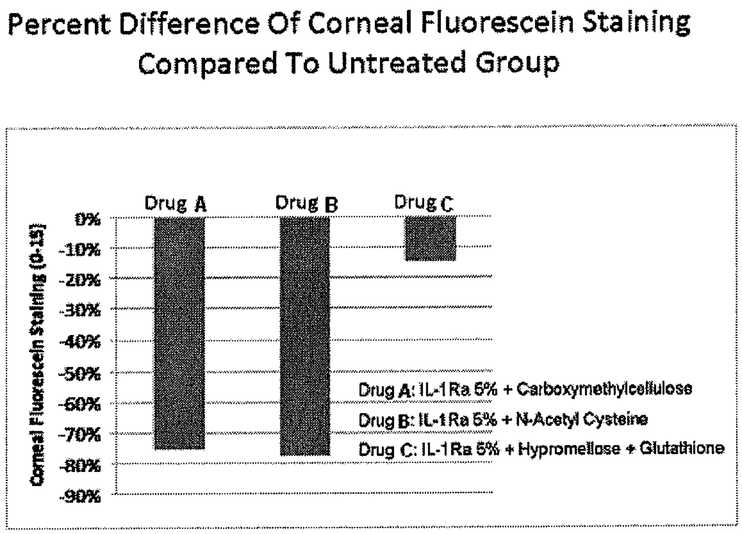
FIG. 4 is a graph of the percent difference of corneal fluorescein staining observed in mouse models of dry eye treated with varying formulations of IL-1Ra compared to untreated animals. As the graph shows, the percent reduction of corneal fluorescein staining was highest in the groups that received topical IL-1Ra 5% mixed with N-acetyl cysteine 10% and the group that received topical IL-1Ra 5% mixed with carboxymethyl cellulose 1%.

In a clinical human study in patients with dry eye-associated ocular surface disease using in-vivo confocal microscopy (Confoscan 4; Nidek Technologies), corneal nerve morphology at the level of subbasal corneal nerve was assessed before and after one-month treatment with topical IL-1Ra 2.5% three times a day (FIG. 2). After the treatment with IL-1 blockade in a total of 6 patients, the sum of the length of the nerves per image (nerve fiber density) was increased by 25% compared to baseline. The improvement in corneal nerve density was correlated with the reduction of signs and symptoms of dry eye in these patients.

IL-1 blockade, therefore, helps the epithelium improve its maintenance of corneal health by increasing nerve regeneration, which in turn breaks the vicious cycle of epithelial disease and nerve damage. Thus, IL-1 blockade can be used in all ophthalmologic conditions that affect the corneal epithelial health, including all forms of dry eye syndrome, all form of ocular surface diseases, corneal surgeries such as refractive surgeries (PRK, LASEK, Epi-LASIK, LASIK), corneal transplantation, epithelial debridement, ocular surface reconstruction, herpetic keratitis, neurotrophic keratitis, exposure keratopathy, diabetes mellitus, trigeminal nerve damage. Non-ophthalmic applications of IL-1 blockade would be all forms of peripheral neuropathy including diabetic peripheral neuropathy.

Example 2: Effect of IL-1 Blockade on Dry-Eye Induced Lymphangiogenesis

Corneal angiogenesis is involved in the pathogenesis of adaptive immunity to corneal antigens and in inducing ocular surface disease. Lymphatic vessels are crucial for migration of resident antigen presenting cells to the draining lymph nodes and induction of adaptive immunity, but there is no information about the role of lymphangiogenesis in dry-eye associated ocular surface disease. In a mouse model of dry eye, it was determined whether IL-1 blockade can reduce dry-eye induced lymphangiogenesis. Dry eye was induced in female C57BL/6 mice (n=10) by exposure to the controlled environment chamber and to systemic scopolamine. After 2 days, one group of mice (n=5) received topical IL-1Ra 2.5% mixed with carboxymethylcellulose 1% three times a day, and the second group received only the vehicle (carboxymethylcellulose 1%). After 5 days of treatment, animals were euthanized, and corneas were removed and fixed in 4% Para formaldehyde for 40 minutes at room temperature. Immunohistochemical staining for lymphatic vessels and blood vessels was performed on corneal flat mounts. Immunohistochemical staining against LYVE-1 (lymphatic endothelium—specific hyaluronic acid receptor) was performed with purified antibody followed by rhodamine conjugated secondary antibody. Immunohistochemical staining was also performed with FITC-conjugated CD31. To quantify the level of blood vessel formation and lymphatic vessel formation, low magnification (2×) micrographs were captured and the area covered by lymph neovessels were calculated and expressed as % of total corneal area. IL-1Ra-treated corneas showed on average 60% less lymphangiogenesis activity compared to vehicle-treated corneas. In addition, blockade of IL-1 led to the immune cells having a lower level of maturity, which renders them less able to sensitize T cells.

The results of this experiment show that the compounds having the inhibitory activity against IL-1 on prevention of dry-eye associated lymphangiogenesis are useful to minimize the induction of adaptive immunity and autoimmunity in dry-eye associated ocular surface disease.

Example 3: Concentration of Topical IL-1Ra

With respect to effects of IL-1 blockade on dry eye disease, different concentrations (1%, 2.5%, and 5%) of topical IL-1Ra mixed with carboxymethylcellulose 1% were tested in a mouse model of dry eye. Dry eye was induced in female C57BL/6 mice (n=20) by exposure to the controlled environment chamber and to systemic scopolamine. After 2 days, mice were divided in 5 groups. The first, second, and third groups of mice (4 mice in each group) received topical IL-1Ra 5%, 2.5%, and 1% respectively, mixed with carboxymethylcellulose 1% in frequency of 3 times a day; the fourth group (n=4) received vehicle (carboxymethylcellulose 1%) in frequency of 3 times a day; and the fifth group (n=4) left untreated. After 5 days of treatment, corneal fluorescein staining was performed by applying 0.5 μL of 1% fluorescein by micropipette into the inferior conjunctival sac of the mouse eye. The cornea was examined with a slit lamp biomicroscope in cobalt blue light 3 minutes after fluorescein instillation. Punctuate staining was recorded in a masked fashion with a standardized (National Eye Institute) grading system of 0 to 3 for each of the five areas in which the corneal surface was divided. This experiment showed that all concentrations of IL-1Ra (1%, 2.5%, and 5%) can decrease the corneal fluorescein staining score, however, percent reduction of corneal fluorescein staining was modestly higher in the group that received topical IL-1Ra with concentration of 5%.

Example 4: Formulation of Topical IL-1Ra

With respect to effects of IL-1 blockade on dry eye disease, IL-1Ra 5% mixed with different vehicles was tested in a mouse model of dry eye. Dry eye was induced in female C57BL/6 mice (n=20) by exposure to the controlled environment chamber and to systemic scopolamine. After 2 days, mice were divided in 4 groups. The first group of mice (n=5) received topical IL-1Ra 5% mixed with carboxymethylcellulose 1% in frequency of 3 times a day; the second group (n=5) received topical IL-1Ra 5% mixed with N-acetyl cysteine 10% in frequency of 3 times a day; the third group (n=5) received topical IL-1Ra 5% mixed with hypromellose (hydroxypropyl methylcellulose) 0.3% and glutathione 0.3 mmol/L; and the fourth group (n=5) left untreated. After 5 days of treatment, corneal fluorescein staining was performed by applying 0.5 μL of 1% fluorescein by micropipette into the inferior conjunctival sac of the mouse eye. The cornea was examined with a slit lamp biomicroscope in cobalt blue light 3 minutes after fluorescein instillation. Punctuate staining was recorded in a masked fashion with a standardized (National Eye Institute) grading system of 0 to 3 for each of the five areas in which the corneal surface was divided. This experiment showed that percent reduction of corneal fluorescein staining was significantly higher in the group received topical IL-1Ra 5% mixed with N-acetyl cysteine 10% and the group received topical IL-1Ra 5% mixed with carboxymethylcellulose 1%.

Example 5: Minimization or Prevention of Corneal Nerve Degeneration

To examine the role of IL-1 blockade in corneal nerve homeostasis, minimization and prevention of nerve degeneration of the corneal subbasal nerve plexus and terminal epithelial branches was measured. One group of mice (n=5) was treated with topical eye drop of IL-1Ra, 2.5% mixed with carboxymethylcellulose 1%, 3 times a day for 7 days. The control group (n=5) was treated using vehicle (carboxymethylcellulose 1%), 3 times a day for 7 days. Mice were then anesthetized, and a 2-mm circular corneal epithelial defect was made in one eye of each anesthetized mouse using a scalpel blade. After 7 days, animals were euthanized, and corneas were removed and fixed in 4% Para formaldehyde for 40 minutes at room temperature. Corneas were washed with PBS. Permeabilization and blocking was achieved with 2-hour incubation in 2% BSA in PBS and 0.2% Triton X-100. Corneas were incubated with rabbit anti-mouse β III tubulin primary antibody at a dilution of 1:200 for 16 hours at 4°. After three washes in PBS corneas were incubated in goat anti-rabbit secondary antibody conjugated to rhodamine at a dilution of 1:200 for 2 hours at room temperature. The corneas were coverslipped with mounting medium and imaged. The corneas are photographed at the level of the subbasal nerve plexus and terminal branching in cornea paracentral regions in the area of the wound. For the treated eye, nerve density at the level of terminal branching is normalized to the contralateral normal cornea. The results of this experiment show that that in the IL-1Ra-treated group, the percent density of degenerated nerve at the level of basal epithelial cell was decreased compared to the vehicle-treated group.

IL-1 blockade, therefore, can help the epithelium improve its maintenance of corneal health by minimizing or preventing nerve degeneration which in turn can break the vicious cycle of epithelial disease and nerve damage. Thus, IL-1 blockade can be used in all ophthalmologic conditions that affect the corneal epithelial health including all forms of dry eye syndrome, all form of ocular surface diseases, corneal surgeries such as refractive surgeries (PRK, LASEK, Epi-LASIK, LASIK), corneal transplantation, epithelial debridement, ocular surface reconstruction, herpetic keratitis, neurotrophic keratitis, exposure keratopathy, diabetes mellitus, trigeminal nerve damage. Non-ophthalmic applications of IL-1 blockade would be all forms of peripheral neuropathy including diabetic peripheral neuropathy.

Example 6: IL-1 and IL-17 Blockade Provides Unexpected Protection of Corneal Nerves As described in WO/2009/089036, which is incorporated herein by reference, the method comprises administration of a compound that inhibits binding of an inflammatory IL-17 cytokine to the IL-17 receptor complex.

A method for regenerating corneal nerves is also carried out by locally administering to an eye of a subject a composition comprising a polynucleotide, a polypeptide, an antibody, a compound, or a small molecule that inhibits or modifies the transcription, transcript stability, translation, modification, localization, secretion, or function of a polynucleotide or polypeptide encoding an inflammatory interleukin-17 cytokine or any component of the IL-17 receptor complex.

The composition may comprise a neutralizing or function-blocking antibody against IL-17 and/or a receptor complex. The neutralizing or function-blocking antibody against IL-17 may be a reformulated or humanized derivative of or bind to the epitope of human IL-17 affinity purified polyclonal antibody (Catalog #AF-317-NA, R&D Systems), human IL-17 allophycocyanin monoclonal antibody (clone 41802) (Catalog #IC3171A, R&D Systems), human IL-17 biotinylated affinity purified polyclonal antibody (Catalog #BAF317, R&D Systems), human IL-17 monoclonal antibody (clone 41802)(Catalog #MAB3171, R&D Systems), human IL-17 monoclonal antibody (clone 41809)(Catalog #MAB317, R&D Systems), human IL-17 phycoerythrin monoclonal antibody (clone 41802)(Catalog #IC3171P, R&D Systems), mouse IL-17 affinity purified polyclonal antibody (Catalog #AF-421-NA, R&D Systems), mouse IL-17 biotinylated affinity purified polyclonal antibody (Catalog #BAF421, R&D Systems), mouse IL-17 monoclonal antibody (clone 50101)(Catalog #MAB721, R&D Systems), or mouse IL-17 monoclonal antibody (clone 50104) (Catalog #MAB421, R&D Systems). Preferably, the neutralizing or function-blocking antibody against IL-17 may be a reformulated or humanized derivative of or bind to the epitope of monoclonal anti-human IL-17 antibody, (Clone: 41809, Catalog #MAB317, R&D Systems), anti-human IL-17 antibody, polyclonal raised in Goat, (Catalog #AF-317-NA, R&D Systems), or recombinant human IL-17 RTFc chimera (Catalog #177-IR, R&D Systems).

By "reformulate" is meant altering the composition to make it suitable for topical administration, subconjunctival administration, episcleral space administration, subcutaneous administration, or intraductal administration. Preferred formulations are in the form of a solid, a paste, an ointment, a gel, a liquid, an aerosol, a mist, a polymer, a contact lens, a film, an emulsion, or a suspension. In one aspect, the formulations are administered topically, e.g., the composition is delivered and directly contacts the eye. Optionally, the compositions are administered with a pharmaceutically acceptable liquid carrier, e.g., a liquid carrier, which is aqueous or partly aqueous. Alternatively, the compositions are associated with a liposome (e.g., a cationic or anionic liposome).

The neutralizing or function-blocking antibody against an IL-17 receptor (I1-17R) may be a reformulated or humanized derivative of or bind to the epitope of human IL-17R affinity purified polyclonal antibody (Catalog #AF 177, R&D Systems), human IL-17R allophycocyanin monoclonal antibody (clone 133617) (Catalog #FAB177A, R&D Systems), human IL-17R biotinylated affinity purified polyclonal antibody (Catalog #BAF 177, R&D Systems), human IL-17R fluorescein monoclonal antibody (clone 133617) (Catalog #FAB177F, R&D Systems), human IL-17R monoclonal antibody (clone 133617)(Catalog #MAB 177, R&D Systems), human IL-17R monoclonal antibody (clone 133621)(Catalog #MAB 1771, R&D Systems), human IL-17R phycoerythrin monoclonal antibody (clone 133617) (Catalog #FAB 177P, R&D Systems), mouse IL-17R affinity purified polyclonal antibody (Catalog #AF448A, R&D Systems), mouse IL-17R biotinylated affinity purified polyclonal antibody (Catalog #BAF448, R&D Systems), or mouse IL-17R monoclonal antibody (clone 105828)(Catalog #MAB448, R&D Systems).

The neutralizing or function-blocking antibody against an IL-17 may be a reformulated or humanized derivative of, or bind to the epitope of, one or more mouse anti-IL-17A (SKU #s including but not limited to, 7172, 7173, 7175, 7177, 8171, 7371, 7971, and 7370, eBioscience) or mouse anti-IL-17F (SKU #s including, but not limited to, 7471 and 8471, eBioscience). The neutralizing or function-blocking antibody against an IL-17 may be a reformulated or humanized derivative of one or more human anti-IL-17A (SKU #s including, but not limited to, 7178, 7179, 8179, 7176, 7976, and 7876 or human anti-IL-17F SKU #s including, but not limited to, 8479, eBioscience). Preferably, the neutralizing or function-blocking antibody against an IL-17 may be a reformulated or humanized derivative of, or bind to the epitope of functional grade purified anti-human IL-17A antibody (Clone: eBio64CAP17, Catalog #16-7178. eBioscience).

Alternatively, the composition may comprise an intrabody that binds to the IL-17 receptor complex or any synthetic intermediate of IL-17 or the IL-17 receptor complex. The composition may alternatively, or in addition, comprise a soluble fragment of the IL-17 receptor complex which binds IL-17.

Exemplary polypeptides include, but are not limited to, fusion and/or chimeric proteins capable of disrupting IL-17 function. Moreover, the composition comprises morpholino antisense oligonucleotides, microRNAs (miRNAs), short hairpin RNA (shRNA), or short interfering RNA (siRNA) to silence gene expression.

Contemplated function-blocking antibodies targeted against an IL-17 cytokine or an IL-17 receptor are monoclonal or polyclonal. The contemplated antibody binds to one or more sequences within an IL-17 or IL-17 receptor polypeptide. The antibody is alternatively an intrabody. In some embodiments, the antibody comprises a single chain, a humanized, a recombinant, or a chimeric antibody. One or more compounds are directly or indirectly conjugated onto this antibody.

Antagonists of IL-17 and/or its receptor complex are administered either simultaneously or sequentially with an antagonist of IL-1 and/or its receptor.

Human IL-17 is encoded by the mRNA sequence of NCBI Accession No. NM 002190, alternatively called IL-17A. Human IL-17 is encoded by the amino acid sequence of NCBI Accession No. NM_002190, alternatively called IL-17A. Human IL-17B is encoded by the mRNA sequence of NCBI Accession No. NM_014443. Human IL-17B is encoded by the amino acid sequence of NCBI Accession No. NM_014443. Human IL-17C is encoded by the mRNA sequence of NCBI Accession No. NM_013278. Human IL-17C is encoded by the amino acid sequence of NCBI Accession No. NM_013278. Human IL-17D is encoded by the mRNA sequence of NCBI Accession No. NM_138284. Human IL-17D is encoded by the amino acid sequence of NCBI Accession No. NM_138284. Human IL-17E is encoded by the mRNA sequence of NCBI Accession No. AF305200. Human IL-17E is encoded by the amino acid sequence of NCBI Accession No. AF305200. Human IL-17F is encoded by the mRNA sequence of NCBI Accession No. NM 052872. Human IL-17F is encoded by the amino acid sequence of NCBI Accession No. NM_052872.

IL-17 receptor antagonist (IL-17RA) is encoded by the mRNA sequence of NCBI Accession No. NM 014339. IL-17RA is encoded by the amino acid sequence of NCBI Accession No. NMJ4339. IL-17RB is encoded by the mRNA sequence of NCBI Accession No. NM_018725. IL-17RB is encoded by the amino acid sequence of NCBI Accession No. NM_018725. IL-17RC, transcript variant 1, is encoded by the mRNA sequence of NCBI Accession No. NM 153461. IL-17RC, transcript variant 1, is encoded by the amino acid sequence of NCBI Accession No. NM_153461. IL-17RC, transcript variant 2, is encoded by the mRNA sequence of NCBI Accession No. NMJ 53460. IL-17RC, transcript variant 2, is encoded by the amino acid sequence of NCBI Accession No. NM_153460. IL-17RC, transcript variant 3, is encoded by the mRNA sequence of NCBI Accession No. NM_032732. IL-17RC, transcript variant 3, is encoded by the amino acid sequence of NCBI Accession No. NM_032732. IL-17RD, transcript 1, is encoded by the mRNA sequence of NCBI Accession No. NMJ)01080973. IL-17RD, transcript 1, is encoded by the amino acid sequence of NCBI Accession No. NMJ) O1080973. IL-17RD, transcript 2, is encoded by the mRNA sequence of NCBI Accession No. NM O1 7563. IL-17RD, transcript 2, is encoded by the amino acid sequence of NCBI Accession No. NM_017563. IL-17RE, transcript variant 1, is encoded by the mRNA sequence of NCBI Accession No. NM 1 53480. IL-17RE, transcript variant 1, is encoded by the amino acid sequence of NCBI Accession No. NM_153480. IL-17RE, transcript variant 2, is encoded by the mRNA sequence of NCBI Accession No. NM_153481. IL-17RE, transcript variant 2, is encoded by the amino acid sequence of NCBI Accession No. NM_153481. IL-17RE, transcript variant 5, is encoded by the mRNA sequence of NCBI Accession No. NM_153483. IL-17RE, transcript variant 5, is encoded by the amino acid sequence of NCBI Accession No. NM_153483.

Figure 8:
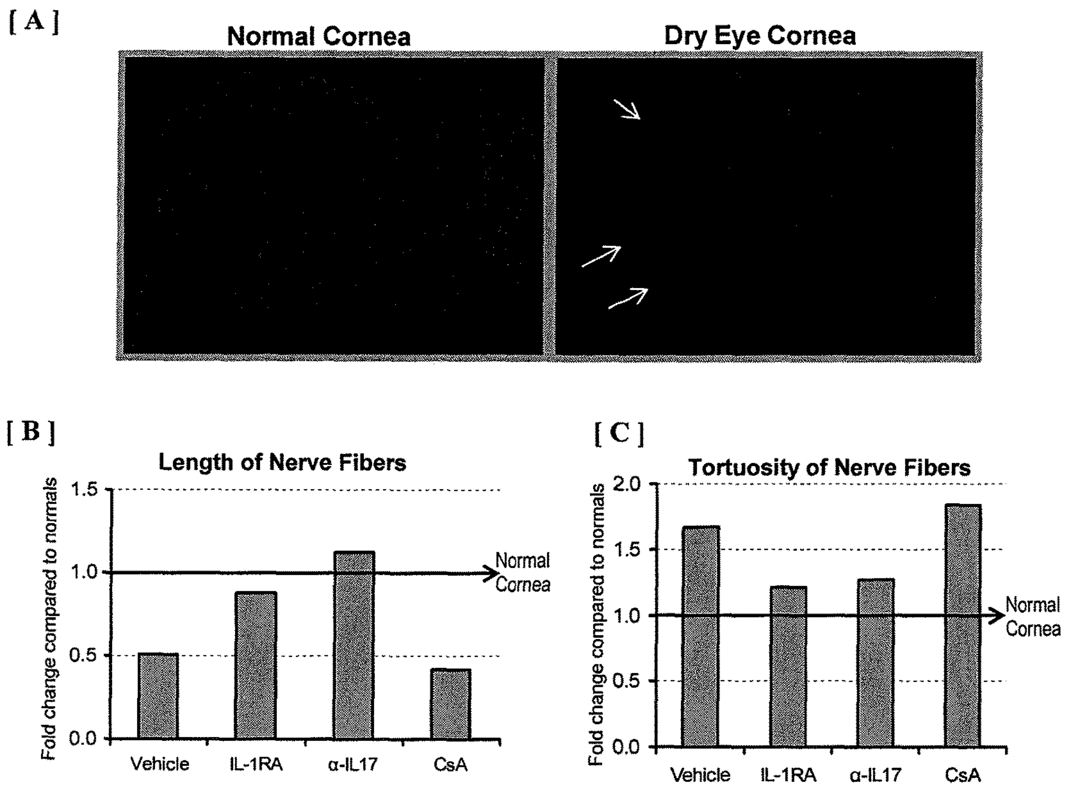
FIG. 8A is a series of representative micrographs showing nerve fiber distribution in the central cornea of normal and dry eye disease (DED) mice. The white arrows show nerve fiber loss (reduced nerve length) in the cornea of dry eye mice.
FIG. 8B is a bar diagram showing fold change (from normal cornea shown as horizontal solid arrow) in corneal nerve fiber length in DED mice treated topically with vehicle, IL-1Ra, anti-IL17-antibody, and cyclosporine-1 (CsA).
FIG. 8C is a bar diagram showing fold change (from normal cornea shown as horizontal solid arrow) in corneal nerve fiber tortuosity in DED mice treated with vehicle, IL-1Ra, anti-IL17-antibody, and cyclosporine-1 (CsA).

To study the effect of IL-17 blockade on corneal neuropathy, an art-recognized murine model of dry eye disease (DED) was used. As described above, DED was induced in female C57BL/6 mice by exposure to a desiccating environment in a controlled environment chamber and to systemic scopolamine (FIG. 8A). After induction of DED for 9-10 days, whole mount corneas were immunostained for nerve-specific β-tubulin-III, and then epifluorescence micrographs were captured and processed under an automated Matlab based software nerve quantification. Nerve fiber length and nerve fiber tortuosity (indices of neuroregeneration/neurodegeneration) were analyzed as described below.

Both the anti-cytokine therapies, including IL-1Ra and anti-IL17 prevented loss of nerve fibers in DED corneas (FIG. 8B). By contrast, use of a lubricating drop ("Vehicle") or CsA showed ~2-fold decrease in the fiber length compared to those in normal corneas, suggesting that standard treatments against DED (lubrication or topical cyclosporine) do not protect significantly against nerve damage. Similarly, IL-1Ra and anti-IL17 therapies maintain the nerve fiber tortuosity levels similar to that seen in normal corneas, whereas DED corneas treated with vehicle or CsA show ~2-fold increase in the nerve fiber tortuosity as compared to the normals (FIG. 8C).

These results demonstrate that blockade of Interleukin-1 (IL-1) either directly using topical IL-1 receptor antagonist (IL-1Ra) or indirectly by blocking IL-17 (a potent inducer of IL-1β by target cells) using anti-IL17-antibody inhibits corneal neuropathy, including the symptoms of nerve loss (fiber length) and nerve tortuosity. The treatments that block IL-1 and IL-17 promote nerve fiber length, but suppress nerve fiber tortuosity.

The nerve tortuosity data and the nerve fiber length data described above indicate that conventional therapies for DED (topical lubricating tear ointment or topical cyclosporine-A) do not protect significantly against nerve damage. Although ocular surface inflammation associated with DED is often correlated with elevated levels of tear nerve growth factor, which is typically reduced with steroids such as 0.1% prednisolone, the results above indicate that such therapy are ineffective at inducing corneal nerve regeneration. Thus, administration of such immunosuppressive agents (e.g., macrolides such as cyclosporin A (e.g., Restasis®), or corticosteroids such as prednisolone) are preferably not administered with the compositions described herein.

Example 7: Combination Therapy Blockade of IL-1 and IL-17 Enhances Corneal Nerve Regeneration IL-1 is a major initiator of the inflammatory process upstream of T cell activation and plays a crucial role in precipitating the inflammation by promoting the induction or expansion of IL-17-secreting T cells. IL-1 and IL-17 work synergistically and enhance secretion of each other in vivo.

An IL-17 blocking treatment is applied to a cornea, along with an IL-1 blocking treatment. The co-administration of IL-1 and IL-17 blocking treatment enhances corneal nerve regeneration such that the amount of nerve fibers associated with damaged corneas is increased compared to untreated corneas. The co-administration of IL-1 and IL-17 blocking treatment synergistically enhances corneal nerve regeneration in the case of immune-mediated corneal nerve damage.

Example 8: Efficacy of Topical Application of IL-1 Ra in Ocular Surface Inflammatory Disorders in a Human An IL-1Ra open label study was utilized to determine the efficacy of IL-1Ra in treating ocular surface inflammatory disorders in a human. Seventy patients were enrolled in the study and various numbers of patients were available for monthly checkups as follows: month 1 (44 patients), month 3 (37 patients), month 5 (22 patients), and month 7 (17 patients). None of these patients had severe meibomian gland dysfunction (MGD, also called posterior blepharitis) defined as grade 3 meibomian secretions (secretions retain shape after expression), or grade 4 lid margin disease (marked diffuse redness of both lid margins and skin), or grade 4 conjunctival hyperemia (marked dark redness of the palpebral and/or bulbar conjunctiva). Of note, patients with MGD/meibomian gland dysfunction alone do not develop significant corneal neuropathy (Foulks and Bron, 2003 Ocul Surf, 107-26).

Figure 9A:
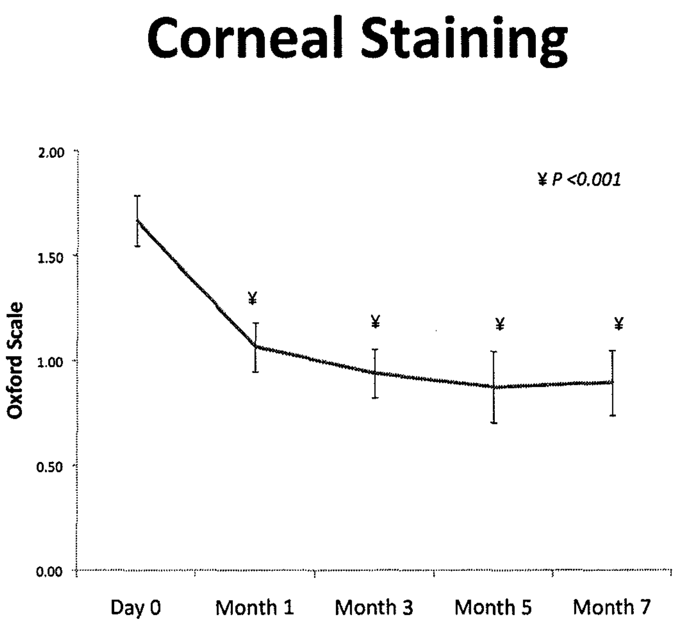
FIG. 9A is a line graph demonstrating mean corneal fluorescein staining in 70 human patients with ocular surface inflammatory disorder and dry eyes treated with topical IL-1 receptor antagonist.
Figure 9B:
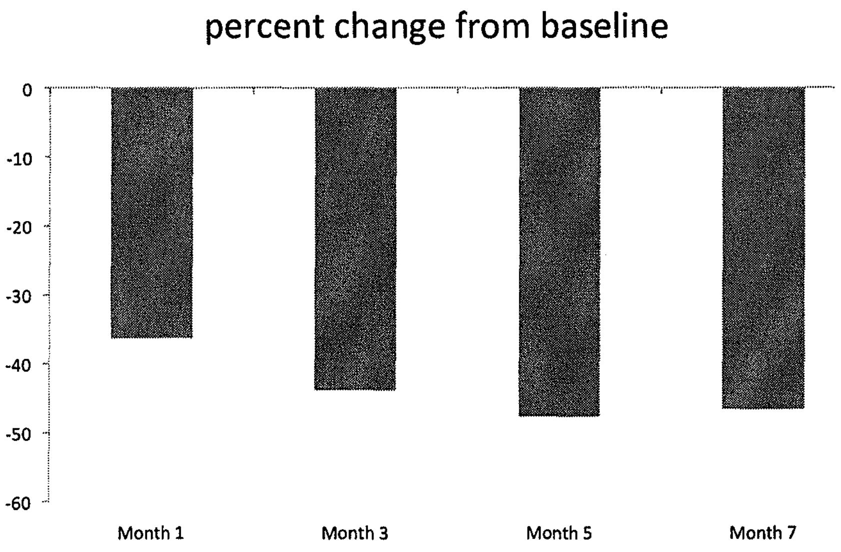
FIG. 9B is a bar graph demonstrating the percent change from baseline of corneal staining in the same patients treated with topical IL-1 receptor antagonist.

As shown in FIGS. 9A and 9B, corneal staining was utilized to measure ocular surface disease treated with topical IL-1 receptor antagonist. Specifically, the application of fluorescein was used to detect epithelial damage in the cornea, and each patient's disease severity was graded using the Oxford scale. The data demonstrate a significant reduction in staining (severity of disease) with topical blockade of IL-1 using the IL-1 receptor antagonist. Specifically, a significant change was observed from baseline to 7 months follow-up after treatment with IL-1 receptor antagonist.

Figures 10A, 10B:
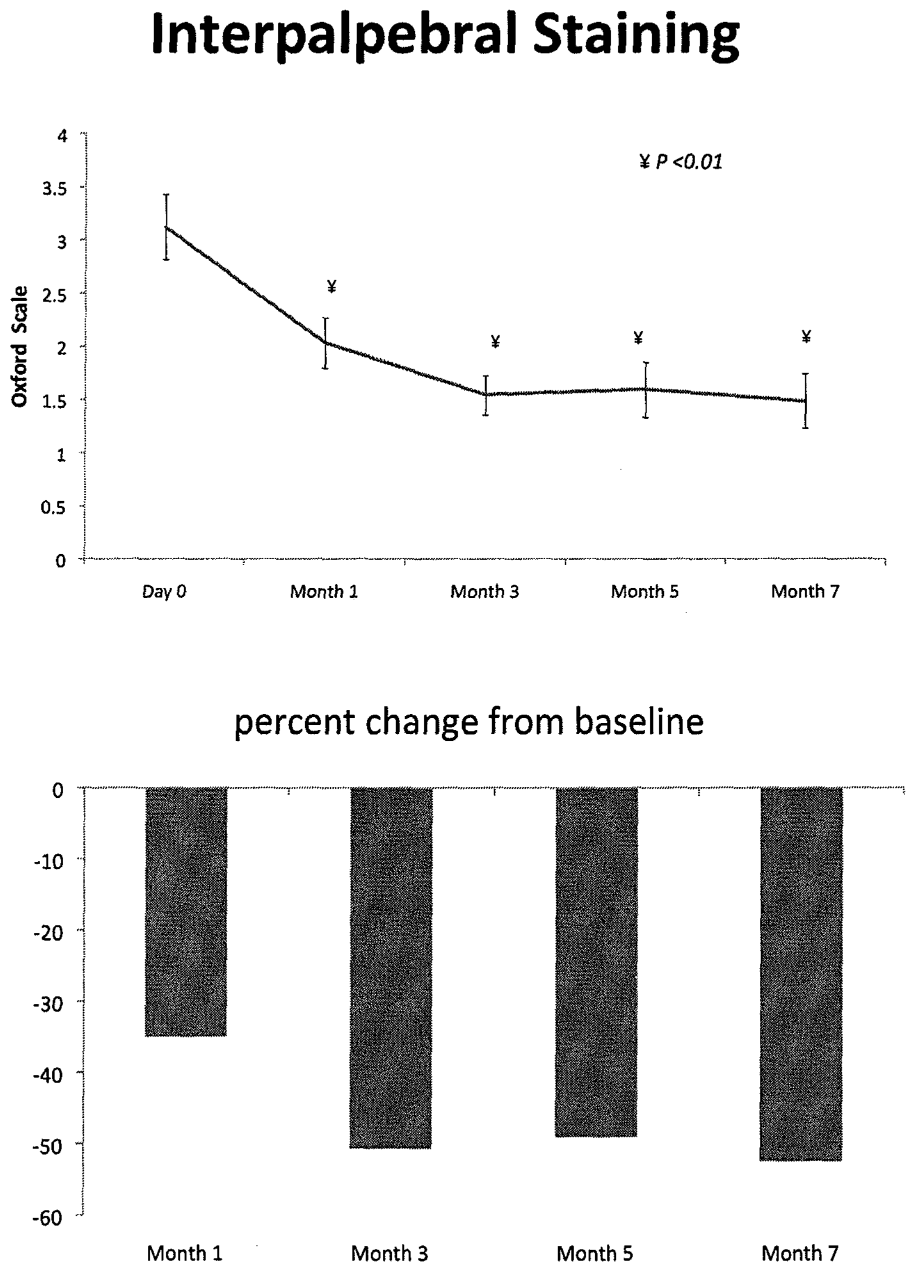
FIG. 10A is a line graph demonstrating mean interpalpebral staining in 70 human patients with ocular surface inflammatory disorder and dry eyes treated with topical IL-1 receptor antagonist.
FIG. 10B is a bar graph demonstrating the percent change from baseline of interpalpebral staining in the same patients treated with topical IL-1 receptor antagonist.
Figure 11A:
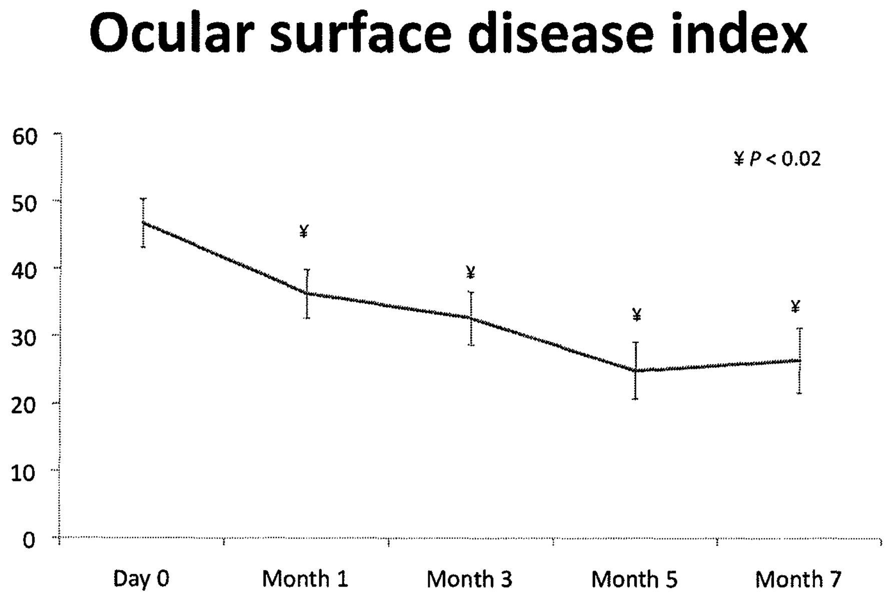
FIG. 11A is a line graph showing mean ocular surface disease index in 70 human patients with ocular surface inflammatory disorder and dry eyes treated with topical IL-1 receptor antagonist.
Figure 11B:
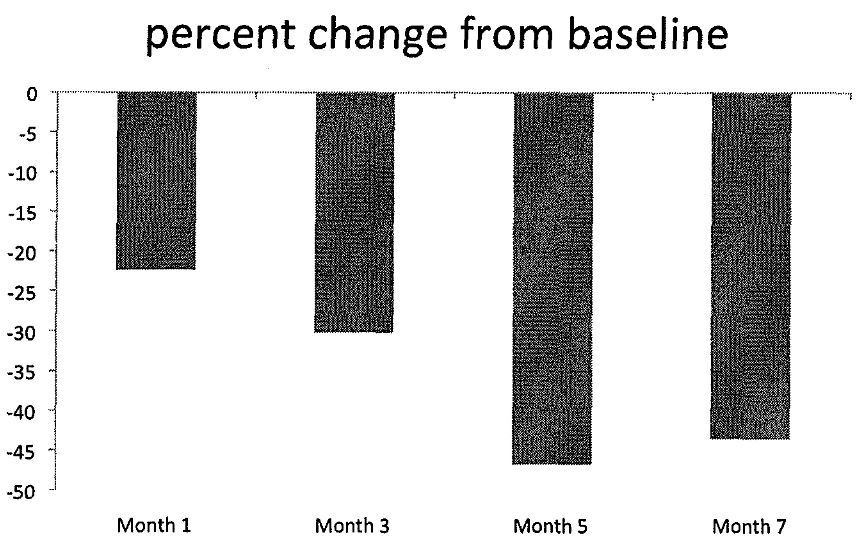
FIG. 11B is a bar graph showing the percent change from baseline of ocular surface disease index in the same patients treated with topical IL-1 receptor antagonist.

As depicted in FIGS. 10A and 10B, lisamine green staining was utilized to detect damage to the conjunctival epithelium, and each patient's disease was graded using the standardized Oxford scale. A significant reduction in interpalpebral (conjunctival) staining (severity of disease) was observed from baseline to 7 months follow-up after treatment with IL-1 receptor antagonist. Ocular surface disease index (OSDI) is a validated instrument for measuring dry eye disease symptoms' severity and effect on vision-related function. The score ranges from 0 (no symptoms) to 100 (maximal symptoms and visual dysfunction in all categories), with higher scores representing greater disability. OSDI was determined for each patient treated with IL-1 receptor antagonist (FIGS. 11A and 11B). OSDI score decreased significantly from baseline to 7 months follow-up after treatment with IL-1 receptor antagonist.

Figure 12:
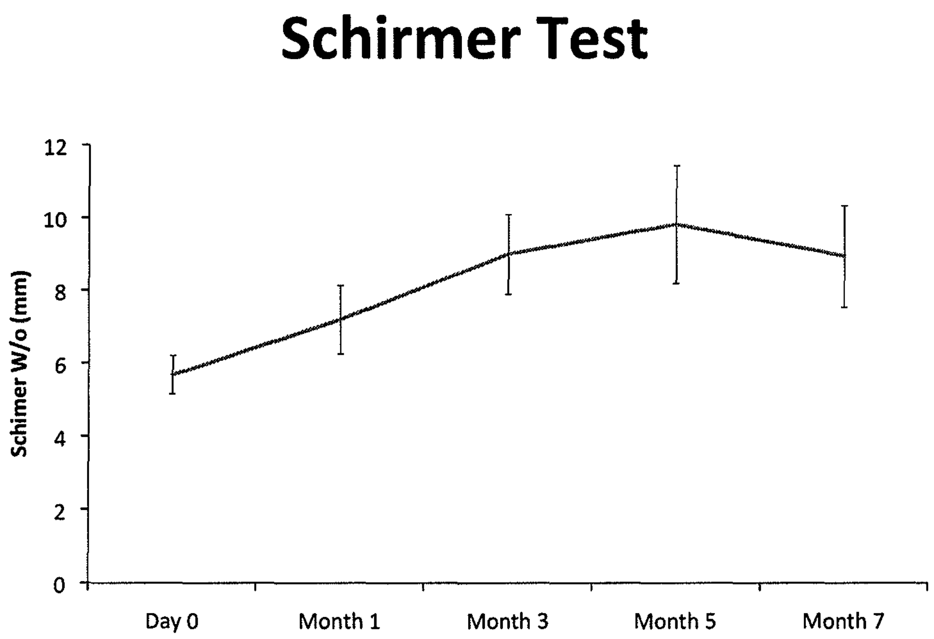
FIG. 12 is a line graph demonstrating mean tear volume in 70 human patients with an ocular surface inflammatory disorder and dry eyes treated with topical IL-1 receptor antagonist.

The Schirmer test measures the amount of tear produced by a patient's eye. The test is performed by placing a special scaled filter paper strip between the lower eyelid and the eyeball for 5 minutes. As shown in FIG. 12, tear volume increased from below 6 mm at baseline to ~9 mm at 7 months of follow-up. The data suggest an overall trend toward higher tear secretion with topical blockade of IL-1 with IL-1 receptor antagonist.

Figure 13:
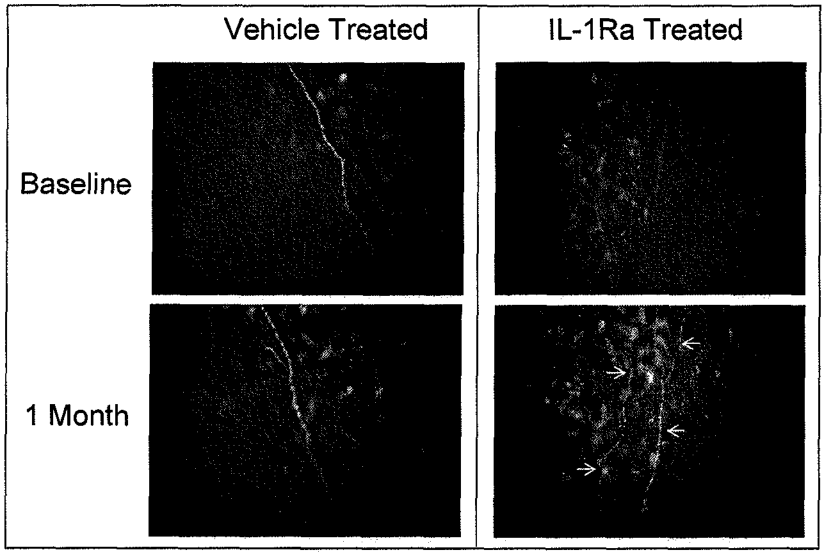
FIG. 13 is a series of photomicrographs depicting a corneal nerve regeneration in the human patients with ocular surface inflammatory disorder and dry eyes treated with topical IL-1 receptor antagonist or vehicle (lubricating eye drops).

FIG. 13 shows confocal micrographs of corneas from patients with dry eye disease before and after treatment with topical vehicle or topical IL-1Ra. One month of IL-Ra treatment promoted corneal nerve regeneration (marked with white arrows). By contrast, one month of vehicle treatment (lubricating drops) did not promote corneal nerve regeneration. These data support the observation made in mice (above) that selective blockade of cytokines with pathogenic roles in dry eye disease (IL-1, IL-17) provide a level of neuroprotection not observed with standard treatments.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for protecting or inducing outgrowth of corneal nerves in a subject in need thereof, comprising the steps of:

(a) identifying a subject with corneal nerve damage or loss by identifying in the subject a symptom from the group consisting of: abnormal tear production or dryness; abnormal blinking; difficulty or loss of ability to focus; decreased or lost visual acuity; or decreased or lost corneal sensitivity or identifying a subject with a sign of corneal nerve damage or loss, wherein the sign of corneal nerve damage or loss is a decrease of corneal innervation or sensation, a reduction in the number of nerve fibers or bundles innervating the cornea, death of neurons innervating the cornea, a decrease or loss of neurotransmitter release, a decrease or loss of nerve growth factor release, abnormal tearing reflexes, abnormal blink reflexes, abnormal nerve morphology, appearance of abnormal nerve sprouts, abnormal tortuosity, increased bead-like nerve formations, thinning of nerve fiber bundles, or thickening of nerve fiber bundles; wherein said subject is characterized as having corneal nerve damage or loss that results from neurotrophic keratitis, herpes simplex, zoster keratitis, diabetes mellitus, trigeminal nerve damage, ocular or orbital or head surgery, head trauma, aneurysm, intracranial neurologic disease, keratorefractive procedures, photorefractive keratectomy (PRK), laser in situ keratomileusis (LASIK), ocular surface disease, dry eye syndrome, or peripheral neuropathy; and (b) locally administering to the cornea of said subject a composition that inhibits an activity of an inflammatory interleukin-1 cytokine, thereby enhancing corneal nerve outgrowth or reducing the development of abnormalities in nerve morphology or density, wherein said composition consists of a vehicle and a polypeptide consisting of the amino acid sequence of SEQ ID NO: 16.

2. The method of claim 1, wherein said activity comprises binding of an inflammatory IL-1 cytokine to an IL-1 receptor.

3. The method of claim 1, wherein said polypeptide is present in a concentration of 0.1-10% (mg/ml).

4. The method of claim 1, wherein said polypeptide is present in a concentration of 2.5% (mg/ml) or 5% (mg/ml).

5. The method of claim 1, wherein the form of said composition is a solid, a paste, an ointment, a gel, a liquid, an aerosol, a mist, a polymer, a film, an emulsion, or a suspension.

6. The method of claim 1, wherein said composition is administered topically.

7. The method of claim 1, wherein said method does not comprise systemic administration or substantial dissemination to non-ocular tissue.

8. The method of claim 1, wherein said vehicle is selected from the group consisting of a physiological acceptable salt, poloxamer analogs with carbopol, carbopol/HPMC, carbopol-methyl cellulose, a mucolytic agent, carboxymethylcellulose (CMC), hyaluronic acid, cyclodextrin, and petroleum.

9. The method of claim 8, wherein said mucolytic agent is N-acetyl cysteine.

10. A method for minimizing damage or loss of corneal nerves in a subject in need thereof, comprising the steps of:

(a) identifying said subject at risk of exposure to corneal nerve damage or loss that results from neurotrophic keratitis, herpes simplex, zoster keratitis, diabetes mellitus, trigeminal nerve damage, orbital or head surgery, head trauma, aneurysm, intracranial neurologic disease, keratorefractive procedures, photorefractive keratectomy (PRK), laser in situ keratomileusis (LASIK), ocular surface disease, dry eye syndrome, or peripheral neuropathy; and (b) locally administering to the cornea of said subject a composition that inhibits an activity of an inflammatory interleukin-1 cytokine prior to said exposure, thereby decreasing nerve degeneration and reducing the development of abnormalities in nerve morphology or density, wherein said composition consists of a vehicle and a polypeptide consisting of the amino acid sequence of SEQ ID NO: 16.

11. A method for reducing corneal lymphangiogenesis associated with a dry-eye associated ocular surface disease in a subject in need thereof, comprising the steps of:

(a) identifying a subject with corneal lymphangiogenesis, wherein said subject has a dry-eye associated ocular surface disease; and (b) locally administering to the cornea of said subject a composition that inhibits an activity of an inflammatory interleukin-1 cytokine, thereby inhibiting the ability of lymphatic vessels to expand within or invade corneal tissue and reducing corneal lymphangiogenesis associated with a dry-eye associated ocular surface disease, wherein said composition consists of a vehicle and a polypeptide consisting of the amino acid sequence of SEQ ID NO: 16.

12. The method of claim 11, wherein said activity comprises binding of an inflammatory IL-1 cytokine to an IL-1 receptor.

13. A method for minimizing corneal lymphangiogenesis associated with a dry-eye associated ocular surface disease in a subject in need thereof, comprising the steps of:

(a) identifying said subject at risk of developing lymphangiogenesis onset associated with a dry-eye associated ocular surface disease, wherein said subject is at risk of developing a dry-eye associated ocular surface disease; and (b) locally administering to the cornea of said subject a composition that inhibits an activity of an inflammatory interleukin-1 cytokine prior to said development, thereby inhibiting the ability of lymphatic vessels to form or expand within, or to invade corneal tissue, wherein said composition consists of a vehicle and a polypeptide consisting of the amino acid sequence of SEQ ID NO: 16.

14. A method for reducing the induction of immunity to corneal antigens in a cornea in a dry-eye associated ocular surface disease of a subject in need thereof, comprising the steps of:

(a) identifying a subject with said induction of immunity to corneal antigens in dry-eye associated ocular surface disease; and (b) locally administering to the cornea of said subject a composition that inhibits an activity of an inflammatory interleukin-1 cytokine, thereby inhibiting the ability of lymphatic vessels to expand within or to invade corneal tissue and reducing the induction of immunity to corneal antigens, wherein said lymphatic vessels permit the transport of immune cells between said corneal tissue and lymphoid tissues and the initiation of an immune response to corneal antigens, wherein said composition consists of a vehicle and a polypeptide consisting of the amino acid sequence of SEQ ID NO: 16.

15. A method for minimizing induction of immunity to corneal antigens in a cornea of a subject in need thereof, comprising the steps of:

(a) identifying said subject at risk of developing said immunity to corneal antigens in dry-eye associated ocular surface disease; and (b) locally administering to the cornea of said subject a composition that inhibits an activity of an inflammatory interleukin-1 cytokine prior to said development, thereby inhibiting the ability of lymphatic vessels to expand within or to invade corneal tissue and minimizing said induction of immunity to corneal antigens, wherein said lymphatic vessels permit the transport of immune cells between said corneal tissue and lymph nodes and the initiation of an immune response to corneal antigens, wherein said composition consists of a vehicle and a polypeptide consisting of the amino acid sequence of SEQ ID NO: 16.

* * * * *